United States Patent
Sasaki

(10) Patent No.: US 11,980,529 B2
(45) Date of Patent: May 14, 2024

(54) CYLINDRICAL BANDAGE

(71) Applicant: TRESTECH CO., LTD., Aichi (JP)

(72) Inventor: Toshiya Sasaki, Aichi (JP)

(73) Assignee: TRESTECH CO., LTD., Aichi (JP)

( * ) Notice: Subject to any disclaimer, the term of this patent is extended or adjusted under 35 U.S.C. 154(b) by 468 days.

(21) Appl. No.: 16/844,254

(22) Filed: Apr. 9, 2020

(65) Prior Publication Data
US 2020/0323697 A1 Oct. 15, 2020

(30) Foreign Application Priority Data
Apr. 9, 2019 (JP) .................................. 2019-073950

(51) Int. Cl.
*A61F 13/08* (2006.01)
*A61F 13/00* (2006.01)
(Continued)

(52) U.S. Cl.
CPC ............ *A61F 13/08* (2013.01); *A61F 13/064* (2013.01); *A61F 13/10* (2013.01); *A61F 13/104* (2013.01);
(Continued)

(58) Field of Classification Search
CPC ........ A61F 13/08; A61F 13/064; A61F 13/10; A61F 13/104; A61F 13/06; A61F 13/00; A61F 2013/00097; A61F 2013/00238; A61F 2013/00093; A61F 5/3723; A61F 5/0118; A61F 5/013; A61F 5/05858; A61F 5/0585; A61F 5/01; A61F 5/0109; D04B 1/24; D04B 1/26; D04B 1/265;
(Continued)

(56) References Cited

U.S. PATENT DOCUMENTS 5,965,223 A * 10/1999 Andrews ................ D02G 3/442
428/36.1
6,052,824 A * 4/2000 May ........................ A41D 13/08
2/16
(Continued)

FOREIGN PATENT DOCUMENTS

BE 823583 A 4/1975
EP 3459510 A1 3/2019
(Continued)

OTHER PUBLICATIONS

Machine translation of JP-2006219805-A (Year: 2006).*
(Continued)

*Primary Examiner* — Caitlin A Carreiro
(74) *Attorney, Agent, or Firm* — Sughrue Mion, PLLC; Richard C. Turner

(57) ABSTRACT

A cylindrical bandage is held in place without using binding means such as strings tied to an upper limb. Additionally, the cylindrical bandage for a lower limb or upper limb fits the shapes and dimensions of a body part and stays on the body part and thus allows great increase in venous return. The cylindrical bandage includes a tubular knit being of a length corresponding to a length of an arm or a leg and a gutter-shaped knit extending from a lengthwise first end of the tubular knit. This gutter-shaped knit has smaller circumferential length than the first end of the tubular knit and has a cut-out section with a horseshoe or V shape.

9 Claims, 15 Drawing Sheets

(51) Int. Cl.
 *A61F 13/06* (2006.01)
 *A61F 13/10* (2006.01)
 *D04B 1/24* (2006.01)

(52) U.S. Cl.
 CPC ...... *D04B 1/24* (2013.01); *A61F 2013/00097* (2013.01); *A61F 2013/00238* (2013.01); *D10B 2509/028* (2013.01)

(58) Field of Classification Search
 CPC ... D04B 9/46; D04B 9/52; D04B 9/56; D04B 11/28; D04B 11/34; D10B 2509/028; A41D 13/08; A41D 13/0543; A41D 17/00; A41D 17/02
 USPC .......... 602/4–5, 20, 23, 60–63; 2/16, 22, 23; 128/878, 882; 66/178 R, 183, 185, 178 A
 See application file for complete search history.

(56) References Cited

U.S. PATENT DOCUMENTS

| | | | | |
|---|---|---|---|---|
| 6,119,274 | A * | 9/2000 | Graham | A41D 17/00 2/242 |
| 9,301,553 | B1 * | 4/2016 | Donovan | A41D 1/00 |
| 2004/0106887 | A1 * | 6/2004 | Schneider | A61F 13/061 602/23 |
| 2005/0165341 | A1 * | 7/2005 | Smith | D04B 1/22 623/32 |
| 2005/0177927 | A1 * | 8/2005 | Hettich | A61F 13/08 2/409 |
| 2010/0107702 | A1 * | 5/2010 | Rad | D04B 1/243 66/178 R |
| 2016/0198797 | A1 | 7/2016 | Ikenaka | |
| 2017/0342611 | A1 * | 11/2017 | Achtymichuk | A41D 31/14 |
| 2018/0353345 | A1 * | 12/2018 | Sasaki | D04B 1/18 |

FOREIGN PATENT DOCUMENTS

| | | | |
|---|---|---|---|
| JP | 3-8231 | | 7/1928 |
| JP | 50-25732 | U | 3/1975 |
| JP | 56-34814 | U | 4/1981 |
| JP | 9-296343 | A | 11/1997 |
| JP | 2004-254731 | A | 9/2004 |
| JP | 2006-219805 | A | 8/2006 |
| JP | 2006219805 | A * | 8/2006 |

OTHER PUBLICATIONS

Communication dated Aug. 21, 2020, from the European Patent Office in application No. 20168639.1.

Communication dated Dec. 10, 2019 by the Japanese Patent Application No. 2019-073950.

Communication dated Apr. 14, 2020 by the Japanese Patent Application No. 2019-073950.

* cited by examiner

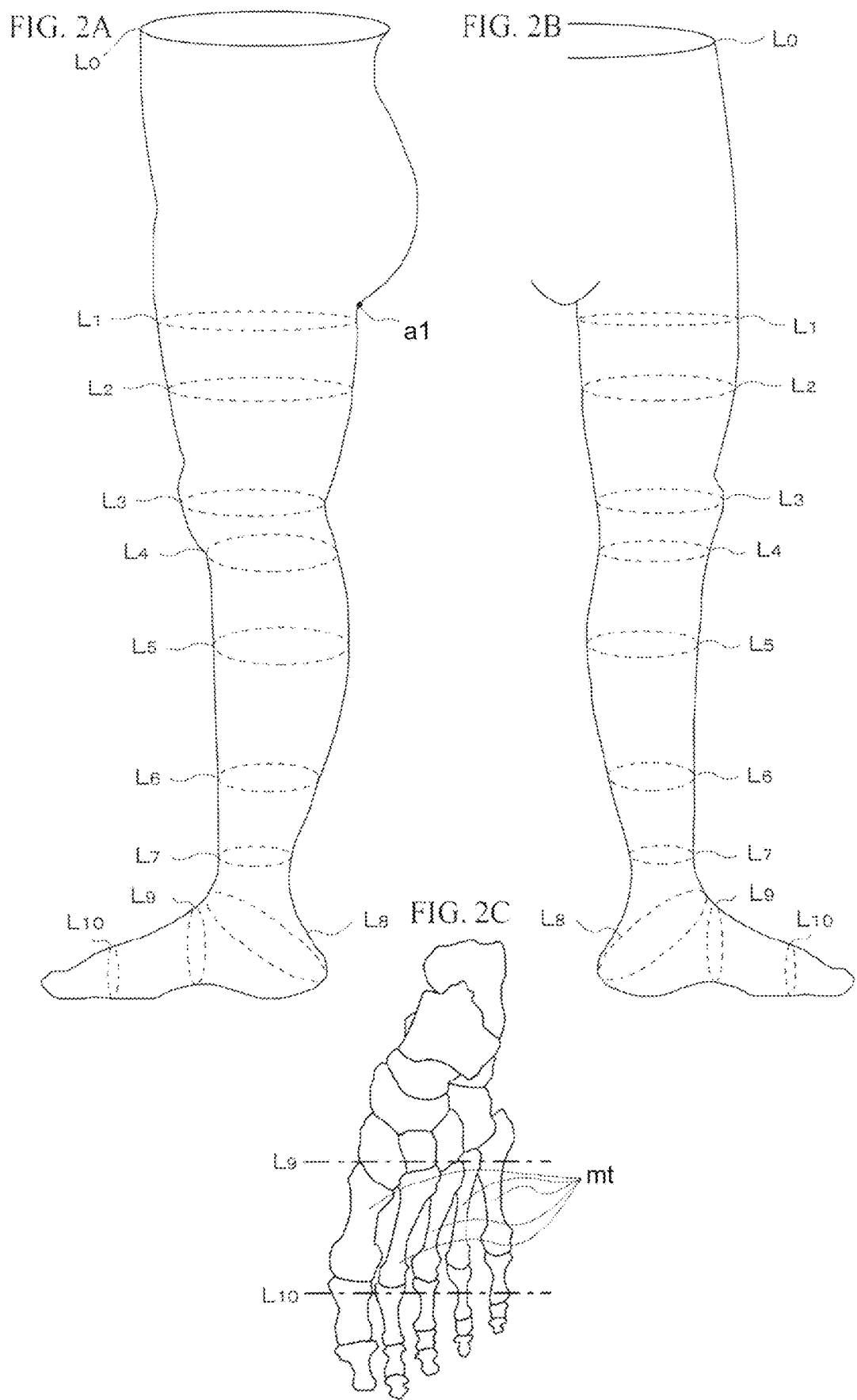

NL  ST

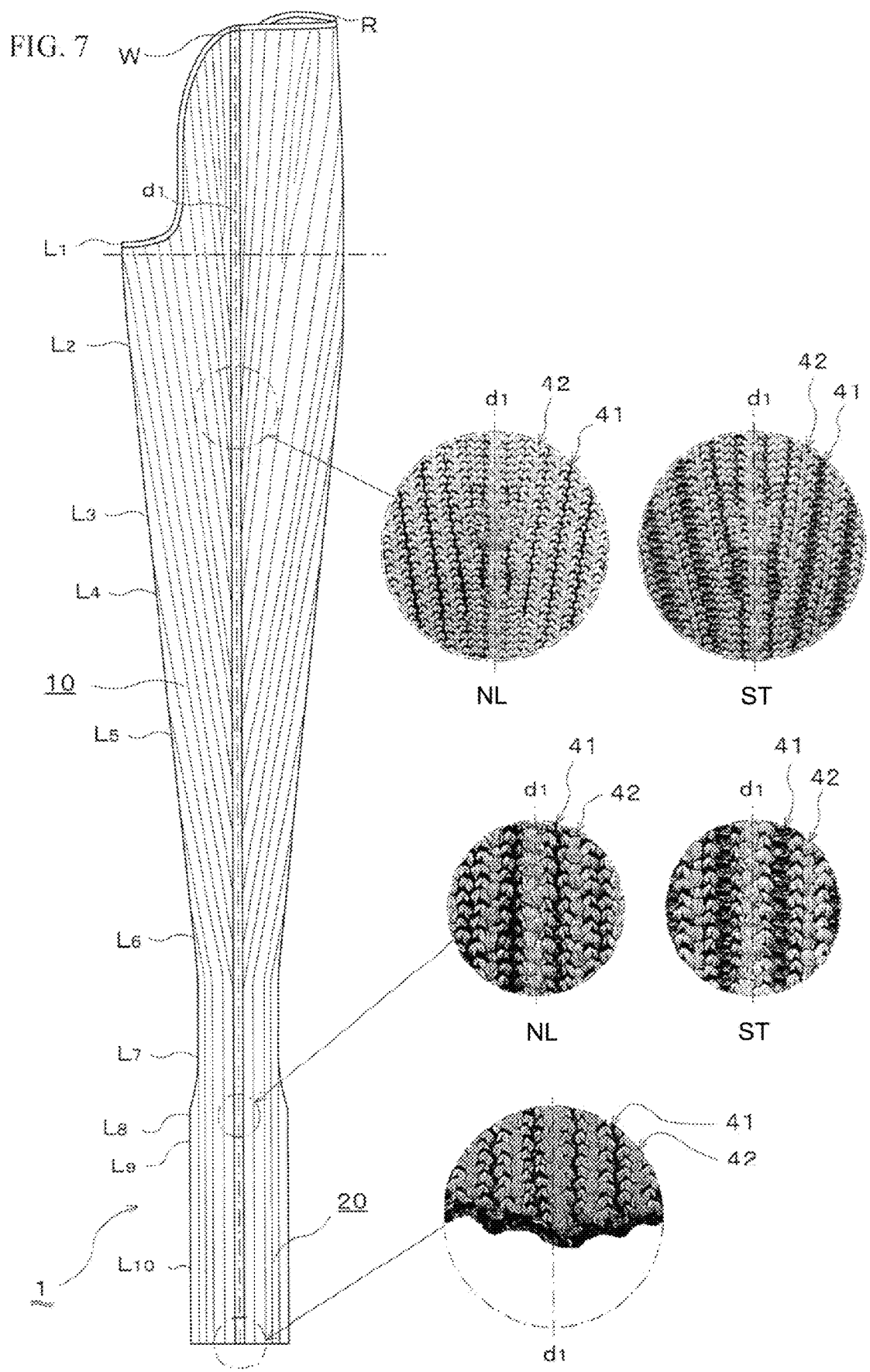

FIG. 14A
FIG. 14B
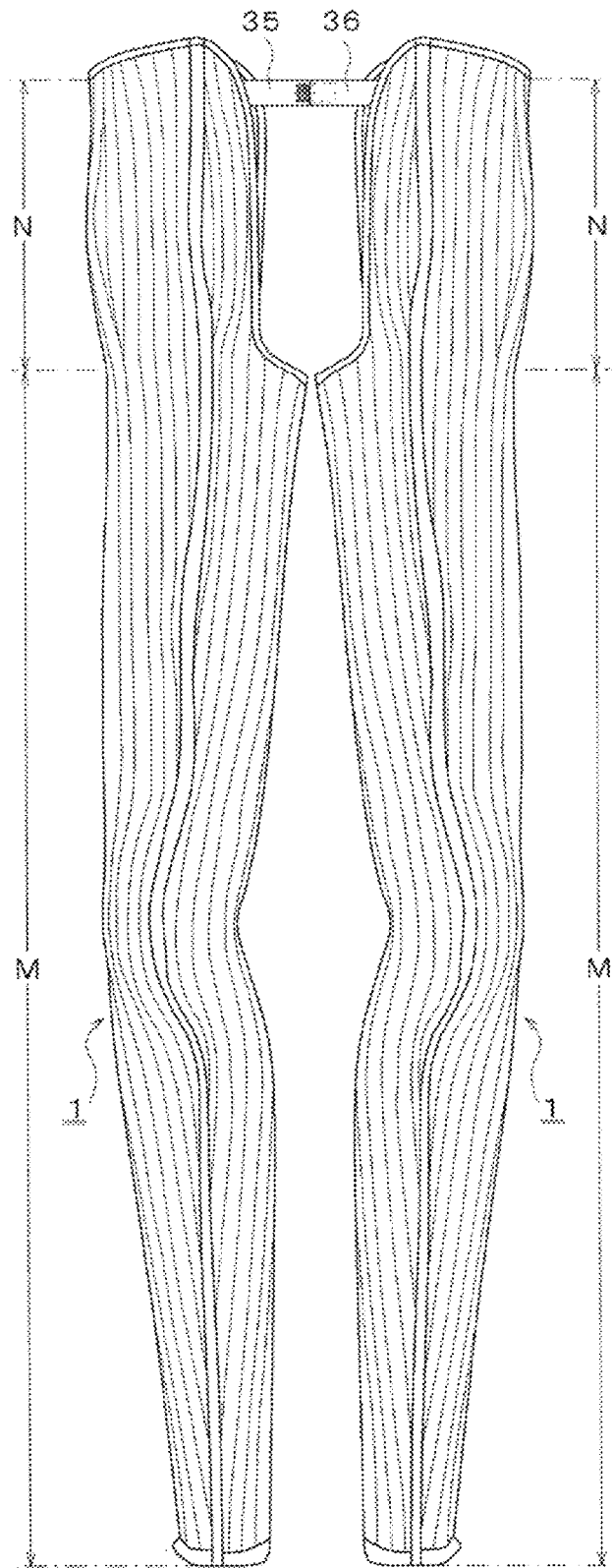
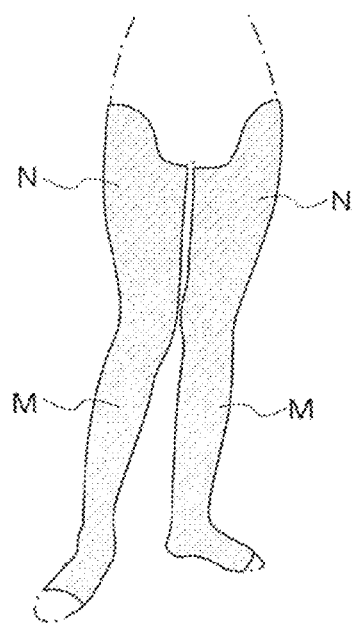

FIG. 15A
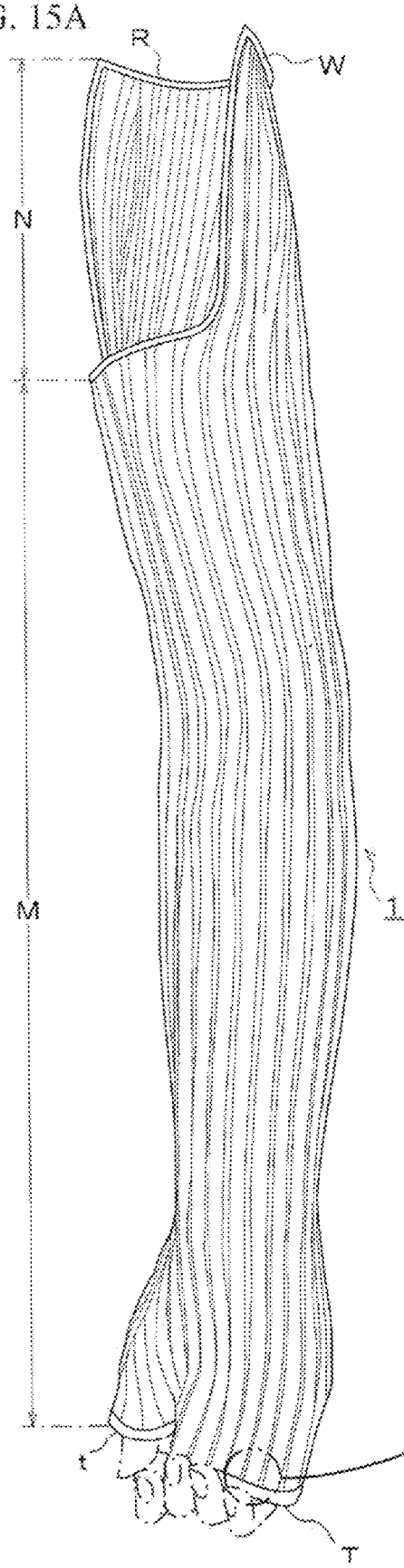
FIG. 15B
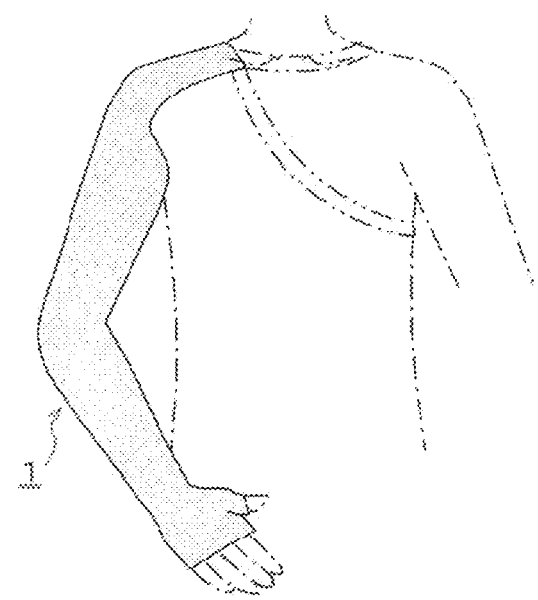
FIG. 15C
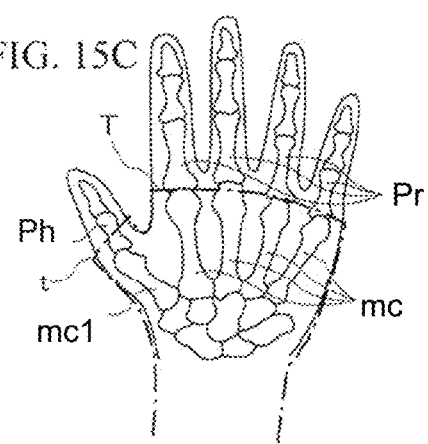
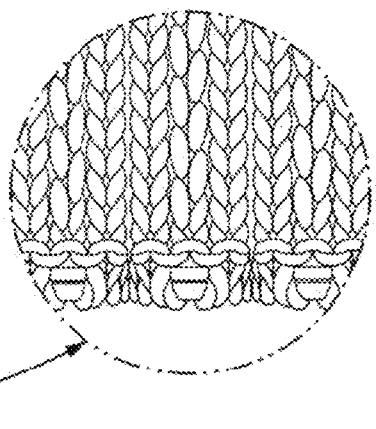

CYLINDRICAL BANDAGE

The present invention is based on Japanese Patent Application No. 2019-73950, filed on Apr. 9, 2019, the contents of which are hereby incorporated by reference.

TECHNICAL FIELD

The present invention relates to cylindrical bandages as garments that can compress body parts. The cylindrical bandages are used as bandages for compression, such as supporters for lower limb, sleeves, stockings, tights, supporters for elbow, or supporters for hands or wrists. In particular, the present invention relates to cylindrical bandages for prevention and treatment of diseases such as reduced venous return and lymphedema.

BACKGROUND ART

In medical fields, compression therapy using compression bandages or compression stockings are effective for prevention and treatment of diseases, for example, vein disorders such as varicose vein and venous thrombosis of the lower extremity, and lymphedema. The compression bandages are worn on the affected area and compressing it. The compression stockings are designed so as to gradually become less constructive towards one end. In particular, there are no drugs and surgical operations as cure for lymphedema. Presently treatment for lymphedema is mainly compression therapy as physical therapy. The lymphedema is a condition of localized swelling with fluid-rich including protein lymphocytes in the tissues due to a blockage of compromised lymph passages.

Compression bandages wrapped around the body part can fit the shapes or dimensions of the body part and thus provide desired compression. However, such compression bandages need to special technique for providing suitable compression in accordance with conditions of an affected part. Unstable compression may adversely affect the conditions. It is difficult that the bandage is suitably put on the body part without help of familiars including doctors and nurses.

Whereas, compression bandages with a tubular shape, such as compression stockings, sleeves, or cylindrical bandages, which each may tightest at an ankle and gradually become less constructive towards a thigh, can be easily put on without help of the familiars and can stay on a body part. Such compression bandages do not need compression adjustment while worn.

Some conventional compression stockings used in the medical field, specifically, lower limb compression stockings have a bulge or round part to correspond to shapes of a heel. Unfortunately, such medical elastic stockings have an ankle part with some wrinkles when worn on a leg. Specifically, such medical elastic stockings loose at a foot part ranging from a malleolus to an instep and wrinkles at the instep. Such horizontal wrinkles bite a skin and provides compression concentration accordingly. This may cause decrease in venous return in some cases. Further, the stockings loose at the part around the malleolus, where excess lymph fluid is easily trapped, specifically, at the back side of the malleolus. This provides less compression on the part around the malleolus. Thus, conventional medical elastic stockings fail to provide constant compression. To increase compression on the part around the malleolus, cushioning or sponge such as resin foam is disposed between the affected part and conventional medical elastic stockings worn on a body part in actuality.

Conventional knitting using circular knitting machines allows the shapes of a knitted fabric to be varied by varying the tension of knitting yarn and stitch density. However, the number of the needs used for knitting is not changed and knitted width is constant. Thus, conventional knitting using circular knitting machines do not offer flexibility at dimensions and shapes. It is difficult for this conventional knitting to fit the part around ankle.

For circular knitting using circular knitting machines with a cylinder having needles, a tubular leg part is first knitted using all needles on the cylinder rotating in a fixed direction. Following this, a heel part is knitted using part of the needles on the cylinder turning at predetermined angle and a tubular foot part is then knitted using again all needles on the rotating cylinder in a fixed direction. This makes stockings for a lower limb.

Unfortunately, for such a circular knitting using circular knitting machines, the number of the needles used in knitting or the knitted width is constant. Thus, the circumference of stockings is limited to a predetermined range. That is, the tubular diameter of stockings is constant. Inevitably, the bottom of a leg and the top of a leg are the same knitted width or the same circumference. The dimensions of a heel part are limited to a predetermined range. It is difficult to design the tubular diameter close fitting the part around an ankle. Further, when having the ankle with higher stitch density and smaller diameter, the stockings has poor breathability and easily causes sweaty. Furthermore, such stockings are difficult to put on or take off.

In knitting of the heel part following a leg part, the turning angle of the cylinder gradually decreases and after that the turning angle of the cylinder gradually increases. The foot part is then knitted. In this knitting of the heel part, the knitted width gradually decreases and after that the knitted width gradually of the cylinder gradually increases. Unfortunately, the partial reverse knitting and increasing and decreasing of the knitted width in the knitting of the heel part make gore lines, which appears as joint borders between the ends of knitted width with increase and decrease in stitches. As a result, the knit fabric of the heel part having gore lines winkles easily and does not stretch easily.

For such a circular knitting using circular knitting machines, the knitted fabric is loose on the instep at the front of an ankle while the knitted fabric is tense on the heel at the back of the ankle. Thus, it is difficult for the stockings knitted by circular knitting machines to provide uniform compression to the malleolus part having corrugation of a foot. Additionally, conventional compression stockings knitted by circular knitting machines easily wrinkles at the front of the ankle and thus easily provide compression concentration. Furthermore, the conventional compression stockings knitted by circular knitting machines has higher stitch density at the ankle part. Such conventional compression stockings have poor breathability and easily cases sweaty. In particular, the stockings made of nylon may cause allergy and eczema.

With respect to compression, Japanese Unexamined Patent Application Publication No. 2006-219805 discloses cover wear for lower limbs. This wear has protuberances with pile stitch. These protuberances are on an inner surface, which will get in direct contact with a target skin. The part corresponding to the front of crus has the protuberances spaced apart from each other while the part corresponding to the back of crus has the protuberances extending longitudinally. These protuberances make partial compression or pressure providing stimulation and massage effect for reducing swelling and fatigue.

It is known that flatbed knitting machines with the front-and-rear needle beds can also knit socks having heel part, as disclosed in Patent Application Publication No. 9-296343.

DISCLOSURE OF THE INVENTION

Technical Problem

Unfortunately, according to JP-A-2006-219805, the pressure is applied to only a leg, not to a foot including malleolus. Further, there is a difference in the partial compression between the front and the back of the foot. This provides uneven or imbalanced compression and partial effectiveness of compression. This may cause discomfort.

The socks disclosed in JP-A-9-296343 are ordinary socks for daily use. Such socks are designed so as to fit loose in view of repeated bending of the front around ankle and easy-to-put-on and easy-to-take-off of the socks. Any ideas of providing uniform compression to even the part around the malleolus are not disclosed.

As shown in FIG. 1A, a commercial bandage body 100 worn on a lower limb as s a long sock is suspended using a suspender stocking 101 and waist belt 103. An attachment 102 on the end of the lower limb bandage body 100 causes uncomfortable feeling even though the suspender is made of a fabric or lace.

As shown in FIGS. 1B and 1C, a flat braid 201 and a flat braid 202 are joined to a bandage body 200 worn on an upper limb by sewing. The flat braid 202 disposed on a shoulder side and the flat braid 201 disposed on a lung side surround and hold the body. This allow the upper limb bandage body 200 to be fixed. The flat braid 201 and the flat braid 202 as a pair of flat braids 205 are detachably joined together with hook-and loop fastener (Magic Tape.®). Even though the bandage body 200 with a length corresponding to the length of an arm has the flat braid 201 and the flat braid 202, the bandage body 200 is unsteady, that is, it often slides downward, falls down, or is detached from the shoulder. This causes uncomfortable feeling. Unfortunately, the flat braid 202, the bandage body 200 may be wound around a user's body when the user rolls over while sleeping. This is undesirable.

It is an object of the present invention to provide a cylindrical bandage that is held in place without using binding means such as strings tied to an upper limb. Additionally, the cylindrical bandage for a lower limb or upper limb fits the shapes and dimensions of a body part and stays on the body part and thus allows great increase in venous return.

Solution to Problem

A cylindrical bandage according to a first aspect of the present invention includes a tubular knit with a length corresponding to the length of an arm or a leg and a gutter-shaped knit extending from the first end of the tubular knit. The gutter-shaped knit has a smaller length of a circumferential direction than the first end of the tubular knit and has a gutter-shape. This gutter-shaped knit has a cut-out section giving it a horseshoe or V shape.

The tubular knit is of a length corresponding to that of an arm or a leg. The tubular knit has a base structure formed of the stitches of a base yarn, viewed from the cross-section perpendicular to the length direction of an arm or a leg. The base structure includes the stitches of an elastic yarn. The elastic yarn, which has higher elasticity than the base yarn, may hide behind the base yarn in ribs on the inner surface to avoid contact with the skin of users.

The tubular knit, which is of a length corresponding to that of a leg including the ankle, has a degree of elasticity to prevent rise or fall slip of the knit. The tubular knit also has a degree of stiff to prevent the gutter-shaped knit from being weighted down by its own weight, or to support the weight of the gutter-shaped knit, and allow the gutter-shaped knit to stand. The stitches of the tubular knit and the gutter-shaped knit may affect the degree of elasticity.

Standing of the gutter-shaped knit does not depend on merely stiffness or Young's modulus. The gutter-shaped knit may visually stand.

In particular, the gutter-shaped knit has a shorter knitting width than the one end of the tubular knit and has a cut-out section making it a horseshoe or V shape. The bypass edge of this cut-out section with a horseshoe or V shape of the gutter-shaped knit may affect standing of the gutter-shaped knit.

The tubular knit is of a length corresponding to that of an arm or a leg. The tubular knit has the base structure formed of the stitches of the base yarn, viewed from the cross-section perpendicular to the length direction. The base structure includes the stitches of the elastic yarn. The elastic yarn, which has higher elasticity than the base yarn, may hide behind the base yarn in ribs of the inner to avoid contact with the skin of users.

The gutter-shaped knit extends from the one end of the tubular knit, which is of a length corresponding to that of a leg. The knitting width gradually decreases from the one end of the tubular knit to the gutter-shaped knit. This makes the end of the cut-out section with a horseshoe or V shape.

The cylindrical bandage according to the first aspect of the present invention preferably has the gutter-shaped knit having a middle with the varying numbers of the stitches.

The number of the stitches of the gutter-shaped knit varies from that of the tubular knit. Further, varying the number of the stitches makes the cut-out section a horseshoe or V-shaped or gives a horseshoe or V-shaped edge. The both widthwise ends may have the same lengthwise length. The widthwise distance between the both widthwise ends may widen towards the open end. In the gutter-shaped knit, the number of the stitches gradually decreases towards the open end from the tubular knit to give a horseshoe or V-shaped edge. The both widthwise ends may have the same lengthwise length. The widthwise distance between the both widthwise ends may widen towards. In particular, the gutter-shaped knit is wider at the middle. Such a gutter-shaped knit holds the shoulder including the collarbone stably while allowing shoulder movements on the inside.

The horseshoe or V-shaped edge described above means the widthwise distance between the both widthwise ends of the upper part is wider than that of the lower part. The horseshoe shape includes a shape widening towards the upper part.

The cylindrical bandage according to the first aspect of the present invention preferably has the gutter-shaped knit with a thickness in a range of 2 to 15 mm and the tubular knit with a thickness of 2 to 15 mm. Such a thickness does not cause the knit fabric to stick to the skin of target body. Thus, the gutter-shaped knit, which extends from the tubular knit with a length corresponding to the length of an arm or a leg, fits shoulder or hip tightly.

The cylindrical bandage according to the first aspect of the present invention preferably has the tubular knit having the bottom other end placed on a foot part corresponding to metatarsal bones.

Thus, the other end or a second end of the tubular knit having is placed on the foot part corresponding to metatarsal bones. This prevent the rise or fall shift of the tubular knit. The specified bottom end of the tubular knit is not required to be exactly placed on the foot part corresponding to metatarsal bones. The bottom end of the tubular knit is preferably placed at or near metatarsal bones.

The cylindrical bandage according to the first aspect of the present invention preferably has the tubular knit having the top other end placed on a hand part corresponding to metacarpal bones.

Thus, the other end or a second end of the tubular knit having is placed on the hand part corresponding to metacarpal bones. This prevent the rise or fall shift of the tubular knit. The specified bottom end of the tubular knit is not required to be exactly placed on the hand part corresponding to metacarpal bones. The bottom end of the tubular knit is preferably placed at or near metacarpal bones.

The cylindrical bandage according to the first aspect of the present invention preferably has the gutter-shaped knit at least that is symmetrical about a center perpendicular line in an extended configuration of the gutter-shaped knit and the tubular knit.

The center perpendicular line is the line of symmetry. The cylindrical bandage including the tubular knit and the gutter-shaped knit extending from the tubular knit longitudinally is preferably symmetrical about the center perpendicular line.

Advantageous Effects of the Invention

A cylindrical bandage according to a first aspect of the present invention includes a gutter-shaped knit extending from the first end of the tubular knit, which is of a length corresponding to that of an arm or a leg. The gutter-shaped knit has a shorter knitting width than the first end of the tubular knit and has a cut-out section with horseshoe or V shape. This gutter-shaped knit has a gutter-shape. The tubular knit has an inner in which an elastic yarn with higher elasticity than a base yarn may hide behind the base yarn in ribs to avoid contact with the skin of users.

Thus, the cylindrical bandage includes the gutter-shaped knit extending from the first end of the tubular knit. The length of the circumferential direction gradually decreases from the tubular knit to the gutter-shaped knit. This makes the cut-out section with a horseshoe or V shape. This gutter-shaped knit has a horseshoe or C shape in cross-section. Such a gutter-shaped knit stably holds a shoulder including collarbones while allowing shoulder movements on the inside. This prevents the cylindrical bandage from falling down or allows the cylindrical bandage to stay on a body part, even when users wearing the cylindrical bandage roll over while sleeping.

The gutter-shaped knit has a horseshoe or V shaped edge, which is made by varying the number of the stitches. The horseshoe or V shaped edge yields tight grasp. Further, varying the number of the stitches allows the knitted fabric to fit tightly. This allows the gutter-shaped knit to stably hold the shoulder including the collarbones.

The horseshoe or V shape may be substantially or generally horseshoe or V shape.

In the cylindrical bandage according to the first aspect of the present invention, the gutter-shaped knit preferably has a horseshoe or V shaped edge. The number of the stitches of the gutter-shaped knit varies from that of the tubular knit. Specifically, the knitting width or the length of the circumferential direction gradually decreases from the tubular knit to the gutter-shaped knit with the cut-out section shaped in horseshoe or V. Such a gutter-shaped knit stands on the tubular knit and is flexible. Thus, the cylindrical bandage fits tightly without using binding means such as strings. This cylindrical bandage achieves tight fitting for the varying cross-sections of the body part. The cylindrical bandage is used as a bandage for compression, such as a supporter for lower or upper limb, a sleeve, a stocking, tights, a supporter for elbow, or a supporter for a hand or a wrist. This cylindrical bandage allows increase in venous return and is effectiveness for prevention and treatment of diseases such as venous disorders and lymphedema. In particular, the cylindrical bandage stably stays on the body part.

Thus, the cylindrical bandage includes the gutter-shaped knit contiguous with the tubular knit. This gutter-shaped knit extends from the one lengthwise end of the tubular knit. The gutter-shaped knit has a one lengthwise end that is shorter in the circumferential direction than the tubular knit ones. This gutter-shaped knit has a horseshoe or C shape in cross-section and the cut-out section with a horseshoe or V shape. Such a gutter-shaped knit holds the shoulder including the collarbone stably while allowing shoulder movements on the inside. This prevents the cylindrical bandage from falling down or allows the cylindrical bandage to stay on a body part, even when users wearing the cylindrical bandage roll over while sleeping.

The gutter-shaped knit has the horseshoe or V-shaped edge, which is made by varying the number of the stitches. The horseshoe or V-shaped edge yields tight grasp. Further, varying the number of the stitches, which makes the cut-out section horseshoe or V shaped, or varying the thickness of the knitted fabric, or varying the dimensions or shapes also allows the knitted fabric to fit tightly. This allows the gutter-shaped knit to grasp the shoulder including the collarbone.

The cylindrical bandage includes the gutter-shaped knit having the horseshoe or V-shaped edge. The number of the stitches of the gutter-shaped knit varies from that of the tubular knit. Specifically, the knitting width or the length of the circumferential direction gradually decreases from the tubular knit to the gutter-shaped knit with the cut-out section shaped in horseshoe or V. Such a gutter-shaped knit stands on the tubular knit and is flexible. Thus, the cylindrical bandage fits tightly without using binding means such as strings. This cylindrical bandage tightly fits to even undulating parts or curvy parts of the body part. The cylindrical bandage is used as a bandage for compression, such as a supporter for lower or upper limb, a sleeve, a stocking, tights, a supporter for elbow, or a supporter for a hand or a wrist. This cylindrical bandage allows increase in venous return and is effectiveness for prevention and treatment of diseases such as venous disorders and lymphedema. In particular, the cylindrical bandage stably stays on the body part.

In the cylindrical bandage according to the first aspect of the present invention, the gutter-shaped knit preferably has a thickness of 2 to 15 mm and the tubular knit preferably has a thickness of 2 to 15 mm. The thicker knit fabric of the gutter-shaped knit and the tubular knit keeps its shape. Such a thicker knit fabric does not shift easily. Additionally, this knit fabric does not wrinkle easily even on movement or bend parts (for example, the instep side of a foot) when the cylindrical bandage is worn. Thus, compression concentration and tourniquet with the wrinkles biting is prevented.

In the cylindrical bandage according to the first aspect of the present invention, the tubular knit preferably has the bottom second end placed on a foot part corresponding to metatarsal bones. Thus, the second end of the tubular knit is placed on the foot part corresponding to the metatarsal bones. This prevents the gutter-shaped knit and the tubular knit from sliding along a leg even when user's weight is put on the knit. The gutter-shaped knit and the tubular knit keep fitting.

In the cylindrical bandage according to the first aspect of the present invention, the tubular knit preferably has the top second end placed on a foot part corresponding to metacarpal bones. Thus, the second end of the tubular knit is placed on the foot part corresponding to the metacarpal bones. This prevents the gutter-shaped knit and the tubular knit from sliding along an arm even when user's weight is put on the knit and the user's body part moves. The gutter-shaped knit and the tubular knit keep fitting.

The cylindrical bandage according to the first aspect of the present invention, the gutter-shaped knit at least is symmetrical about a center perpendicular line in an extended configuration of the gutter-shaped knit and the tubular knit. With symmetry, the gutter-shaped knit and the tubular knit is prevented from sliding even when user's weight is put on the knit and the user's body part moves. The gutter-shaped knit and the tubular knit keep fitting.

BRIEF DESCRIPTION OF DRAWINGS

FIG. 2A is a left side view of a leg and illustrates measured points of a body part used for determining the shapes of a cylindrical bandage according to an embodiment of the present invention. FIG. 2B is a front view of a left leg and illustrates measured points of a body part used for determining the shapes of a cylindrical bandage according to an embodiment of the present invention. FIG. 2C is a plain view of main bones of a foot and illustrates measured points of a body part used for determining the shapes of a cylindrical bandage according to an embodiment of the present invention.

FIG. 7 is a plain view of the cylindrical bandage according to an embodiment of the present invention viewed in a front overlaid on a back in which the front corresponds to the knee of a leg and the instep of a foot and the bake corresponds to the calf of the leg.

FIG. 14A is a perspective view of a pair of the cylindrical bandages according to an embodiment of the present invention in which the cylindrical bandage is used in combination. FIG. 14B is a view from the front of the cylindrical bandage worn a body part.

FIG. 15A is a perspective view of the cylindrical bandages for an upper limb according to an embodiment of the present invention. FIG. 15B is a reference view from the front of a body wearing the cylindrical bandage. FIG. 15C schematically illustrates the end of the cylindrical bandage covering a palm.

DESCRIPTION OF EMBODIMENTS

Figure 1A:
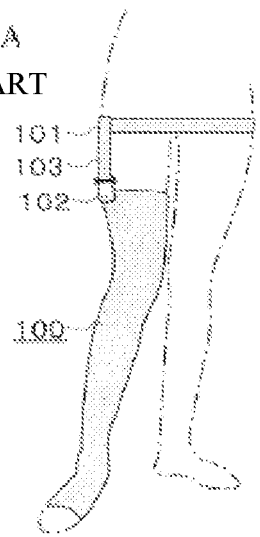
FIG. 1A illustrates a conventional cylindrical bandage worn on a right lower limb and an attachment used in the cylindrical bandage.
Figure 1B:
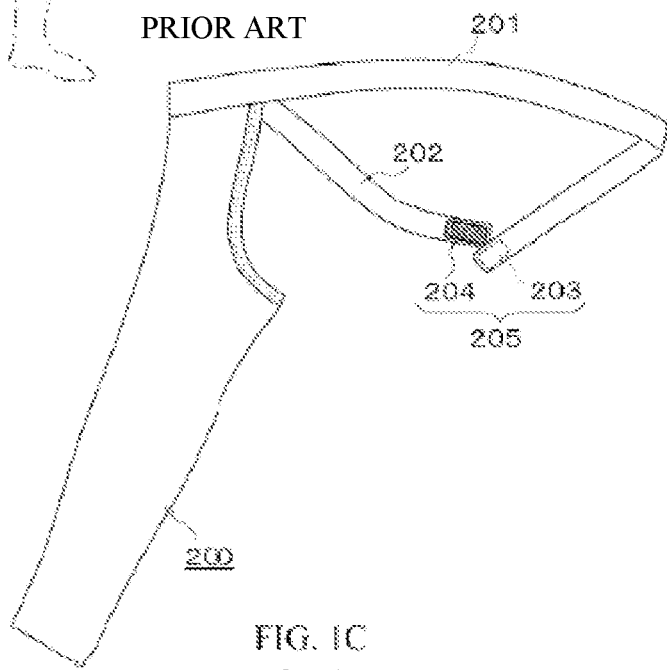
FIG. 1B illustrates a conventional cylindrical bandage worn on an upper limb and an attachment used in the cylindrical bandage.
Figure 1C:
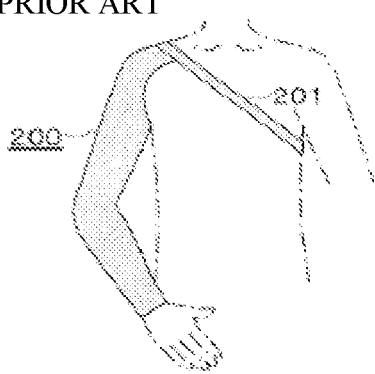
FIG. 1C is a front view of a right arm wearing the cylindrical bandage of FIG. 1B.

Embodiments of the present invention are described hereafter based on drawings.

In the embodiments of the present invention, the same marks and the same codes shown in the drawings mean the same or equivalent function parts. Thus, overlapped description thereof has been omitted here.

Embodiment

A cylindrical bandage according to an embodiment of the present invention is described with reference to FIGS. 2A to 8 mainly. As the cylindrical bandages embodying the present invention, a lower limb supporter is essentially similar to an upper limb supporter. As one embodiment of the present embodiment, a cylindrical bandage worn on a lower limb including a leg and a foot of a human body is described below.

A cylindrical bandage 1 of the present embodiment includes a tubular knit M and a gutter-shaped knit N extending from the top of the tubular knit M. The tubular knit M has one lengthwise end T and the other lengthwise end R and W. The gutter-shaped knit N has a cut-out section with a horseshoe or V shape. This gutter-shaped knit N is not of a circular cross-section.

The cylindrical bandage 1 has an inner surface with inside ribs in which an elastic yarn B with higher elasticity than a base yarn A hides behind the base yarn A, viewed from the cross-section perpendicular to the length direction of a leg or an arm wearing the cylindrical bandage 1. This allows the elastic yarn to avoid contact with the skin of a user.

The cylindrical bandage 1, which is of a length corresponding that of a leg or an arm, includes the tubular knit M extending from the end of the tubular knit M. The gutter-shaped knit N is shorter in a circumference direction than the tubular knit M and is formed into a gutter shape. That is, the gutter-shaped knit N has a cut-out section with a horseshoe or V shape and is of a horseshoe or C shaped cross-section.

The cylindrical bandage 1 is designed in accordance with personal data as shown in FIGS. 2A, 2B, and 2C.

The tubular knit M of the cylindrical bandage 1 according to the present embodiment covers a leg ranging from a foot excluding toes to a thigh as a lower limb supporter (a long supporter). The cylindrical bandage 1 as a lower limb supporter may be used singly; it may be worn on a right leg or a left leg. Alternatively, it may be used in combination; it may be worn on both legs.

Since the cylindrical bandage 1 according to the present embodiment includes the gutter-shaped knit N contiguous with the tubular knit M, the cylindrical bandage 1 for a right leg and the cylindrical bandage 1 for a left leg are distinguished from each other.

The tubular knit M, which has a lengthwise first end Q contiguous with the gutter-shaped knit N and a lengthwise second end T, is of a length corresponding that of a leg. The lengthwise second end T or its cross-section perpendicular to the length direction of a leg is disposed on a foot part corresponding to metatarsal bones mt ranging from cuneiform bones to intermediate phalanges. The position of part of the end T may be out of the metatarsal bones mt.

The end T disposed on the bottom of a leg may not be on an edge like ready-made socks. The cylindrical bandage 1 is preferably required to be kept from sliding. The tubular knit M embodying the present invention corresponds to the upper part of the human body position date L7 or a heel included in the human body position date L7.

The lengthwise second end T of the tubular knit M, which is of a length corresponding that of a leg, or its cross-section perpendicular to the length direction of a leg is disposed on a foot part corresponding to metatarsal bones mt ranging of intermediate phalanges. The lengthwise second end T of the tubular knit M, which is of a length corresponding that of an arm, or its cross-section perpendicular to the length direction of an arm, is disposed on an arm part corresponding to metacarpal bones mc ranging of proximal phalanges Pr and Ph.

The cylindrical bandage 1 according to the present embodiment includes the gutter-shaped knit N contiguous with the tubular knit M, which is of a length corresponding to that of a leg or an arm.

The cylindrical bandage 1 worn on the leg of a human body is described below as one embodiment.

A cylindrical bandage 1 worn on the upper arm of a human body, as another embodiment of the present invention is similar to a cylindrical bandage 1 worn on the leg of a human body as the present embodiment of the invention. The differences between them will be described if necessary.

Figure 3A:
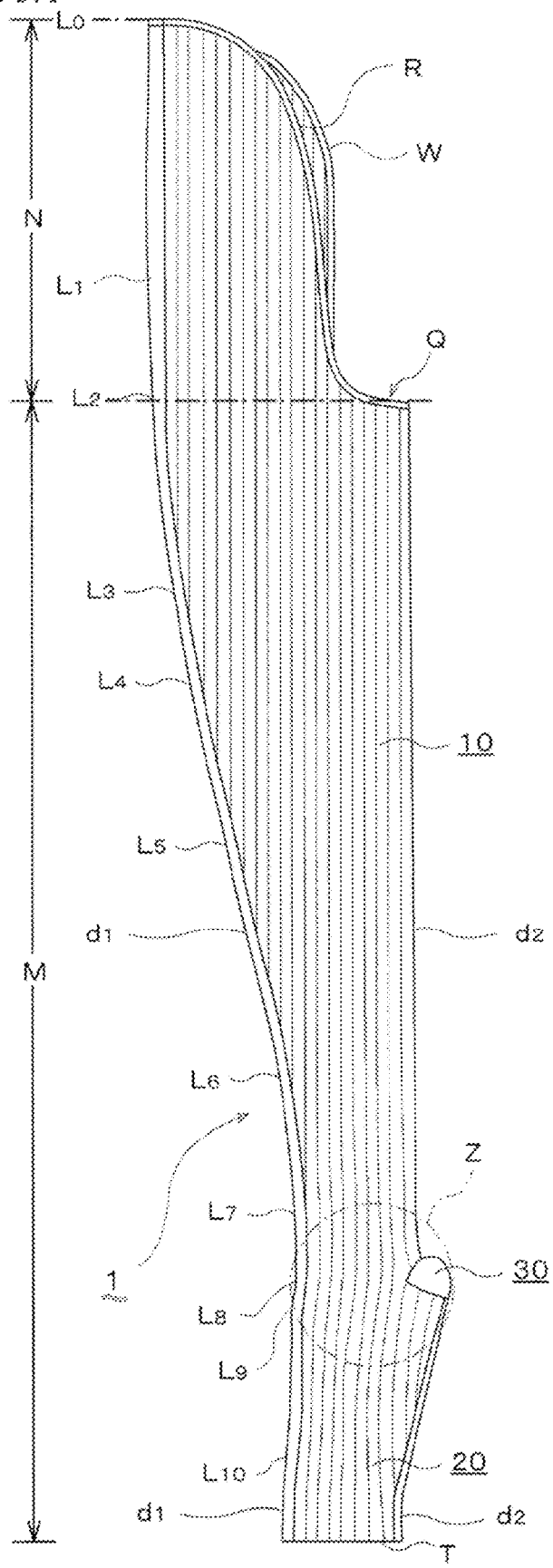
FIG. 3A shows a cylindrical bandage according to an embodiment of the present invention in which the instep of a foot and the shin of a leg correspond to front.
Figure 3B:
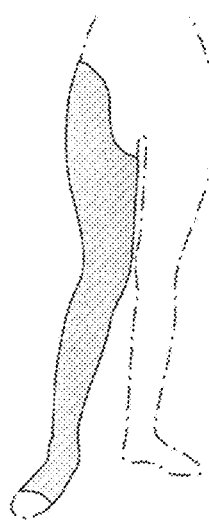
FIG. 3B shows the cylindrical bandage worn on a body part.

As shown in FIGS. 3A and 3B, the cylindrical bandage 1 of the present embodiment includes a first tubular knit 10 for covering the almost foot of a human body, a second tubular knit 20 for covering the almost leg of the human body, and a heel knit 30 for covering the heel of the human body. The second tubular knit 20 is contiguous with the first tubular knit 10. The heel knit 30 lies between the first tubular knit 10 and the second tubular knit 20 to fit the shapes of the heel.

These first tubular knit 10, second tubular knit 20 and heel knit 30 form the tubular knit M.

In some embodiments, the tubular knit M may be formed of only first tubular knit 10, or only the first tubular knit 10 and the second tubular knit 20. The heel knit 30 may be omitted as required. However, the presence of the heel knit 30 allows more stably staying of the cylindrical bandage 1 described below.

As shown in FIGS. 2A and 2B and FIGS. 3A and 3B, the first tubular knit 10 and the second tubular knit 20 contiguous with it are knitted in accordance with human body position data L0, L1, L2, . . . in the length direction of a target body part and human body circumference data m0, m1, m2, . . . corresponding to one-to-one to the human body position data L0, L1, L2, . . . .

Although the knitted fabric LM of the gutter-shaped knit N is gradually narrower to the one end corresponding to the human body circumference data m0, which represents the circumference of the human body position data L0, the tubular knit M, which is of a length corresponding to that of a leg or an arm, bears the gutter-shaped knit N. Thus, the human body position data L0 and L1 and L2 and the human body circumference data m0 and m1 are used for knitting. The approximate tightening of the gutter-shaped knit N can be set using length data as the gutter-shaped knit N has rigidity.

In the present embodiment, the human body position data L0, L1, L2, . . . , for example, shown in following Table 1 and FIGS. 2A, 2B, and 2C is determined as positions to be measured. Such measurement positions may be determined in accordance with the purpose of use of the cylindrical bandage 1 (for example, which may be used for prevention or therapy of lymphedema or lower limb varicose vein), types of the cylindrical bandage 1 (for example, which is used as, a supporter, a sleeve, a stocking, a glove, or an underwear), or a body part wearing the cylindrical bandage 1 (for example, which is worn on an arm, a leg, a head, a foot, a hand, or a wrist and puts pressure on them). The circumferences or the cross-section perimeters of the positions so determined are then measured.

Thus, the human body position data L0, L1, L2, . . . is determined and the circumferences of the human body position data L0, L1, L2, . . . so determined are measured. The human body circumference data m0, m1, m2, . . . , represents the circumferences or the thickness of the human body position data L0, L1, L2, . . . in the length direction of a human body such as a leg or an arm and corresponds one-to-one to the human body position data L0, L1, L2, . . . .

The human body position data L0, L1, L2, . . . as measurement positions is typically set to body parts having the varying shapes or the preceding or following part of the body parts.

In the present embodiment, as shown in FIGS. 2A, 2B, and 2C, a leg ranging from a position L0 near a groin to a position L10 corresponding to the position of the base of a little toe is measured to knit the cylindrical bandage 1 (a supporter for a lower limb) that is worn on the leg ranging from a foot excluding a toe to a thigh.

FIGS. 2A, 2B, and 2C shows the human body position data L0, L1, L2, . . . , L9, and L10 as measurement positions used for knitting of the cylindrical bandage 1 of the present embodiment. This cylindrical bandage 1 having one end W and R is worn on a leg and part of a foot.

Table 1 shows measurement values of the human body circumference data m0, m1, m2, . . . m9, and m10 corresponding one-to-one to of the human body position data L0, L1, L2, . . . , L9, L10, which ranges in length from a leg (an inside leg) and a foot excluding a toe of a human body. This measurement data is used as one example to knit the first cylindrical knit 10 and the second cylindrical knit 20 of the present embodiment.

The measurement values shown in Table 1 are the circumference of a human body. These measurement values are not directly related to elasticity.

TABLE 1

| | Human body position date | | | | | | | | | |
|---|---|---|---|---|---|---|---|---|---|---|
| | $L_1$ | $L_2$ | $L_3$ | $L_4$ | $L_5$ | $L_6$ | $L_7$ | $L_8$ | $L_9$ | $L_{10}$ |
| Human body circumference date | $m_1$ 52 | $m_2$ 47 | $m_3$ 36 | $m_4$ 34 | $m_5$ 35 | $m_6$ 28 | $m_7$ 22 | $m_8$ 30 | $m_9$ 22 | $m_{10}$ 22 |

As shown in FIGS. 2A, 2B, and 2C, the human body circumference data m0 is the circumference of a position L0 that is at the pelvis of a human body or is above and 3 to 5 cm distant from the top end of the pelvis. According to the embodiment shown in Table 1, this human body circumference data m0 is 61 cm. The human body circumference data m1 is the circumference of a position L1 that is below and 5 cm distant from a point a (a1) that is at the end of the bulge in the buttock of the human body. According to the embodiment shown in Table 1, this human body circumference data m1, which represents the circumference of the human body position data L1, is 52 cm.

The human body circumference data m2 is the circumference of a position L2 that is at the middle between the point a (a1) and a position L3 that is at the flexion of a knee. This human body circumference data m2, which represents the circumference of the human body position data L2, is 47 cm.

The human body circumference data m3 is the circumference of a position L3 that is at the flexion of the knee. This human body circumference data m3, which represents the circumference of the human body position data L3, is 36 cm.

The human body circumference data m4 is the circumference of a position L4 that is at a fibular head. This human body circumference date m4, which represents the circumference of the human body position date L4, is 34 cm.

The human body circumference date $m_5$ is the circumference of a position $L_5$ that is the thickest part of a carf. This human body circumference date $m_5$, which represents the circumference of the human body position date $L_5$, is 35 cm.

The human body circumference date $m_6$ is the circumference of a position $L_6$ that is at the lower end part of the carf. This human body circumference date $m_6$, which represents the circumference of the human body position date $L_6$, is 28 cm.

The human body circumference date $m_7$ is the circumference of a position $L_7$ that is at the thinnest part of an ankle. This human body circumference date $m_7$, which represents the circumference of the human body position date $L_7$, is 22 cm.

The human body circumference date $m_8$ is the circumference of a position $L_8$ that is between an instep and a heel. This human body circumference date $m_8$, which represents the circumference of the human body position date $L_8$, is 30 cm.

The human body circumference date $m_9$ is the circumference of a position $L_9$ that is at an arch. This human body circumference date $m_9$, which represents the circumference of the human body position date $L_9$, is 22 cm.

The human body circumference date $m_{10}$ is the circumference of a position $L_{10}$ that is at the base of a little toe. This human body circumference date $m_{10}$, which represents the circumference of the human body position date $L_{10}$, is 22 cm.

This date of the embodiment shown in Table 1 is the measurement date of a patient with lower leg lymphedema. The human body circumference date may be measured in units of millimeter.

Thus, the he human body position date $L_0, L_1, L_2, \ldots$ and the human body circumference date $m_0, m_1, m_2, \ldots$ are determined. The human body circumference date $m_0, m_1, m_2, \ldots$ is used to determine the number of the consecutive knitting loops of a row or the number of wales of one unit. The horizontal rows of loops in knitted fabric LM are called courses while vertical columns of loops in knitted fabric LM are called wale. That is, the courses are the series of intermeshing loops in a vertical direction while the wales are the widthwise inter-connected loops. The number of courses running widthwise determines the length of the knitted fabric LM while the number of wales running lengthwise determines the width or circumference of the knitted fabric LM.

In the first tubular knit 10 and the second tubular knit 20 of the tubular knit M of the cylindrical bandage 1 according to the present embodiment, the number of wales of each row or the number of stitches of each row is estimated using the human body circumference date $m_0, m_1, m_2, \ldots$ corresponding one-to-one to the human body position date $L_0, L_1, L_2, \ldots$ . It is note that the number of wales of each row is calculated to reflect Young's modulus or elasticity determined in accordance with the human body position date $L_0, L_1, L_2, \ldots$ . The number of wales of each row is set to the calculated value or its approximation, which is calculated based on the human body circumference date $m_0, m_1, m_2, \ldots$ and Young's modulus.

Thus, the varying circumferences between the human body circumference date $m_0, m_1, m_2, \ldots$ corresponding one-to-one to the human body position date $L_0, L_1, L_2, \ldots$ is represented as the varying numbers of wales.

The human body circumference date $m_0, m_1, m_2, \ldots$ corresponding one-to-one to the human body position date $L_0, L_1, L_2, \ldots$, which is determined in accordance with a target body part to be worn or the purpose of use, is measured to determine the number of wales or the circumference of the first tubular knit 10 and the second tubular knit 20.

In one embodiment, the human body position date $L_0$, $L_1$, $L_2$, ... and the human body circumference date $m_0$, $m_1$, $m_2$, ... that is provided by medical institutions may be used. The human body circumference date $m_0$, $m_1$, $m_2$, ... represents dimensions, specifically, the circumferences of each body part. The measurement unit of the circumferences may be centimeter or millimeter. The dimensions of the cylindrical bandage 1 are determined using the human body position date $L_0$, $L_1$, $L_2$, ... in the longitudinal or vertical direction of a target body part and the human body circumference date $m_0$, $m_1$, $m_2$, ... corresponding one-to-one to the human body position date $L_0$, $L_1$, $L_2$, ....

The human body circumference date $m_0$, $m_1$, $m_2$, ..., which correspond one-to-one to the human body position date $L_0$, $L_1$, $L_2$, ... in the longitudinal or vertical direction of a body part, represents measured original dimensions of a body part. Each human body circumference date $m_0$, $m_1$, $m_2$, ... represents the circumference of each human body position date $L_0$, $L_1$, $L_2$, ....

The human body position date $L_0$, $L_1$, $L_2$, ... represents predetermined positions of a body part to be coated with the cylindrical bandage 1. The human body circumference date $m_0$, $m_1$, $m_2$, ... is used to calculate the number of stitches of each row. The human body circumference date $m_0$, $m_1$, $m_2$, ... represent original measurements.

The number of stitches is estimated using the measured human body circumference date $m_0$, $m_1$, $m_2$, .... It is noted that the number of stitches is estimated to reflect Young's modulus or elasticity in accordance with the human body position date $L_0$, $L_1$, $L_2$ .... Digits after decimal points of the calculated value for determining the number of stitches may be rounded off, down, or up, the choice of which may be determined by the knitting yarn properties or application use of the cylindrical bandage 1.

The Young's modulus determining predetermined elasticity for each human body position date $L_0$, $L_1$, $L_2$, ... is determined by referring to the physical property of yarns used in knitting, knitting method, or stitch density.

The number of stitches of each row or the number of wales of each row is estimated using the human body circumference date $m_0$, $m_1$, $m_2$, ... and Young's modulus, which is determined in accordance with each human body position date $L_0$, $L_1$, $L_2$ .... The number of stitches is set to calculation or its approximation based on the human body circumference date $m_0$, $m_1$, $m_2$, ... and Young's modulus.

Young's modulus (E) is given by:

$$E=(F/S)/(\Delta P/P)$$

in which cross-section area formed of horizontal rows of loops is S, force exerted on the cross-section area S is F, the amount by which the length or width changes is $\Delta P$, and the original length or width is P.

Young's modulus can represent elasticity. In some body parts, user's feeling and compression on the body parts do not necessarily correspond to Young's modulus. Herein, Young's modulus is represented as elasticity.

The cross-section area S formed of horizontal rows of loops depends on the physical property of yarns used in knitting and knitting method. The force F exerted on the cross-section area S depends on each human body position date $L_0$, $L_1$, $L_2$ .... When the force F exerted on the cross-section area S formed of horizontal rows of loops is desired to be constant everywhere, F/S is fixed. In this case, elasticity or Young's modulus is consistent across the human body position date $L_0$, $L_1$, $L_2$ .... Consequently, pressure is not applied to only a certain part in the longitudinal direction of user's human body and uniform compression is provided to the user. Discomfort that could be felt by the user is eliminated. Alternatively, the force F exerted on the cross-section area S may vary in accordance with the human body position date $L_0$, $L_1$, $L_2$ .... The degrees of compression may vary in accordance with the positions. For example, compression may be highest at an ankle and progressively decrease towards a thigh. This may increase in venous return further.

Thus, elasticity or Young's is determined in accordance human body position date $L_0$, $L_1$, $L_2$ .... The number of wales is estimated using the elasticity or Young's modulus and the human body circumference date $m_0$, $m_1$, $m_2$, ..., which represents varying cross-sections or varying circumferences. The calculation based on the elasticity or Young's modulus and the human body circumference date $m_0$, $m_1$, $m_2$, ... corresponding one-to-one to the human body position date $L_0$, $L_1$, $L_2$, ... in the longitudinal or vertical direction of a body part, is represented as the number of the stitches or the number of the wales. Thus, the human body circumference date $m_0$, $m_1$, $m_2$, ... and elasticity or Young's modulus, which is determined in accordance with the human body position date $L_0$, $L_1$, $L_2$, ..., are used to calculate the number of the wales.

The first tubular knit 10 and the second tubular knit 20 of the cylindrical bandage 1 including the tubular knit M and the gutter-shaped knit N according to the present embodiment is constructed using the human body position date $L_0$, $L_1$, $L_2$, ... in the longitudinal or vertical direction of a target body part and the human body circumference date $m_0$, $m_1$, $m_2$, ... corresponding one-to-one to the human body position date $L_0$, $L_1$, $L_2$, .... In knitting of the first tubular knit 10 and the second tubular knit 20, the number of wales is set to approximation of calculation using the human body circumference date $m_0$, $m_1$, $m_2$, ... and elasticity (Young's modulus), which is determined in accordance with the human body position date $L_0$, $L_1$, $L_2$, .... Thus, the human body circumference date $m_0$, $m_1$, $m_2$, ..., which represents the varying circumferences, is reflected in the number of wales.

The tubular knit M and the gutter-shaped knit N according to the present embodiment have the varying numbers of stitches to correspond to the varying cross-sections of a target body part or the human body circumference date $m_0$, $m_1$, $m_2$, ... corresponding one-to-one to the human body position date $L_0$, $L_1$, $L_2$, ... in the length of a leg including a foot. The circumferences of the tubular knit M and the gutter-shaped knit N vary across the length direction of the target body part by varying the number of stitches.

Thus, in the cylindrical bandage 1 according to the present embodiment, the number of wales of the tubular knit M and the gutter-shaped knit N is set to approximation of calculation using the human body circumference date $m_0$, $m_1$, $m_2$, ... corresponding one-to-one to the human body position date $L_0$, $L_1$, $L_2$, ... and elasticity (Young's modulus), which is determined in accordance with the human body position date $L_0$, $L_1$, $L_2$, .... The number of the stitches or knitted width varies across the length. Overall shapes or dimensions depend on the varying numbers of stitches or the varying knitted widths.

The circumferences of the cylindrical bandage 1 varies with the numbers of stitches. This allows control of compression. This cylindrical bandage 1 provides predetermined compression even though the cross-section of target body part varies across its length. It is easy to provide desired compression corresponding to each human body position date $L_1$, $L_2$, $L_3$, ... or the varying cross-sections of the body part.

Compression can be controlled by changing stitch density, knitting method, yarn physical property, or elasticity (Young's modulus) in addition to the number of stitches. Compression may be fixed or vary across the longitudinal direction.

The number of courses, which is the series of intermeshing loops, is determined in accordance with the length between the human body position date $L_1, L_2, L_3, \ldots$ and by referring to yarn physical property, knitting method, or stitch density.

The ankle part, which is the border between the leg and the foot and corresponds to the human body position date $L_7$ and $L_8$, includes the heel and the malleolus. This ankle part has large varying cross-sections or large varying circumferences, as can be seen from the human body circumference date $m_8$, which represents the circumference of a part including the instep and the heel. In particular, a patient with vein disorders or lymphedema has the localized ankle part with larger varying circumferences. The circumferences vary largely from the human body circumference date $m_7$ corresponding to the human body position date $L_7$ that is at the ankle to the human body circumference date $m_9$ corresponding to the human body position date $L_9$ that is at the arch.

The cylindrical bandage 1 according to the present invention includes the tubular knit M having the varying circumferences resulting from the varying numbers of the wales. The wale stitch numbers of the first tubular knit 10 approximate the calculations based on the human body circumference date $m_0, m_1, m_2, \ldots m_6$, and $m_7$ corresponding one-to-one to the human body position date $L_0, L_1, L_2, \ldots L_6$, and $L_7$ and Young's modulus determined in accordance with the position of the human body position date $L_0, L_1, L_2 \ldots$. The wale stitch numbers of the second tubular knit 20 approximate the calculations based on the human body circumference date $m_9$ and $m_{10}$ corresponding one-to-one to the human body position date $L_9$ and $L_{10}$ and Young's modulus determined in accordance with the position of the human body position date $L_9$ and $L_{10}$.

In the tubular knit M, the number of the wales of the top end of the second tubular knit 20 contiguous with the first tubular knit 10 is larger than that of the bottom end of the first tubular knit 10. Consequently, the width 12 of the top end of the second tubular knit 20 is wider than the width 11 of the bottom end of the first tubular knit 10 (referring to FIGS. 5, 6A and 6B). With the difference in the number of wales, the tube diameter or the circumference of the top end of the second tubular knit 20 is larger than the bottom end of the first tubular knit 10 (referring to FIGS. 5, 6A and 6B).

Alternatively, the wales of the bottom end of the first tubular knit 10 and the wales of the top end of the second tubular knit 20 may be the same number. In this case, the width $l_1$ of the bottom end of the first tubular knit 10 and the width $l_2$ of the top end of the second tubular knit 20 contiguous with the bottom end of the first tubular knit 10 is the same. That is, the bottom end of the first tubular knit 10 and the top end of the second tubular knit 20 are the same tube diameter or circumference, which is the circumference of one circle formed of the wale knitting loops.

Thus, in some embodiments, the bottom end of the first tubular knit 10 may be in line with the top end of the second tubular knit 20 and the heel knit 30 could be eliminated in the tubular knit M.

Figure 5:
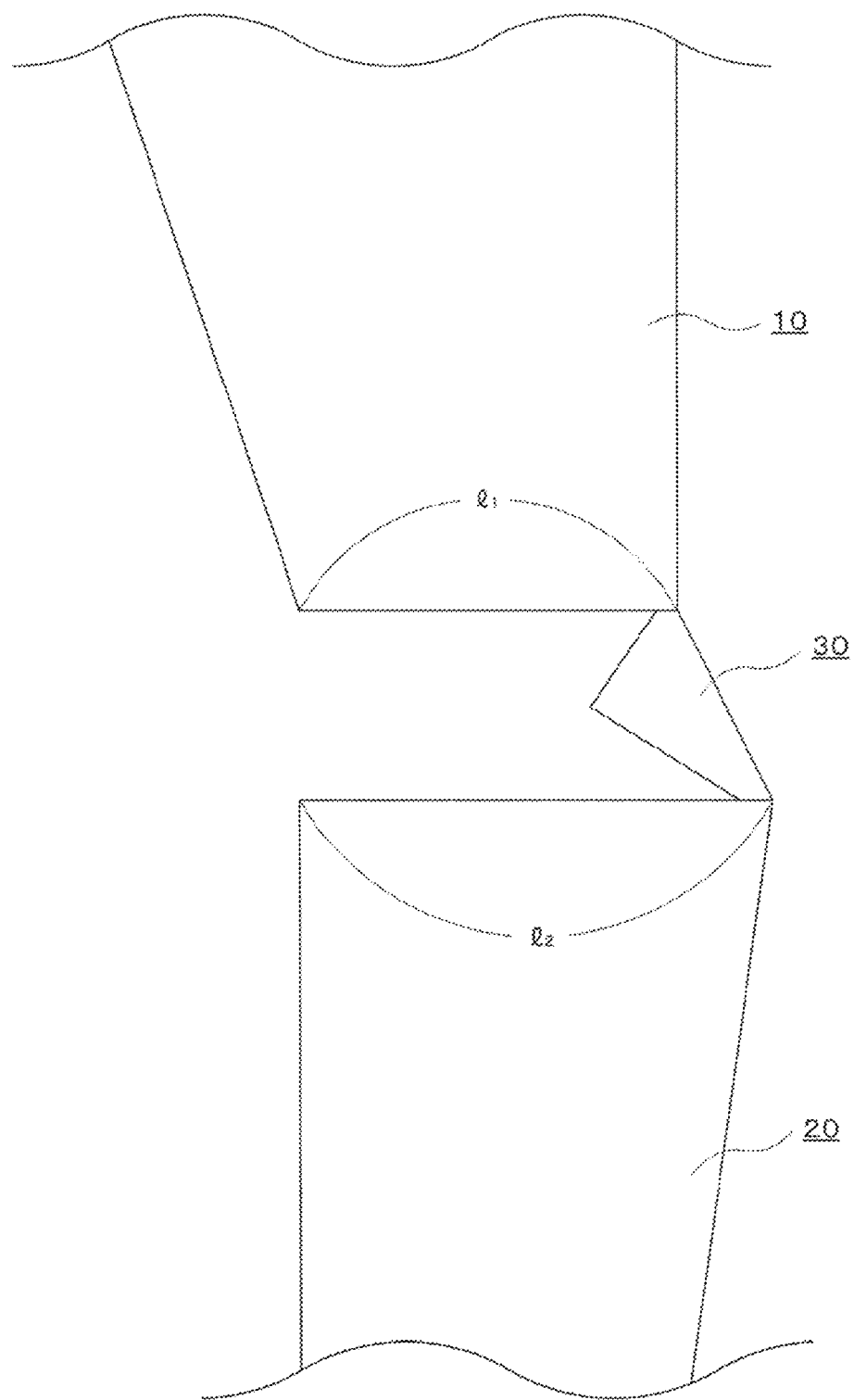
FIG. 5 schematically illustrates the knitting area of a heel knit of the cylindrical bandage according to an embodiment of the present invention.

Referring to FIG. 5, the stitches of the bottom end row of the first tubular knit 10 may be as many as those of the top end row of the tubular knit 20. In this case, the width $l_1$ of the bottom end of the first tubular knit 10 and the width $l_2$ of the top end of the second tubular knit 20 contiguous with the bottom end of the first tubular knit 10 are the same.

In the present embodiment, the heel knit 30 having predetermined courses is disposed between part of the bottom end of the first tubular knit 10 and part of the top end of the second tubular knit 20. The top end row of the second tubular knit 20 has a larger circumference than the bottom end row of the first tubular knit 10 has. Thus, part of the bottom end row of the first tubular knit 10 and part of the top end row of the second tubular knit 20 are connected via the heel knit 30.

It is preferable that the tubular knit M include the heel knit 30 between the first tubular knit 10 and the second tubular knit 20 to eliminated slip of the cylindrical bandage 1. That is, the cylindrical bandage 1 having the heel knit 30 fitting shapes of heel stays on a target body more stably. In some embodiments, the heel knit 30 could be eliminated.

With a sharp increase in the number of wales in the part corresponding to an ankle part between a leg and a foot, or short courses between the bottom end of the first tubular knit 10 and the top end of the second tubular knit 20, the tubular knit M would wrinkle at the back of the ankle and be tense at the corner of the heel. In this case, the knitted fabric LM may fail to make in close contact with the lower part around the malleolus of a human body and put pressure on the lower part.

With a gradual increase in the number of wales in the part corresponding to an ankle part between a leg and a foot, or longer courses between the bottom end of the first tubular knit 10 and the top end of the second tubular knit 20, the tubular knit M may fail to fit around an ankle joint and may have looseness and wrinkles, which may cut into a skin and cause compression concentration.

In the cylindrical bandage 1 according to the present embodiment, the stitches of the bottom end row of the first tubular knit 10 partially intermesh with the stitches of the top end row of the second tubular knit 20. The remaining stitches of the bottom end row of the first tubular knit 10 is connected with the stitches of the top end row of the second tubular knit 20 via the heel knit 30. The heel knit 30 closes the diameter or circumference gaps between the bottom end of the first tubular knit 10 and the top end of the second tubular knit 20.

Such a tubular knit M does not wrinkle easily on the back of the ankle and is not tense easily on the corner of the heel and thus fits tightly around ankle.

In some embodiments, the second tubular knit 20 may be constructed by using the calculation based on the human body circumference date $m_8$, which represents the circumference of a part including the instep and the heel, in addition to using the human body position date $L_9$ and $L_{10}$. That is, the second tubular knit 20 may be constructed by using the calculation based on the human body circumference date $m_8, m_9$, and $m_{10}$ corresponding one-to-one to the human body position date $L_8, L_9$, and $L_{10}$, and Young's modulus, which is determined in accordance with human body position date $L_8, L_9$, and $L_{10} \ldots$. The number of the wales of the second tubular knit 20 may be set to the approximation of calculation based on the human body circumference date $m_8, m_9, m_{10}$ and Young's modulus determined in accordance with the position of the human body position date $L_8, L_9$, and $L_{10} \ldots$. In this case, the heel knit 30 is disposed between the part of stitch row corresponding to the unit of the human body circumference date $m_7$ in the first tubular knit 10 and the part of stitch row corresponding to the unit of the human body circumference date $m_8$ in the second tubular knit 20. Even when the number of the wales of the second tubular knit 20 is set to the approximation of calculation based on the human body circumference date $m_8$, $m_9$, $m_{10}$ and Young's modulus determined in accordance with the position of the human body position date $L_8$, $L_9$, and $L_{10}$ . . . , there are difference in the number of the wales between the end corresponding to the unit of the human body circumference date $m_7$ of the first tubular knit 10 and the end corresponding to the unit of the human body circumference date $m_7$ of the second tubular knit 20. The number of wales corresponding to the human body circumference date $m_8$, which represents the circumference of the human body position date $L_8$, is more than wales corresponding to the human body circumference date $m_7$, which represents the circumference of the human body position date $L_8$ that is at the ankle part between a leg and a foot.

In this case, again, the width $l_2$ of the top end of the second tubular knit 20 contiguous with the bottom end of the first tubular knit 10 is wider than the width $l_1$ of the bottom end of the first tubular knit 10. That is, the top end of the second tubular knit 20 contiguous with the bottom end of the first tubular knit 10 has larger diameter or circumference than the bottom end of the first tubular knit 10 has.

Whereas, when the width $l_1$ of the bottom end of the first tubular knit 10 and the width $l_2$ of the top end of the second tubular knit 20 contiguous with the bottom end of the first tubular knit 10 is the same, the top end of the second tubular knit 20 contiguous with the bottom end of the first tubular knit 10 has the same diameter or circumference as the bottom end of the first tubular knit 10 has.

The gutter-shaped knit N is above the tubular knit M including the first tubular knit 10 and the second tubular knit 20 according to the present embodiment. When the tubular knit M has the first end corresponding to the human body position date $L_2$ having the human body circumference date $m_2$, the maximum length of the tubular knit M corresponds to the length between the human body position date $L_0$ and the human body position date $L_7$, the length between the human body position date $L_0$ and the human body position date $L_9$, or the length between the human body position date $L_0$ and the human body position date $L_{10}$. The number of wales of the tubular knit M is set to the approximation of the calculation based on the human body circumference date $m_0$, $m_1$, $m_2$ . . . .

The gutter-shaped knit N corresponds to the human body position date $L_0$ with the human body circumference date $m_0$ and the human body position date $L_1$ with the human body circumference date $m_1$. The human body position date $L_0$ is determined as an origin and following position date $L_2$ . . . is determined in accordance with the determination of the human body position date $L_0$. This makes the tubular knit M having the first end with large diameter or circumference. Thus, the determination of the human body position date $L_0$ is required to form the gutter-shaped knit N.

The gutter-shaped knit N extending from the first end of the tubular knit M, which is of a length corresponding to that of an arm or leg, has smaller length of the circumference direction than the first end of the tubular knit M and is formed into gutter shape. That is, the gutter-shaped knit N has the horseshoe or C shape in cross-section. This gutter-shaped knit N has a cut-out section with a horseshoe or V shape. The gutter-shaped knit N fitting shapes of belly and buttock stands on the tubular knit M. Thus, the elasticity or stiffness of the gutter-shaped knit N and the compression of the gutter-shaped knit N is not determined only by Young's modulus.

In the first tubular knit 10 and the second tubular knit 20 of the tubular knit M according to the present embodiment, the varying circumference date or the human body circumference date $m_0$, $m_1$, $m_2$, . . . $m_9$, and $m_{10}$ corresponding one-to-one to the human body position date $L_0$, $L_1$, $L_2$, . . . $L_9$, $L_{10}$ is reflected in the varying numbers of stitches. The first tubular knit 10, which is knitted in accordance with the human body circumference date $m_0$, $m_1$, $m_2$, . . . $m_6$, and $m_7$ corresponding one-to-one to the human body position date $L_0$, $L_1$, $L_2$, . . . $L_6$, and $L_7$, covers a leg mainly. When the circumference is largest at the thigh side and decreases towards the ankle side or the circumference decrease in order of the human body circumference date $m_0$, $m_1$, $m_2$, . . . $m_6$, and $m_7$, the number of the stitches of rows decreases in correspondence with in order of the human body circumference date $m_0$, $m_1$, $m_2$, . . . $m_6$, and $m_7$. In knitting, the difference in the number of stitches of rows between the human body position date $L_0$, $L_1$, $L_2$, . . . $L_6$, and $L_7$ gradually decreases. This provides uniform compression and comfortable fit.

The first tubular knit 20, which is knitted in accordance with the human body circumference date $m_8$, $m_9$, and $m_{10}$ corresponding one-to-one to the human body position date $L_8$, $L_9$, and $L_{10}$ or the human body circumference date $m_9$ and $m_{10}$ corresponding one-to-one to the human body position date $L_9$ and $L_{10}$, covers a foot mainly. When the circumference is largest at the ankle side and decreases towards the toes side or the circumference decrease in order of the human body circumference date $m_8$, $m_9$, and $m_{10}$, the number of the stitches of rows decreases in correspondence with in order of the human body circumference date $m_8$, $m_9$, and $m_{10}$. In knitting, the difference in the number of stitches of rows between the human body position date $L_8$, $L_9$, and $L_{10}$ gradually decreases. This provides uniform compression and comfortable fit.

The top or bottom end of the cylindrical bandage 1 is likely to be affected by an adjacent unit and stretched when is put on or taken off. Thus, the number of stitches of the top or bottom end of the cylindrical bandage 1 may be determined by referring to decrease in elasticity resulting from repetitive stretch.

The cylindrical bandage 1 includes the heel knit 30 disposed between the first tubular knit 10 and the second tubular knit 20. The heel knit 30 is knitted at predetermined courses. The heel knit 30 is joined to 40% or less of the circumference of the top end row of the second tubular knit 20 and is joined to 40% or less of the circumference of the bottom end row of the first tubular knit 10. It is note that the joint length of the heel knit 30 is longer for the top end of the second tubular knit 20 than for the bottom end of the first tubular knit 10.

The heel knit 30 is preferably joined to 10 to 40% of the knitted width of the top end row of the second tubular knit 20 and is joined to 10 to 40% of the knitted width of the lower end knit of the first tubular knit 10. The knitting loops of the heel knit 30 intermesh with part of the knitting loops the top end row of the second tubular knit 20 and part of the knitting loops of the bottom end row of the first tubular knit 10. Thus, the first tubular knit 10 and the second tubular knit 20 are connected by the heel knit 30. The heel knit 30 gives a predetermined angle between the first tubular knit 10 and the second tubular knit 20.

Figure 4A:
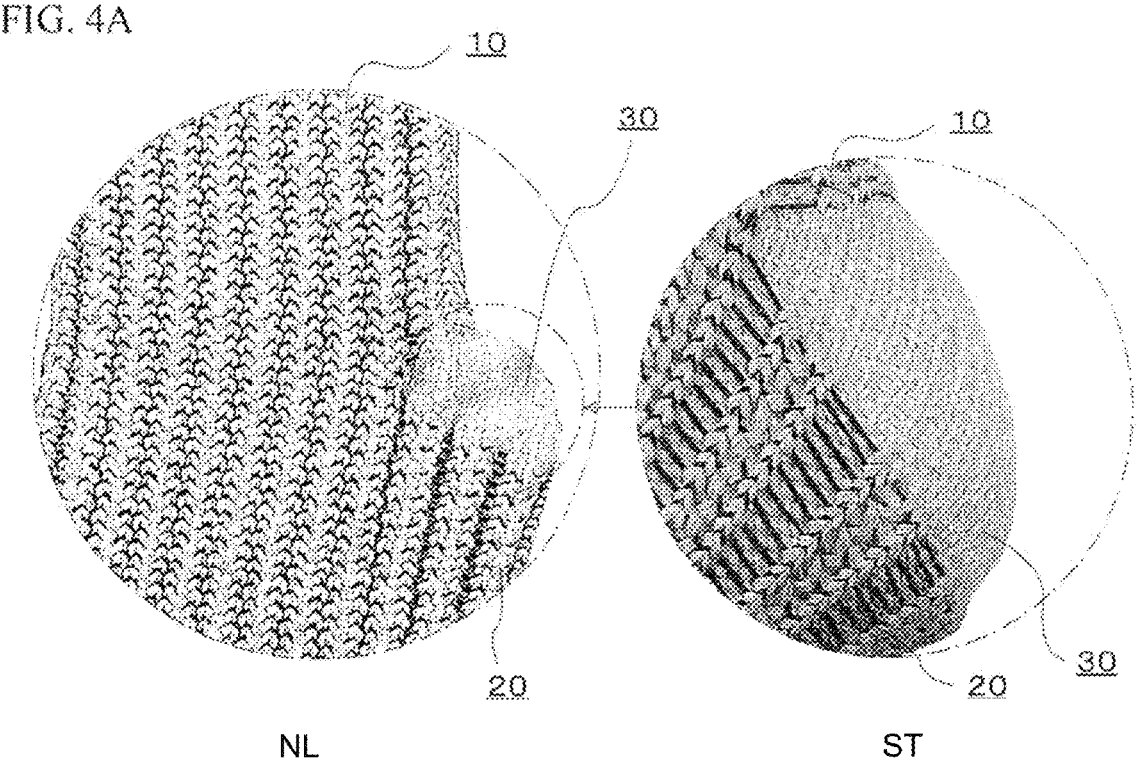
FIG. 4A is an enlarged photo of the main part Z of the cylindrical bandage according to the embodiment shown in FIG. 3.
Figure 4B:
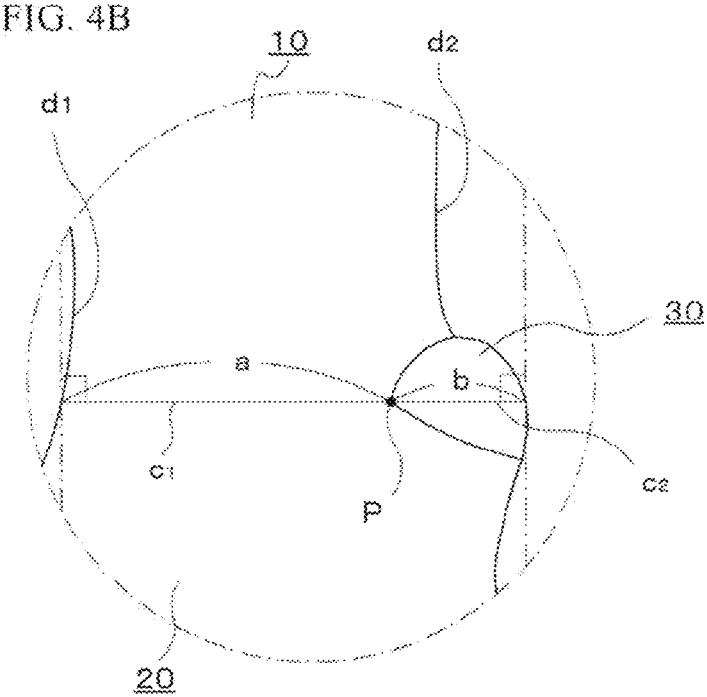
FIG. 4B is a schematic view illustrating the main part Z of the cylindrical bandage according to the embodiment shown in FIG. 3

The cylindrical bandage 1 according to the present embodiment includes the knitted fabric LM that are symmetric when viewed from the front as shown in FIGS. 6A, 6B, and 7, and 8. Herein, the front is the ventral side of the human body with the cylindrical bandage 1, back is the dorsal side of the human body with the cylindrical bandage 1, and left side and right side are between the front and the back. The cylindrical bandage 1 according to the present embodiment has the ratio of length a to length b in a range of 6:4 to 9:1 under conditions which is folded along a back symmetrical line d2 (a center line d2 in a back view of FIGS. 6A and 6B) and a front symmetrical line d1 (a center line d1 in a front view of FIGS. 6A and 6B). The length a is a length of a virtual perpendicular line c1 that connects between the front symmetrical line d1 and a border P between the first tubular knit 10, the second tubular knit 20, and the heel knit 30, as shown in FIGS. 6A to 8. The length b is a length of a virtual perpendicular line c2 that connects between the back symmetrical line d2 and the border P, as shown in FIGS. 6A to 8. It should be noted that the back symmetrical line d2 and the front symmetrical line d1 divide the circumference of the cylindrical bandage 1 into half. Further, the length is determined under normal condition NL where the cylindrical bandage 1 is not stretched. Furthermore, the virtual perpendicular line c1 and the virtual perpendicular line c2 are perpendicular to the longitudinal direction of the cylindrical bandage 1. In FIG. 4B, the perpendicular line c1 connects between the border P and the edge of the first tubular knit 10 or the second tubular knit 20, and the perpendicular line c2 connects between the border P and the edge of the heel knit 30.

Figure 6A:
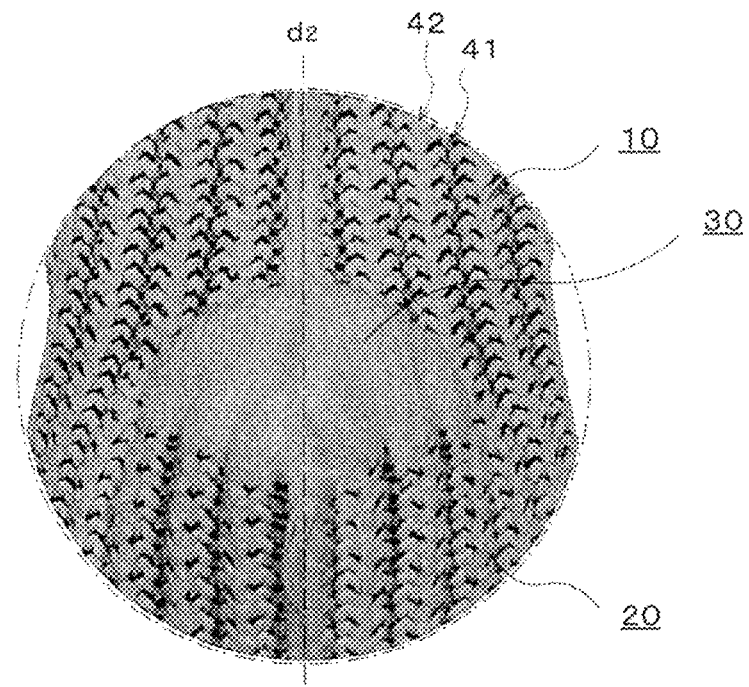
FIG. 6A is an enlarged photo of the main part Z of the cylindrical bandage according to the embodiment shown in FIG. 3.
Figure 6B:
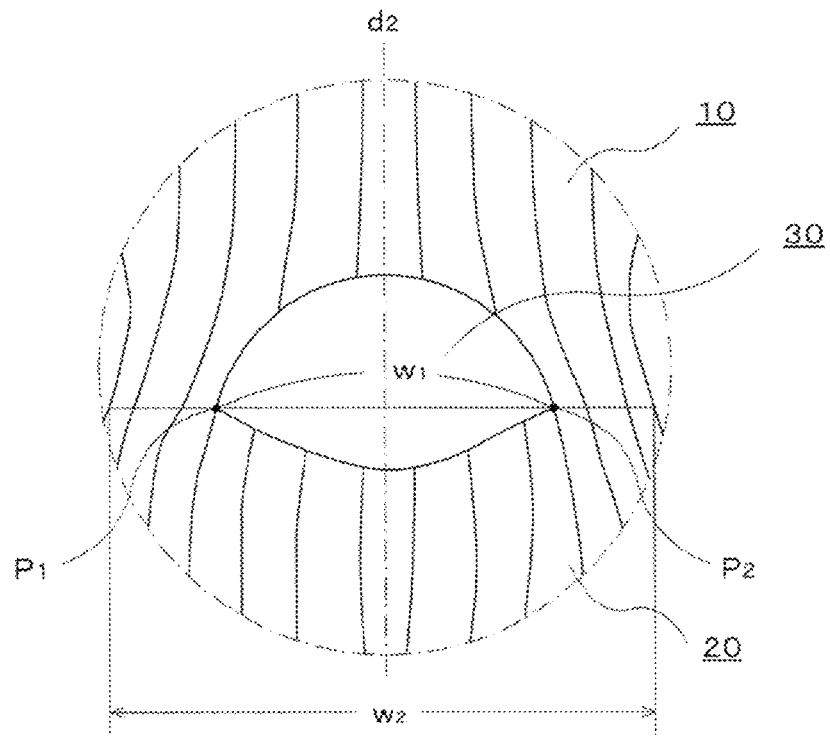
FIG. 6B is a schematic view illustrating the main part Z of the cylindrical bandage according to the embodiment shown in FIG. 3

Viewed from a different angle as shown in FIG. 4 6B, the cylindrical bandage 1 according to the present embodiment has a length w1 that is in a range of 10 to 90%, preferably, in a range of 20 to 80%, more preferably, in a range of 30 to 70% of a length w2 under conditions which is folded so that the symmetrical line d2 is positioned at center. The length w1 is the length of a virtual perpendicular line that connects between a border P1 and a border P2. The length w2 is the length of a virtual perpendicular that straightly extends from the virtual perpendicular line connecting between the border P1 and the border P2 to the edges of the first tubular knit 10 or the second tubular knit 20. The border P1 and the border P2 are between the first tubular knit 10, the second tubular knit 20, and the heel knit 30. It should be noted the cylindrical bandage 1 is folded along predetermined positions that divide the circumference of the cylindrical bandage 1 into half. Further, the length is determined under normal conditions NL where the cylindrical bandage 1 is not stretched.

Thus, in the cylindrical bandage 1 according to the present embodiment, the length $w_1$ between the border $P_1$ and the border $P_2$ is in a range of 10 to 90%, preferably, 20 to 80%, more preferably, 30 to 70% of a length $w_2$, which is the length of the virtual perpendicular line extending from the virtual perpendicular line connecting between the border $P_1$ and the border $P_2$ to the edges of the first tubular knit 10 or the second tubular knit 20, under conditions where the cylindrical bandage 1 is folded in half so that the symmetrical lines $d_1$ and $d_2$ are at center.

The cylindrical bandage 1 according to the present embodiment includes the heel knit 30 disposed between the first tubular knit 10 and the second tubular knit 20. This heel knit 30 is contiguous to 40% or less of the top end knitted width of the second tubular knit 20 and is contiguous to 40% or less of the bottom end knitted width of the first tubular knit 10. The heel knit 30 is knitted and have the predetermined number of courses. This cylindrical bandage 1 has the ratio of the length a to the length b in a range of 6:4 to 9:1 when folded along the back symmetrical line $d_2$ and the front symmetrical line $d_1$. The length a is the length of the virtual perpendicular line $c_1$ connecting between the front symmetrical line $d_1$ and the border P between the first tubular knit 10, the second tubular knit 20, and the heel knit 30. The length b is the length of the virtual perpendicular line $c_2$ connecting between the back symmetrical line $d_2$ and the border P.

Thus, the heel knit 30 with the predetermined number of courses is disposed between the first tubular knit 10 and the second tubular knit 20. This heel knit 30 is joined to 40% or less of the top end circumference of the second tubular knit 20 and is joined to 40% or less of the bottom end circumference of the first tubular knit 10. Thus, the cylindrical bandage 1 includes the heel knit 30 with a round or curve corresponding to a heel. The heel knit 30 is rounder or curvier than the first tubular knit 10 and the second tubular knit 20 and thus fits to a heel better when worn. The form of the heel knit 30 between the first tubular knit 10 and the second tubular knit 20 allows the cylindrical bandage 1 to have a tube diameter fitting an ankle circumference. Thus, this cylindrical bandage 1 is not loose fit at an ankle and tight fit at the corner of a heel. Consequently, the knitted fabric LM is not easily loose at or near malleolus, specifically, the back of a malleolus, and provides higher compression.

The first tubular knit 10 is contiguous to the top of the heel knit 30 and covers a leg while the second tubular knit 20 is contiguous to the bottom of the heel knit 30 and covers a foot when worn. The contiguous length of the heel knit 30, which corresponds to heel, is longer to the top end of the second tubular knit 20 than to the bottom end of the first tubular knit 10. This allows the cylindrical bandage 1 to fit around heel better. The cylindrical bandage 1 is not tight fit at the corner of a heel. The knitted fabric LM gets in closer contact with a malleolus and its surroundings.

The tubular knit M including the first tubular knit 10, the second tubular knit 20, and the heel knit 30 has the ratio of the length a to the length b in a range of 6:4 to 9:1 under conditions which is folded along the symmetrical line $d_2$ and the symmetrical line $d_1$. The length a is the length of the virtual perpendicular line $c_1$ connecting between the front symmetrical line $d_1$ and the border P between the first tubular knit 10, the second tubular knit 20, and the heel knit 30. The length b is the length of the virtual perpendicular line $c_2$ connecting between the back symmetrical line $d_2$ and the border P. The border P between the first tubular knit 10, the second tubular knit 20, and the heel knit 30 is positioned in the back. Thus, a round malleolus is covered with not the heel knit 30 with a round or curve but the first tubular knit 10 with a predetermined Young's modulus and the second tubular knit 20 with a predetermined Young's modulus, when the cylindrical bandage 1 is worn.

The cylindrical bandage 1 according to the present embodiment is not tense at a heel and loose at an instep when worn. The first tubular knit 10 and the second tubular knit 20 cover undulation parts corresponding to malleolus and its surroundings. Thus, the cylindrical bandage 1 allows the knitted fabric to get in close contact with the lower part around malleolus. Such a cylindrical bandage 1 provides uniform compression on the part around ankle stably.

The heel knit 30 is preferably joined to 10 to 40%, more preferably, 20 to 40% of the bottom end width $l_1$ of the first tubular knit 10 and is joined to 10 to 40%, more preferably, 20 to 40% of the top end width $l_2$ of the second tubular knit 20. Consequently, the first tubular knit 10 and the second tubular knit 20 are not tight at ankle and loose at the lower part around malleolus. The first tubular knit 10 and the second tubular knit 20 can get in close contact with undulation parts corresponding to malleolus and its surroundings and provide uniform compression on the undulation parts.

The heel knit 30 between the first tubular knit 10 and the second tubular knit 20 according to the present embodiment has increase and decrease in the knitted width and the varying positions of the ends of the rows or the varying numbers of stitches. Such a heel knit 30 has a larger curvature to fit the curve shapes of a heel. Consequently, the first tubular knit 10 and the second tubular knit 20 is less likely to be pulled towards a heel part.

Figure 9:
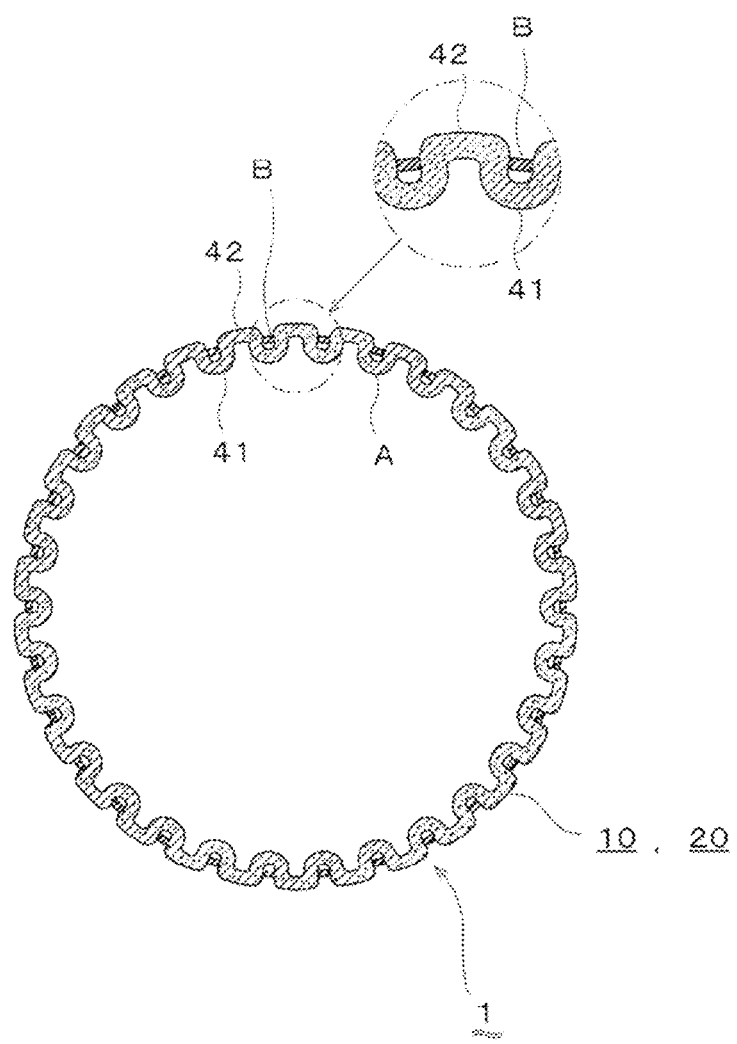
FIG. 9 is a cross-sectional view illustrating ribs and grooves of a tubular knit of the cylindrical bandage according to an embodiment of the present invention.

In the cylindrical bandage 1 according to the present embodiment, at least the first tubular knit 10 and the second tubular knit 20 have a base structure including rib stitches or tuck stitches. As shown in FIG. 9, the cylindrical bandage 1 has the rib structure with alternate plain and purl stitches of the base yarn A. Such a cylindrical bandage 1 has alternate raised stitches and fallen stitches in the circumferential direction. The plain and purl stitches run longitudinally.

This rib knitting of the first tubular knit 10 and the second tubular knit 20 makes the both surfaces having alternate ribs and grooves in the circumferential direction. Additionally, the ribs and grooves extend longitudinally. Thus, as shown in FIG. 9, Thus, the first tubular knit 10 and the second tubular knit 20 have the both surfaces with alternate ribs and grooves running lengthwise. These first tubular knit 10 and second tubular knit 20 have a waveform or a corrugation in cross-section as shown in FIG. 9. The raised stitches on the face appear as recesses on the back while the raised stitches on the back appear as recesses on the face. That is, the rib stitches on the outer surface appear as recesses on the inner surface while the rib stitches on the inner surface of appear as the recesses on the inner surface.

Inner protuberances 41 alternate with outer protuberances 42 in the circumferential direction. The inner protuberances 41 are the stitches that appear as the raised lines on the inner surface, which will directly contact with a user, and as the recess lines on the outer surface. The outer protuberances 42 are the stitches that appear as the raised lines on the outer surface and as the recess lines on the inner surface. In the inner surface, which will directly contact with a user, the inner protuberances 41 run side by side with the outer protuberances 42 therebetween. These inner protuberances 41 and outer protuberances 42 extend longitudinally.

Thus, the cylindrical bandage 1 including the tubular knit M and the gutter-shaped knit N has the inner protuberances 41 that appear as the raised lines on the inner surface, which will directly contact with a user, and extend lengthwise in parallel with each other. Such inner protuberances 41 allow provision of deep compression to the use's skin. The rib structure having the inner protuberances 41 and the outer protuberances 42 provides varying degrees of compression or tightening force in the circumferential direction. In particular, the inner protuberances 41 provide a series of compression along the longitudinal direction of the cylindrical bandage 1. That is, the rib structure provides balanced and distributed compression in the circumferential direction and lengthwise consecutive compression along the flow direction of lymph and venous. Such a rib structure allows increase in lymph flow or venous return. Additionally, the rib structure provides massage or drainage effect. This enables relax or loose of skin and muscle or improvement of organic tissue thickening.

Further, the knitted fabric LM having the inner surface with ribs and grooves can get in pressure contact with even a curvy part such as a heel.

Figure 10A:
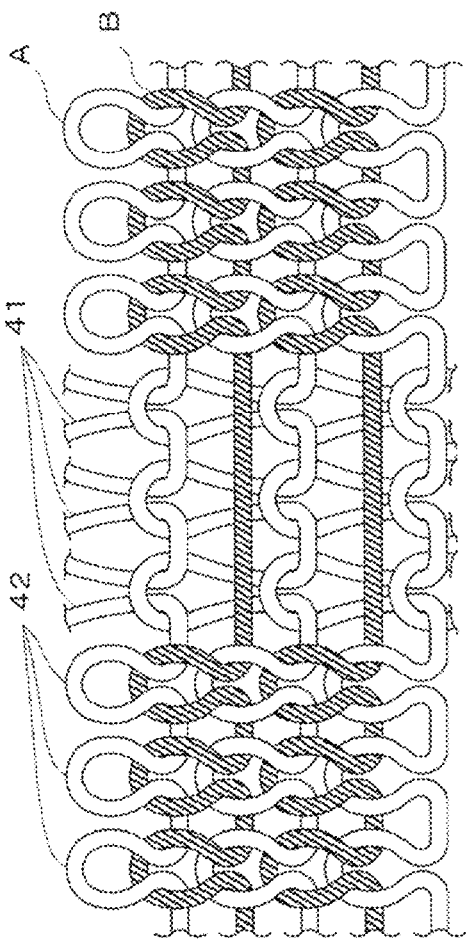
FIG. 10A is an enlarged view illustrating stitches of a first tubular knit and a second tubular knit of the cylindrical bandage according to an embodiment of the present invention.

The cylindrical bandage 1 according to the present embodiment has the base structure with ribs and grooves as shown in FIG. 10A. This structure includes the rib stitches of a base yarn A and the stitches of an elastic yarn B, which has higher elasticity than the base yarn A has. The stitch row of the elastic yarn B alternates with the stitch row of the base yarn A. Specifically, the outer protuberances 42 of the rib structure with the rib stitches of the base yarn A has knit stitch of the elastic yarn B while the inner protuberances 41 of the rib structure with rib stitches of the base yarn A has tuck or miss (non-knit) stitch of the elastic yarn B. The knit stitches alternate with the miss or tuck stitches.

Thus, in the cylindrical bandage 1 according to the present embodiment, The knitted stitches (plain stitches) of the outer protuberances 42 in the rugged base structure such as rib structure includes the knitted stitches of the elastic yarn B while the knitted stitches (purl stitches) of the inner protuberances 41 in the rugged base structure such as rib structure includes tuck or miss (non-knit) stitches of the elastic yarn B. This minimizes exposure of the elastic yarn B on the inner surface, which will get in directly contact with a user's skin, especially, on the inner protuberances 41 in the inner surface of the cylindrical bandage 1. Thus, the elastic yarn B is allowed to avoid contact with a user's skin. The cylindrical bandage 1 is not likely to cause irritation, allergy, and eczema derived from material, elasticity, rub, or other characteristics of the elastic yarn B and thus provides good texture.

The use of the elastic yarn B in the rib structure, in which the raised lines and recess lines extend in lengthwise direction, increase elasticity in the wale and the course of the first tubular knit 10 and the second tubular knit 20. Additionally, the use of the elastic yarn B increases tension and compression of the first tubular knit 10 and the second tubular knit 20.

In particular, the first tubular knit 10 and the second tubular knit 20 has the rib structure formed into a tubular shape. Additionally, in the first tubular knit 10 and the second tubular knit 20, the outer protuberances 42 of the rib structure has knit and purl stitch in which the elastic yarn B intermeshes with the base yarn A while the outer protuberances 42 the rib structure has tuck or miss (non-knit) stitch that consists of held loops of the base yarn A and miss or tuck loops of the elastic yarn B. The knit and purl stitch of the elastic yarn B alternates miss or tuck stitch of the elastic yarn B. As a result, circular tension is stronger on the outside than the inside on of the first tubular knit 10 and the second tubular knit 20. This yields the inner protuberances 41 that rises higher and is rounder than the outer protuberances 42.

The rib structure has the knit and purl stitch of the elastic yarn B and the base yarn A alternates miss or tuck stitch of the elastic yarn B and the base yarn A. This results in tension difference in the circumferential direction. In addition, the outer protuberances 42, which appear as the recess lines on the inner surface of the base structure, has knit and purl stitch in which the elastic yarn B intermeshes with the base yarn A while the outer protuberances 42, which appear as the raised lines on the inner surface of the base structure, has tuck or miss (non-knit) stitch that consists of held loops of the base yarn A and miss or tuck loops of the elastic yarn B. Consequently, the inner protuberances 41, which appear as the raise lines on the outer surface of the base structure, rises higher and is rounder than the outer protuberances 42, which appear as the recess lines on the inner surface of the base structure. This makes larger height gap between the inner protuberances 41 and the outer protuberances 42.

Thus, the tubular knit M and the gutter-shaped knit N of the cylindrical bandage 1 according to the present embodiment have the inner surface that has the inner protuberances 41 and the outer protuberances 42, which each extends in lengthwise direction. The tubular knit M and the gutter-shaped knit N has the rugged base structure that is formed into a tubular shape and has the stitches of the elastic yarn B. In particular, the outer protuberances 42 of the base structure with the rib stitches of the base yarn A has the knit stitches of the elastic yarn B while the inner protuberances 41 of the base structure with the rib stitches of the base yarn A has the tuck or miss (non-knit) stitches of the elastic yarn B. Consequently, the tubular knit M and the gutter-shaped knit N has circular tension that is stronger on the outside than the inside, which will directly contact with a user's skin. Additionally, the tubular knit M and the gutter-shaped knit N have difference in circumferential tension between the inner protuberances 41 appearing as the raised lines on the inner surface and the outer protuberances 42 appearing as the recess lines on the inner surface. This yields the inner protuberances 41 that rises higher and is rounder than the outer protuberances 42. Such inner protuberances 41 have higher cushioning. This allows the inner protuberances 41 to get in higher pressure contact with a user's skin.

As the base yarn A forming the rugged base structure such as the rib structure, cotton yarn, nylon yarn, polyester yarn, rayon yarn, silk acrylic yarn, silk yarn, hemp yarn, cotton acrylic blended yarn, hemp acrylic blended yarn, wool yarn, wool blended yarn such as wool acrylic blended yarn, absorbent yarn such as synthetic yarn with hydrophilic group block copolymer or yarn with porous surface, ceramic yarn with far-infrared, elastic yarn made of polyurethane or rubber, or the like are employed. Yarn type, yarn count, and the number of yarn are not limited. Any yarn may be used. The base yarn A may be formed of multiple bundled yarns.

The elastic yarn B is required to have larger elasticity than the base yarn A has. The elastic yarn B may be polyurethane yarn or rubber yarn. Alternatively, the elastic yarn B may covered yarn, which includes elastic core such as polyurethane or span textile and wrap yarn on the corn yarn. The elastic yarn B may be formed of multiple bundled yarns.

A yarn that has higher mechanical strength including tensile strength and does not fray easily is preferably employed although the knitting way can determine strength or stiffness.

For example, use of a thick yarn with a thickness in a range of 500 to 2000 denier allows the cylindrical bandage 1 to be thick and stiff. Such a cylindrical bandage 1 does not wrinkle easily and is not loose and thus have higher effect on increase in venous return.

The tubular knit M and the gutter-shaped knit N preferably have a thickness in range of 2 to 15 mm, more preferably, 5 to 15 mm viewed in cross-section. This allows the knitted fabric LM to be wrinkle free and fit tightly to a target body part when the cylindrical bandage 1 is worn. Since the cylindrical bandage 1 worn on the target body par does not wrinkle and is not loose, the cylindrical bandage 1 is highly effective to increase venous return. In particular, such a thickness allows wrinkles-free on even a movement part such as the instep side of the foot. Thus, compression concentration and tourniquet, which are caused by wrinkles biting a skin, are prevented. The thickness of 2 to 15 mm, more preferably, 5 to 15 mm of the knitted fabric LM is determined in state where the knitted fabric LM is normal, that is, it is not stretched.

The rib structure includes the alternate plain and purl stitches or the alternate face and back wales. In the present embodiment, the plain stitches and the purl stitches extend longitudinally.

The heel knit 30 may have a rib structure or other structures having plain stitches including jersey stitches, pearl stitches, or interlock stitches.

The cylindrical bandage 1 of the present embodiment has one end with an auxiliary holding part knitted at predetermined courses. The one end is the opposite side of the first tubular knit 10 to the second tubular knit 20 and the heel knit 30 and nearer to the heart of a human body.

The cuff that is the top end Q of the gutter-shaped knit N of the knitted fabric LM has a predetermined elasticity for keeping the cylindrical bandage 1 from sliding. This top end Q may be a rib knit for having a predetermined elasticity. Alternatively or additionally, the top end Q may use the elastic yarn B including rubber for having high tension, as with the first tubular knit 10 and the second tubular knit 20.

The cylindrical bandage 1 including the tuber knit M and the gutter-shaped knit N has a predetermined length corresponding to the length of an arm or leg. This cylindrical bandage 1 is formed by intermeshing the loops of the base yarn A and the elastic yarn B. In cross-section view seen from a direction across an arm or leg, the elastic yarn B, which has higher elasticity than the base yarn A, does not appear on the inner surface of the inner protuberances 41. This eliminates the contact of the elastic yarn B with the skin of a user. The gutter-shaped knit N above the tuber knit M has a gutter-shape and a smaller circumference than the knit M.

The gutter-shaped knit N may have lower elasticity or higher Young's modulus than the top unit of the first tubular knit 10 being adjacent to the gutter-shaped knit N. In this case, the top end of the first tubular knit 10 having contact with the femurs has decreased elasticity or tightness. This prevents skin redness and itch caused by the knit biting into the skin and provides comfortable fit. If the top of the first tubular knit 10 is the edge of the cylindrical bandage 1, the elasticity or Young's modulus of the top end is independent of the adjacent unit. In this case, the top end of the first tubular knit 10 may put higher pressure on a femur, disrupt blood circulation, and cause redness and itch on a femur, which is tightened by the end of the first tubular knit 10. In response to the above issue, the gutter-shaped knit N consisting of the knitted fabric LM having low elasticity is joined to the top end of the first tubular knit 10. This prevents compression concentration, which adversely affects venous return. The gutter-shaped knit N preferably has a gradually changing elasticity or Young's modulus from one end being adjacent to the top end of the first tubular knit 10 to the other end for preventing adverse effect on blood circulation. Alternatively or additionally, the gutter-shaped knit N preferably has less increased elasticity when folded double for preventing adverse effect on blood circulation. Such a gutter-shaped knit N allows the end of the first tubular knit 10, which is in contact with a femur, to have lower elasticity. This prevents compression concentration causing skin redness and itch on a femur.

In some embodiments, the bottom end of the cylindrical bandage 1, which is opposite to the gutter-shaped knit N, may have circular fray-stopping(s) for preventing yarn ends from unravelling. The length of the second tubular knit 20 may be adjusted in accordance with the foot length of a user by cutting the knit at a predetermined position including the fray-stopping.

Thus, the second tubular knit 20 may have the circular fray-stopping(s) disposed at its bottom end, which is opposite to the first tubular knit 10, for preventing yarn ends from unravelling. This allows the knit to be cut without unravelling yarn.

For example, such a circular fray-stopping is formed by applying a synthetic resin-based adhesive to the stitches. The form of the circular fray-stopping can prevent cut yarn from unravelling. That is, the yarn can be cut without unravelling. The length of the second tubular knit 20 may be adjusted by cutting the knit at the fray-stopping. The fray-stopping includes a single circle with a predetermined length or multiple circles a predetermined length.

In particular, it is a preferable to use a colored adhesive as the fray-stopping for clarity of cut part. In FIG. 7, the bottom end of the second tubular knit 20 has the cut fray-stopping with a colored adhesive.

With the circular fray-stopping(s) to be cut, the cylindrical bandage 1 having predetermined dimensions determined in accordance with intended compression can vary in length according to the length of a user's leg. That is, the dimensions of the cylindrical bandage 1 are designed in accordance with compression fitting for users while the length of the cylindrical bandage 1 can vary according to the length of a user's leg. Thus, it is easy for a user to select the cylindrical bandage 1 fitting for the user. With the fray-stopping, the cylindrical bandage 1 does not decrease in the strength even when partially cut.

In some embodiments, the cylindrical bandage 1 may have a bottom end T with the fray-stopping(s) formed by binding off. The bottom end T is opposite to the gutter-shaped knit N.

The top end R and the top end W of the gutter-shaped knit N joined to the tuber knit M of the cylindrical bandage 1 also has the fray-stopping(s) formed by binding off.

The knitting of the cylindrical bandage 1 according to the present embodiment is described in detail by referring to FIGS. 10A to 12, which illustrate knitting patterns mainly. The cylindrical bandage 1 according to the present embodiment can be produced by, for example, a flatbed knitting machine including at least a pair of needle beds; a front needle bed and a rear needle, which are opposite to each other. In particular, the cylindrical bandage 1 is preferably a tubular seam-free knitted fabric produced by Wholegarment® knitting machine including MACH2X, MACH2S, or SWG (Shima Seiki Corporation).

A method for knitting the cylindrical bandage 1 of one embodiment is described below. This cylindrical bandage 1 is a tubular seam-free knitted fabric that is knitted using a Wholegarment® knitting machine including a pair of needle beds.

The cylindrical bandage 1 of one embodiment is produced by a Wholegarment® knitting machine including a pair of needle beds with racking for transfer. Specifically, this machine has a needle bed configuration with two-pieces of needle slider having slide needles moving upwards and downwards, which is allowed by running a carriage on the needle beds.

The cylindrical bandage 1 including the tuber knit M and the gutter-shaped knit N according to the embodiment has a right knitted fabric and a left knitted fabric that are symmetrically identical. The left side and right side are between front and back, in which the front corresponds to the knee of a leg and the instep of a foot and the back corresponds to the calf of a leg and the heel of a foot. The symmetrical formation is achieved by using front and rear needle beds of a needle Wholegarment® knitting machine. In FIG. 4B, the positions of the front symmetrical line d1 and the back symmetrical line d3 correspond the return positions of a carriage running on the needle beds. Thus, the right side knitted part and a left side knitted part of the knitted fabric LM are joined at the positions of the symmetrical line d1 and the symmetrical line d2 and formed into a tubular sharp.

The cylindrical bandage 1 including the tuber knit M and the gutter-shaped knit N according to a specific embodiment will be now described by way of example.

The cylindrical bandage 1 including the tuber knit M and the gutter-shaped knit N has the rib base structure composed of the base yarn A and the elastic yarn B, which intermesh with one another. The elastic yarn B has higher elasticity than the base yarn A has.

In the knitting action to form the rib structure, a zig-zag row are formed on the front and back needle beds and ribber stitches are then transferred to knitter. This forms a row of one of the left and right sides of the knitted fabric LM. In the same way, a row of another side part of the knitted fabric LM is formed. The row of the left side and the row of the right side of the knitted fabric LM are joined on the needle head and formed into a circular shape. Thus, face (plain) stitches and reverse (back) stitches alternate on each side of the rib structure knit.

In this embodiment, the rib base structure of the first tubular knit 10 and the second tubular knit 20 is 3×3 rib having three plain wales and three rib wales. This 3×3 rib base structure is mainly formed of the base yarn A having lower elasticity.

In this embodiment, the 3×3 rib structure includes the elasticity yarn B having higher elasticity than the base yarn A. In the 3×3 rib structure, a course of the knitting loops of the elasticity yarn B alternates with a course of the knitting loops of the base yarn A. As show in FIGS. 10A, 10B, and 11 outer protuberances 42, which appear as raised knit stitches in the outer and as recess knit stitches in the inner of the knitted fabric LM, have the knitting loops of elasticity yarn B intermeshes with the knitting loops of the base yarn A, while the inner protuberances 41, which appear as raised knit stitches in the inner and as recess knit stitches in the outer of the knitted fabric LM, have the miss elasticity yarn B floating on the reverse side of the held loop of the base yarn A. Thus, the knit stitches alternates with the float stitches in the course of the elasticity yarn B.

In this embodiment, the elastic yarn B, which has larger elasticity than the base yarn A has, is thinner than the base yarn A. The inner surface of the cylindrical bandage 1 has less exposure of the elastic yarn B under normal conditions NL where the cylindrical bandage 1 does not stretch ST as shown in FIG. 4A. Further, the inner surface of the cylindrical bandage 1 has less exposure of the elastic yarn B even where the cylindrical bandage 1 stretches as shown in FIG. 4B. In particular, the elastic yarn B hides behind the face loop of the base yarn A in the inner surface of the inner protuberances 41 of the cylindrical bandage 1. Thus, the elastic yarn B have less contact with the skin of a user. As shown in FIG. 4A, viewed from the outside the cylindrical bandage 1, it seems that the elastic yarn B is on the knit stitches of the base yarn A.

Figure 8:
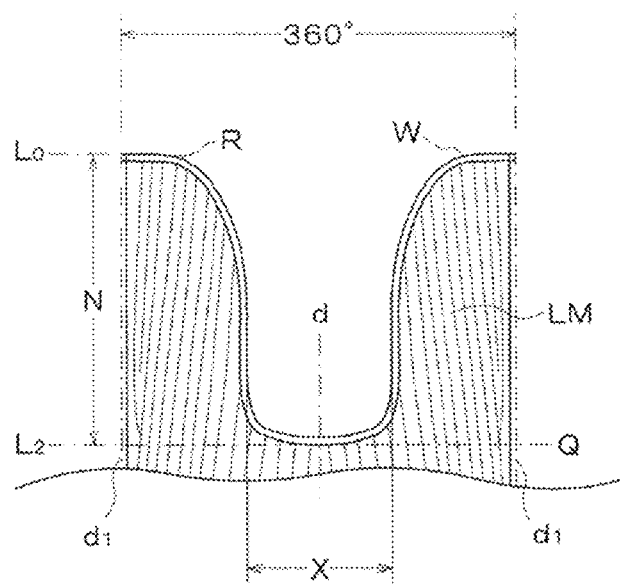
FIG. 8 is a main developed view of a gutter-shaped knit of the cylindrical bandage according to an embodiment of the present invention.

FIG. 8 is a developed view of the knitted fabric LM that is expanded so that a symmetrical line d is located at center. The knitted fabric LM has a first end Q of the top of the tuber knit M nearer to the bottom of the gutter-shaped knit N. In the developed view, x=30° corresponds to the edge length of the top of the tuber knit M. In the embodiment and 360° corresponds to the length between the symmetrical lines $d_1$ and $d_2$. That is, the top first end of the tuber knit M has an annular shape. The gutter-shaped knit N with a predetermined circumference has the smaller numbers of knitting loops than the top first end of the tuber knit M. The number of the knitting loops of the gutter-shaped knit N decreases from the top of the tuber knit M to correspond to a predetermined tube diameter.

The developed knitted fabric LM of the gutter-shaped knit N preferably has X=30° to 270°, which is centered at the symmetrical line d as the center line of the tuber knit M. This allows the gutter-shaped knit N to stand and have a predetermined elasticity.

In the cylindrical bandage 1 of the present embodiment, the first tubular knit 10 and the second tubular knit 20 has transfer stitches in the outer protuberances 42. The transfer stitch is produced by transference of a loop from one needle corresponding to the center of the three plain loops of an outer protuberance 42 to another corresponding to the adjacent loop in the same needle bed. The right transfer stitches alternates with the left transfer stitches in the vertical direction. Such loop transference makes holes and decreased stitch density of the outer protuberances 42, thus allowing more ventilation. Thus, the outer protuberances 42, which appear as raised knit stitches in the outer and as recess knit stitches on the inner, has lower density than the inner protuberances 41 has, which appear as raised knit stitches in the inner and as recess knit stitches in the outer.

The use of a cotton yarn as the base yarn A may also provide good breathable, in addition to good texture, cushion and close contact to a target body part.

In some embodiment, tack stitches may be used to allow more highly breathable.

In the cylindrical bandage 1 of the present embodiment, the heel knit 30 between the first tubular knit 10 and the second tubular knit 20 is a plain knitted fabric (single jersey) using the base yarn A.

The top end W, R of the gutter-shaped knit N has binding off with the fray stopping. The gutter-shaped knit N, which is three-dimensionally knitted, includes the base structure having the stitches of the base yarn A and the stitches of the elastic yarn B, as with the first tubular knit 10 and the second tubular knit 20 shown in FIG. 9. The elastic yarn B is exposed to the outside but not the inside, which will have contact with the skin of a user. The top end, which may cast on side, does not include the elastic yarn B and has lower elasticity.

The case that the knitting starts from the gutter-shaped knit N will be now described. Firstly, the gutter-shaped knit K is three-dimensionally knitted using the base yarn A with lower elasticity and the base yarn B. This gutter-shaped knit K has a plain structure in which the stitches of the base yarn A alternate with the stitches of the base yarn B. The first tubular knit 10 is then knitted using twin needle beds for making the 3×3 rib structure.

The first tubular knit 10 of the present embodiment has a fixed stitch density of the base yarn A. That is, a course height and a wale width of the knitting loops of the base yarn A are fixed. The number of wales of the first tubular knit 10 is set to the approximation of calculation based on the human body circumference date $m_0, m_1, m_2, \ldots m_6$, and $m_7$ corresponding one-to-one to the human body position date $L_0, L_1, L_2, \ldots L_6$, and $L_7$ shown in Table 1 and Young's modulus determined in accordance with the human body position date $L_0, L_1, L_2, \ldots L_6$, and $L_7$. The first tubular knit 10 is knitted in order of the human body position date $L_0, L_1, L_2, L_3, \ldots L_6$, and $L_7$.

As shown in Table 1, the circumference is largest at the human body circumference date $m_7$ and decreases towards the human body circumference date $m_7$ in order. In accordance with the varying diameters, the number of wales or the knitted width of the first tubular knit 10 decreases towards its bottom.

In the cylindrical bandage 1 of the present embodiment, the first tubular knit 10 is knitted in sequence the human body position date $L_1, L_2, L_3, \ldots,$ and $L_7$. The number of the wales of the first tubular knit 10 decreases towards the bottom end having a predetermined circumference or tube diameter, which corresponds to the human body circumference date $m_7$ from the human body position date $L_7$.

Likewise, the gutter-shaped knit N is knitted in sequence the human body position date $L_1, L_1,$ and $L_2$. The number of the wales of the gutter-shaped knit N decreases towards the bottom having a predetermined circumference or tube diameter, which corresponds to the human body circumference date $m_1$ from the human body position date $L_1$.

Figure 10B:
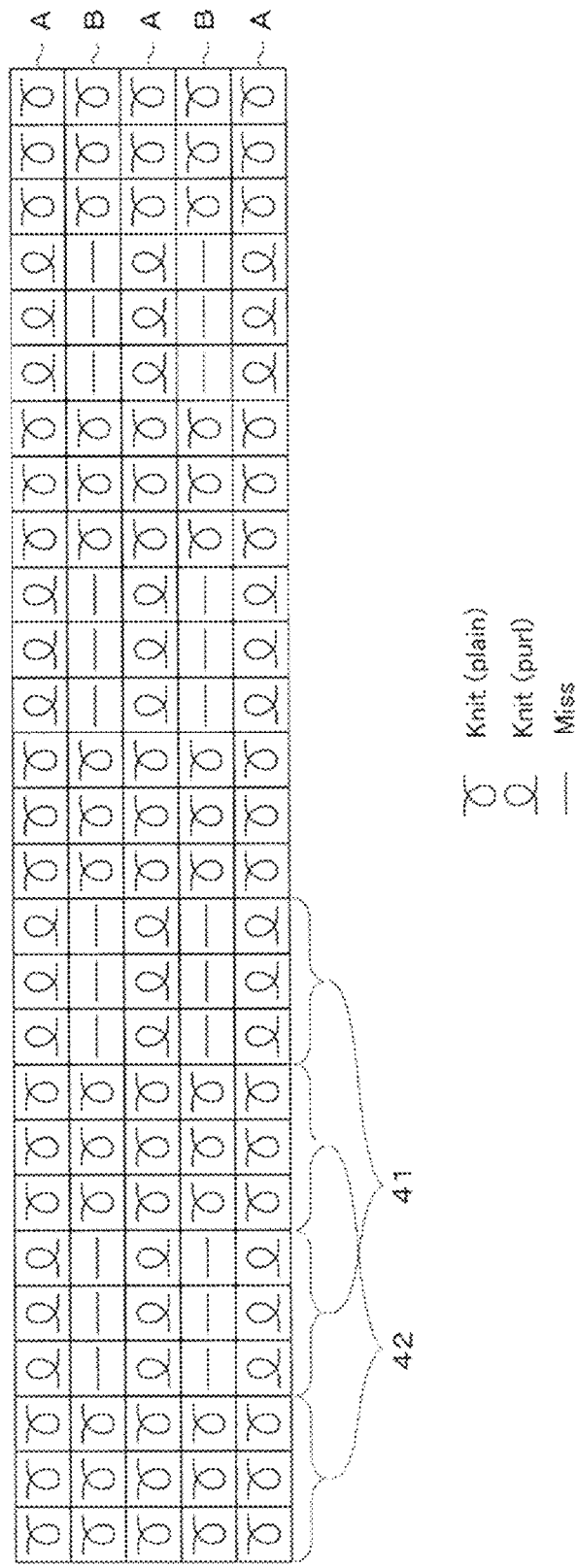
FIG. 10B is a schematic knitting diagrams of a first tubular knit and a second tubular knit of the cylindrical bandage according to an embodiment of the present invention.

In the first tubular knit 10 of the present embodiment, the 3×3 rib structure includes the base yarn A and the elasticity yarn B as show in FIGS. 10A and 10B. The yarn has lower elasticity than the base yarn A. In the 3×3 rib structure, a course of the knitting loops of the elasticity yarn B alternates with a course of the knitting loops of the base yarn A. Each outer protuberance 42, which appear as raised knit stitches of three plain wales in the outer (face) of the 3×3 rib structure, has the knitting loops of elasticity yarn B intermeshes with the knitting loops of the base yarn A, while each inner protuberance 41, which appears as recess knit stitches of three rib wales of the base yarn A in the inner (back) of the 3×3 rib structure, has the miss elasticity yarn B floating on the reverse side of the held loop of the base yarn A. Thus, the knit stitches alternates with the float stitches in the course of the elasticity yarn B. Further, the first tubular knit 10 of the embodiment has transfer stitches in the outer protuberances 42. The transfer stitch is produced by transference from one needle corresponding to the center of the three plain loops of an outer protuberance 42 to another corresponding to the adjacent loop in the same needle bed. The right transfer stitches alternates with the left transfer stitches in the vertical direction.

Figure 11:
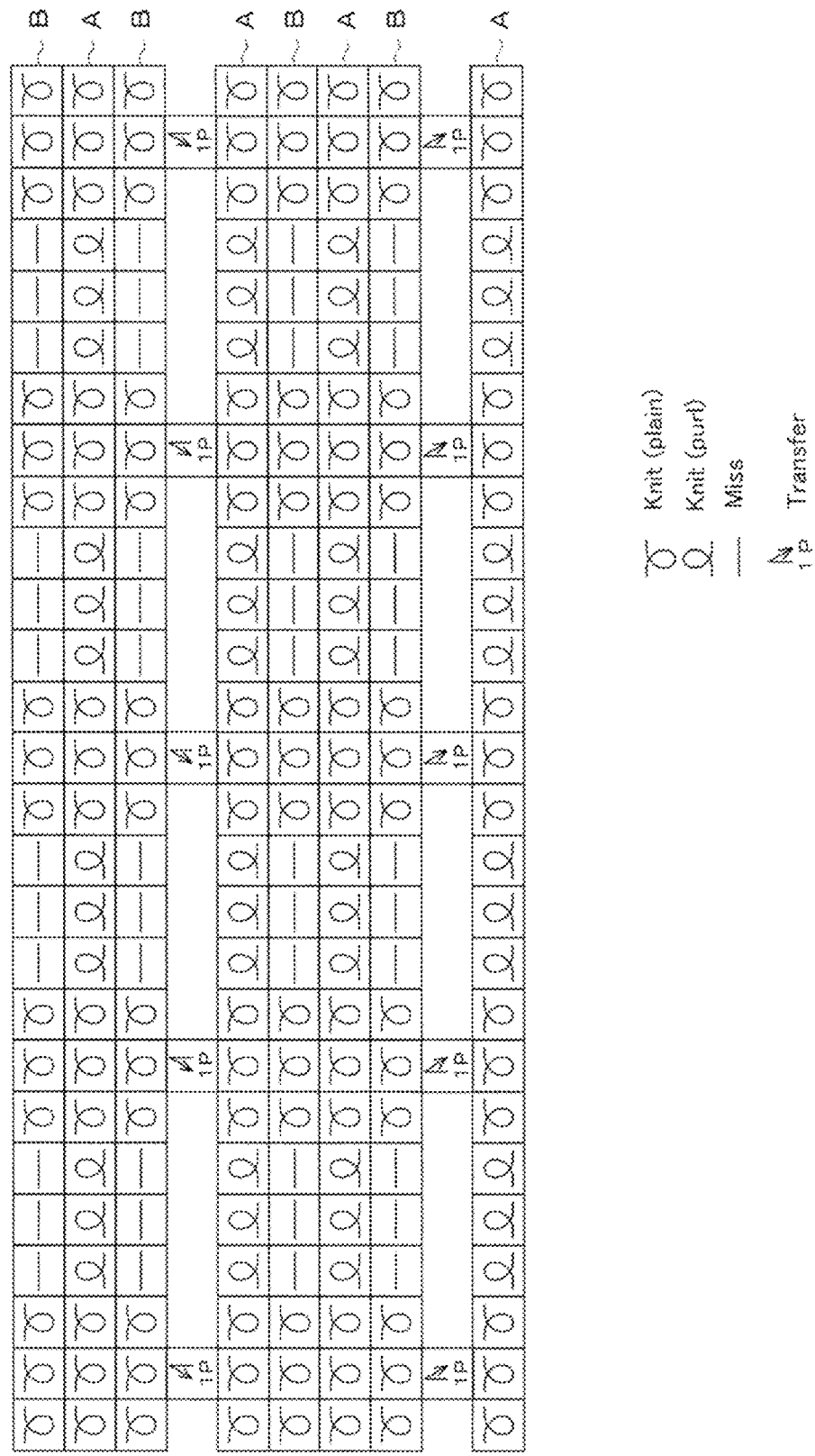
FIG. 11 is a schematic knitting diagrams of a first tubular knit and a second tubular knit of the cylindrical bandage according to an embodiment of the present invention.

Specific knitting procedure will be described referring to FIG. 11. Following the 3×3 ribbing of the base yarn A, the elasticity yarn B is fed onto the needle. This elasticity yarn B intermeshes with the previous three plain wale loops of the base yarn A and misses the previous three rib wale loops of the base yarn A. Thereafter the base yarn A is again fed and the 3×3 ribbing knitted. After the 3×3 ribbing of the base yarn A, the elasticity yarn B is again fed onto the needle.

The knitting of the base yarn A and the knitting of the elasticity yarn B are repeated alternately per one circle. In this process, one needle corresponding to the center of the three plain loops of the outer protuberance 42 is transferred to another corresponding to the adjacent loop in the same needle bed. This loop transfer is periodically repeated. The right transfer stitches alternates with the left transfer stitches in the vertical direction. In this way, the tubular knit M of the cylindrical bandage 1 according to the present embodiment is formed.

While the knitting of the base yarn A with lower elasticity and the knitting of the elasticity yarn B are repeated alternately, the number of the wales or the tubular diameter decreases to reflect the human body circumference date $m_0$, $m_1, m_2, \ldots m_6$, and $m_7$ corresponding to one-to one to the human body position date $L_0, L_1, L_2, \ldots L_6,$ and $L_7$ shown in Table 1. The old loop may be cast off at the end needle(s) or the inside needle(s) of the end needle(s). The number of the wales of the elasticity yarn B intermeshing with the base yarn A decreases in accordance with the decreased number of the wales of the base yarn A.

In the first tubular knit 10 and the gutter-shaped knit N of the cylindrical bandage 1 according to the present embodiment, the front with the symmetrical line $d_1$ has stitches knitted together or suspended stitches, which result from decrease in loops. In knitting, stitch rows decrease in number to provide predetermined tuber diameters in accordance with the human body circumference date $m_0, m_1, m_2, \ldots m_6$, and $m_7$, and the Young's modulus (E). The decreases in knitting are accomplished by, for example, knitting a stitch of plain or rib wales together with an adjacent stitch of plain or rib wales, or suspending a stitch of plain or rib wales. Repetitive decreases in knitting result in reductions in the tube diameter to reflect the human body circumference date $m_0, m_1, m_2, \ldots m_6$, and $m_7$, and Young's modulus (E). One or two stitch decreases (two to four decreases in a circumference) in accordance with the human body circumference date $m_0, m_1, m_2, \ldots m_6$, and $m_7$ in knitting allow the knitted fabric to be free of projection, corrugation, and wrinkle. Such a knitted fabric fits a leg better and provides suitable compression and comfortable fit. In some embodiments, several stitches may decrease at once.

In the present embodiment, the front with the symmetrical line d1 (which is the left end of the knitted fabric of FIG. 4B) has stitches knitted together or suspended stitches, which result from decrease in stitch. In the front as shown in FIG. 7, each outer protuberance 42 and each inner protuberance 41 extend longitudinally to the symmetrical line d1 as a center line. In the back, each outer protuberance 42 and each inner protuberance 41 extend longitudinally to the lower in parallel. Thus, outer protuberances 42 and inner protuberances 41 run along the lymph and venous flow. This allows great increase in venous return or lymph return. The front and the back with the symmetrical lines d1 and d2 as the center line correspond to the return positions of the carriage or the fed yarn, or the ends of stitch row in knitting. Thus, the ends of stitch row in knitting represent the front and the back with the symmetrical lines d1 and d2, and do not correspond to malleolus. Consequently, the first tubular knit 10 and the second tubular knit 20 has good appearance and can more closely cover the malleolus and its circumference.

In some embodiments, the back may have stitches knitted together or suspended stitches, which result from stitch decrease. Alternatively, the middle between the front and the back may have stitches knitted together or suspended stitches, which result from stitch decrease. In particular, decrease of the stitches at the end of row in knitting allows the knitted fabric to be free of warp.

Thus, the number of the wales of the first tubular knit 10 knitted in sequence the human body position date $L_1, L_2, L_3, \ldots$, and $L_7$ decreases towards the bottom end having a predetermined circumference or a predetermined tube diameter corresponding to the human body position date $L_7$. Following the knitting of the first tubular knit 10, the heel knit 30 is knitted through successive knitting cycles using the end needles having the old loops of the first tubular knit 10. A fed yarn is knitted into the heel knit 30 having a horseshoe or U shape in cross-section by using the needles. In knitting of the heel knit 30, only one-end needles on each needle bed are used and remaining needles are not used. The number of the remaining needles that are not used in knitting of the heel knit 30 are 60% of that of needles holding the previous loops of the first tubular knit 10. That is, the number of the needles used in knitting of the heel knit 30 is 40% of that of needles used in knitting of last loops of the first tubular knit 10. In this embodiment, the heel knit 30 is plain fabric (single jersey).

In the cylindrical bandage 1 of the present embodiment, the knitting needles positioned at either ending in all knitting needles holding the last row loops of the first tubular knit 10 on the needle beds are used to knit first row loops of the heel knit 30 shown in FIGS. 10B to 12F illustrating knitting diagrams. Following this, the needles that are contiguous with the ending needles and the needles that do not hold the last row loops of the first tubular knit 10 are used to knit new loops. This increases in the number of wales or knitting width. This processing is repeated and the knitting yarn is fed into a C shape. The number of wales increases every courses.

After the number of wales increases to a predetermined number, the number of the needles used in knitting gradually decreases. In this decrease in knitting width, the ending needles holding the previous loops of the heel knit 30 is not used to knit new loops while new needles that do not hold any previous loops of the heel knit 30 and the last row loops of the first tubular knit 10 are used to knit new loops. Needles used to knit new loops are shifted from inside to outside (from left to right in FIG. 5). This processing is repeated and the knitting yarn is fed into a C shape. The number of wales decreases every courses. It is noted that the decrease in number of the new loops is greater than the previous increase in number of the new loops.

For example, thirty knitting loops of the top end the heel knit 30 may intermesh with the end last knitting loops of the first tubular knit 10. The maximum number of the needles used in the knitting of the heel knit 30 may be twenty-five. In this case, with two ending needles holding the last loops of the first tubular knit 10, the knitting of the heel knit 30 may starts as shown in FIG. 5. Following this, the adjacent needles lying inside the ending needles holding the last loops of the first tubular knit 10 are used for new loops while the new needles that do not hold the last loops of the first tubular knit 10 are used for new loops. This increases the number of the wales or knitting width. This processing is repeated and thus the number of the needles used for new loops is increased until twenty. Thus, the yarn is knitted into the knit in C shape. After the number of the needles used for new loops is increased to twenty, needles used for new loops are shifted from inside to outside. Specifically, the ending needles holding the previous loops of the heel knit 30 is not used for new loops while new needles that do not hold any previous loops of the heel knit 30 and the last loops of the first tubular knit 10 are used for new loops. This processing is repeated and thus the number of the needles used for new loops is decreased until two. It is noted that the decrease in number of the new loops is greater than the previous increase in number of the new loops. Preferably, the number of the needles for new loops gradually increases or decreases by one or two on either side (two to four on the one circumference).

This knitting way according to the present embodiment does not form gore line in the heel knit 30. In the present embodiment, the needle used to knit the endmost loop of the last row of the first tubular knit 10 is the most used needle to knit the heel knit 30 at successive knitting cycles. That is, the endmost loop (back side) of the last row of the first tubular knit 10 has the most courses of the heel knit 30. In FIG. 4B viewed in side, the heel knit 30 has a substantially sectored trapezoidal shape with a center (border) P. In the present embodiment, the decrease or increase in the number of the loops are the same in both needle beds. This yields the knitted fabric LM having symmetry. FIG. 5 shows the knitting width of the right side of the knitted fabric LM. The right side is a right side viewed from the front corresponds to the knee of a leg and the instep of a foot.

This flat knitting does not limit needles used for knitting the heel knit 30 and provides sufficient knitting loops for knitting the heel knit 30, unlike circular knitting. Thus, the flat knitting offers flexibility for the shapes or dimensions of the heel knit 30. The flat knitting allows the knitted fabric LM to have large area and wide inside space and to fit three-dimensional shapes of a heel. The knitted fabric LM is not tense on the heel.

The heel knit 30 has varying the knitting widths or the varying numbers of wales and the varying positions of endmost new loop of rows. The endmost loop (back side) of the last row of the first tubular knit 10 has the most courses of the heel knit 30. Consequently, the heel knit 30 has varying curvatures and fits the three-dimensional shapes of a heel. Varying the knitting width and the positions of endmost new loop of rows yields curvature or swelling fitting to a heel and makes yields the inside having a wide space corresponding to the dimensions of a heel. Thus, the knitted fabric is not tense on a heel. In particular, there is not any gore lines in the heel knit 30. Thus, the heel knit 30 has good visual appearance. Since there is no gore line in the heel knit 30, the heel knit 30 stretches easily and does not wrinkle easily. Thus, the heel knit 30 fits to a heel better and is not tense on a heel. The presence of such a heel knit 30 allows the first tubular knit 10 and the second tubular knit 20 to get in closer contact with the malleolus and its surroundings. Further, the flat knitting provides gentle hold-down. This yields the knitted fabric LM with less distortion.

In some embodiments, the heel knit 30 may have a fixed knitting width or have increase in the number of the stitches or wales towards its last row.

Less than 40% of the knitting needles holding the last row loops (wales) of the first tubular knit 10 are used to knit the first row loops of the heel knit 30. Preferably, 10 to 40%, more preferably, 20 to 40% of the knitting needles holding the last loops of the first tubular knit 10 are used to knit the first row loops the heel knit 30. Further, less than 40% of the knitting needles used to knit the first loops (wales) of the second tubular knit 20 are used to knit the last row loops of the heel knit 30. Preferably, 10 to 40%, more preferably, 20 to 40% of the knitting needles used to knit the first loops of the second tubular knit 20 are used to knit the last row loops of the heel knit 30. Thus, the topmost knitting width of the heel knit 30 is less than 40% of the endmost knitting width of the first tubular knit 10 and the endmost knitting width of the heel knit 30 is less than 40% of the topmost knitting width of the second tubular knit 20. The topmost knitting width of the heel knit 30 is preferably 10 to 40%, more preferably, 20 to 40% of the endmost knitting width of first tubular knit 10 and the endmost knitting width of the heel knit 30 is 10 to 40%, more preferably, 20 to 40% of the topmost knitting width of the second tubular knit 20. This prevents the cylindrical bandage 1 from being tense on a heel and the first tubular knit 10 and the second tubular knit 20 from floating at the part around a malleolus. The first tubular knit 10 and the second tubular knit 20 can get in closer contact with the part around a malleolus.

In some embodiments, starting needle used to knit the first row loops of the heel knit 30 may not be needles holding the last row loops of the first tubular knit 10. Needles that do not hold the last row loops of the first tubular knit 10 may be used to knit the first row loops of the heel knit 30. In this case, the heel knit 30 may again have increase in the number of the wales towards its last row. The knitted fabric may be asymmetric. This occurs when there is a difference in decrease or increase of the numbers of the wales or the position of the endmost new loops between the front and rear needle beds.

Following the knitting of the heel knit 30, the second tubular knit 20 is then knitted using a fed yarn. The needles holding the last row loops of the first tubular knit 10 and the needles holding the last row loops of the heel knit 30 are both used to knit the second tubular knit 20. Since the needles holding the last row loops of the first tubular knit 10 are used to knit the first row loops of the second tubular knit 20, the first row loops of the second tubular knit 20 intermesh with the last row loops of the first tubular knit 10. Additionally, since the needles holding the last row loops of the heel knit 30 are used to knit the first row loops of the second tubular knit 20, the first row loops of the second tubular knit 20 intermesh with the last row loops of the heel knit 30.

The number of the first row loops of the second tubular knit 20 is 10 to 40%, preferably, 20 to 30% larger than that of the last row loops of the first tubular knit 10. That is, the circumference of the top end of the second tubular knit 20 is 1.1 to 1.4 times, preferably, 1.2 to 1.3 times as long as that of the bottom end of the first tubular knit 10. Thus, the top end of the second tubular knit 20 has larger diameter or circumference than the bottom end of the first tubular knit 10 has.

The second tubular knit 20 has the rib base structure having a fixed stitch density of the base yarn A. That is, a course height and a wale width of the knitting loops of the base yarn A are fixed. The number of wales of the second tubular knit 20 is set to the approximation of calculation based on the human body circumference date $m_8$, $m_9$ and $m_{10}$ or $m_9$ and $m_{10}$ corresponding one-to-one to the human body position date $L_8$, $L_9$, and $L_{10}$ or $L_9$ and $L_{10}$ shown in Table 1 and Young's modulus determined in accordance with the human body position date $L_8$, $L_9$, and $L_{10}$ or $L_9$ and $L_{10}$. The second tubular knit 20 has the varying numbers of stitches to correspond to the varying dimensions of the cross-section. The second tubular knit 20 is knitted in order of the human body position date $L_8$, $L_9$, and $L_{10}$ or $L_9$ and $L_{10}$.

The number of the wales or the knitted width of the second tubular knit 20 decreases towards its bottom corresponding to the human body circumference date $m_9$ and $m_{10}$.

As with the first tubular knit 10, the second tubular knit 20 has the 3×3 rib structure, in which the stitches of the base yarn A with lower elasticity alternate with the stitches of the elastic yarn B with higher elasticity row by row.

In the second tubular knit 20 of the cylindrical bandage 1 according to the present embodiment, the back with the symmetrical line d2 has stitches knitted together or suspended stitches, which result from stitch decreases in knitting as shown in FIGS. 3A and 7. Gradual decreases in the number of stitch rows in knitting yields the knitted fabric LM gradually becoming thinner or narrower towards the end. The decreases in the number of stitch rows in knitting are accomplished by, for example, knitting a stitch of plain or rib wales together with an adjacent stitch of plain or rib wales, or suspending a stitch of plain or rib wales. Repetitive decreases in knitting result in reductions in the tube diameter to reflect the human body circumference data m8, m9, and m10, or m9 and m10. One or two stitch decreases (two to four decreases in a circumference) in knitting allow the knitted fabric to be free of projection, corrugation, and wrinkle. Such a knitted fabric LM fits a leg better. In some embodiments, several stitches may decrease at once.

In the second tubular knit 20 of the present embodiment, the back with the symmetrical line d2 (which is the right end of the knitted fabric of FIG. 3A) has stitches knitted together or suspended stitches, which result from stitch decreases in knitting. In the back corresponding to the back of a foot, each outer protuberance 42 and each inner protuberance 41 extend longitudinally to the symmetrical line d2 as a center line. In the front corresponding to the instep of a foot, each outer protuberance 42 and each inner protuberance 41 extend longitudinally to the lower end in parallel. This allows great increase in venous return or lymph return from tiptoes. In some embodiments, the front corresponding to the instep of a foot may have stitches knitted together or suspended stitches, which result from stitch decreases in knitting. Alternatively, the middle between the front and the back may have stitches knitted together or suspended stitches, which result from stitch decreases in knitting. In particular, decrease of the stitches at the end of row in knitting allows the knitted fabric LM to be free of warp.

In the knitting according to the present embodiment, after the knitting of the first tubular knit 10 is finished, the yarn used for knitting of the first tubular knit 10 is cut and changed to another yarn for knitting the heel knit 30. After the knitting of the heel knit 30 is finished, the yarn for knitting the heel knit 30 is cut and changed to another yarn for knitting the second tubular knit 20. Although cutting a yarn does not affect its strength, it is preferable that the cut yarn is tied or a synthetic adhesive is applied to the cut yarn to prevent fraying and to keep the strength.

Compression on the ankle joint of a human foot mold wearing the cylindrical bandage 1 of the present embodiment described above was measured.

In this cylindrical bandage 1, as the yarn A knitted into the first tubular knit 10 and the second tubular knit 20, five cotton yarns 20/2 were used. As the elastic yarn B, two double covered yarns, which each includes a polyurethane core yarn with 260 denier and a wrap polyester yarn with 75 denier on the core yarn, were used. As the yarn A knitted into the heel knit 30, two cotton yarns 20/2 were used.

Further, compression on the foot mold wearing a commercially available elastic stocking (conventional product) for lymphedema was also measured for comparison with the cylindrical bandage 1. The measurements are given in Table 2.

TABLE 2

| | ⟨Example⟩ | | | | |
|---|---|---|---|---|---|
| | Measurement points | | | | |
| | e<br>Bottom part around medial malleolus nearer to heel | f<br>Bottom part around lateral malleouls nearer to heel | g<br>Instep | h<br>Ankle | i<br>Calf (crus) |
| First time | 27 | 24 | 25 | 22 | 21 |
| Second time | 25 | 25 | 26 | 23 | 20 |
| Third time | 26 | 26 | 23 | 24 | 21 |
| Fourth time | 25 | 24 | 25 | 23 | 19 |
| Fifth time | 26 | 24 | 25 | 24 | 18 |
| The mean value | 25.8 | 24.6 | 24.8 | 23.2 | 19.8 |

| | ⟨Comparative example⟩ | | | | |
|---|---|---|---|---|---|
| | Measurement points | | | | |
| | e<br>Bottom part around medial malleolus nearer to heel | f<br>Bottom part around lateral malleouls nearer to heel | g<br>Instep | h<br>Ankle | i<br>Calf (crus) |
| First time | 10 | 9 | 22 | 30 | 29 |
| Second time | 14 | 11 | 23 | 31 | 28 |
| Third time | 17 | 15 | 22 | 30 | 26 |
| Fourth time | 15 | 10 | 22 | 28 | 27 |
| Fifth time | 16 | 13 | 23 | 28 | 26 |
| The mean value | 14.4 | 11.6 | 22.4 | 29.4 | 27.2 |

Unit: mmHg

As shown in Table 2, the cylindrical bandage 1 according to the embodiment described above allows all of measurement points to provide compression (of about 10 to 46 mmHg) effective in treatment for lower limb lymphedema.

In a conventional product as a comparative example, the compression on a measurement points e and f in the bottom of a malleolus nearer to a heel are half that of a measurement point g in the instep of a foot. The difference in the compression between the measurement points e and f in the bottom of the malleolus and the measurement point g in the instep is about 50% (about 8 to 11 mmHg). The compression on the measurement point g in the instep is about 75% that of a measurement point h in an ankle. The compression on the measurement points e and f in the bottom of the malleolus are about 40 to 50% that of a measurement point h in the ankle.

In the cylindrical bandage 1 according to the embodiment described above, the compression on the measurement points e and f in the bottom of the malleolus is equal to that of the measurement point g in the instep. The difference in the compression between the measurement points e and f and the measurement point g in the instep is only 5% (1 mmHg). The compression on the measurement point g in the instep and the compression on the measurement points e and f are equal to or greater than that of a measurement point h in the ankle.

A target body part is heled between the end W and the end R of the knitted fabric LM of the gutter-shaped knit N. That is, the knitted fabric LM of the gutter-shaped knit N with the end W and the end R tightens the target body part suitably. Thus, the knitted fabric LM fits around a leg. In particular, the tubular knit M and the gutter-shaped knit N of the cylindrical bandage 1 according to the present embodiment have the varying numbers of the stitches to correspond to the varying shapes of a body part. This allows provision of compression tailored to individual cases. Alternatively, the compression may be standardized. The standard compression is easily calculated using body dimension date of users or average body dimension date of people. In particular, the circumference is varied by varying the number of the stitches. This yields intended compression easily. Consequently, desired compression can be provided to even a predetermined part of patients having serious varicose venous or lymphedema causing swelling. This allows further increase in venous return.

The cylindrical bandage 1 is not likely to create wrinkles and compression concentration on the instep of a foot and to be tense on a heel side. Such a cylindrical bandage 1 allows the knitted fabric LM to get close contact with even the bottom of a malleolus and to fit tightly around an ankle. Thus, the cylindrical bandage 1 puts high pressure on the bottom of a malleolus and provides little difference in compression between an instep and the bottom of a malleolus nearer to a heel. The cylindrical bandage 1 provides uniform compression distribution. Additionally, the cylindrical bandage 1 provides little difference in the compression between an ankle and the foot front part ranging from an instep to a malleolus. The compression on the foot front part ranging from an instep to a malleolus is equal to or greater than the compression on the ankle. Thus, the cylindrical bandage 1 allows great increase in venous return in a lower limb. In particular, the cylindrical bandage 1 allows relief for lymphedemas or hypertrophy of a malleolus or the back of an ankle. The cylindrical bandage 1 provides high compression on even the bottom of a malleolus nearer to a heel and on the back of an ankle, in which excess lymph is trapped. In addition, the cylindrical bandage 1 has the ribs and grooves (the outer protuberances 42 and the inner protuberances 41) extending longitudinally. These ribs and grooves make the varying compression that allows further increase in venous return. Furthermore, these ribs and grooves run along lymph flows. This also allows further increase in venous return.

The cylindrical bandage 1 was evaluated by rating the compression, lymphedemas improvement effect (venous return promoting effect), and comfortable or tight fit.

Some cylindrical bandages 1 were prepared for evaluation. In each cylindrical bandage 1 including the tubular knit M and the gutter-shaped knit N, which were different in circumference, the yarn A knitted into the first tubular knit 10 and the second tubular knit 20 consists of five cotton yarns 20/2, the elastic yarn B knitted into the first tubular knit 10 and the second tubular knit 20 consists of two double covered yarns, which each includes a polyurethane core yarn with 260 denier and a wrap polyester yarn with 75 denier on the core yarn, and the yarn A knitted into the heel knit 30 consists of two cotton yarns 20/2. The compression on the ankle of the foot mold waring the cylindrical bandage 1 was measured. Further, we carried out a survey. In the survey, thirty testers with lymphedema worn the cylindrical bandage 1 and took a survey about comfortable or tight fit and lymphedemas improvement effect. The comfortable or tight fit and the lymphedemas improvement effect were rated in relation to the compression.

If the compression on a human body wearing the cylindrical bandage 1 is measured, the compression varies depending on shapes or resilience of the body. Thus, the compression on the human left foot mold, specifically, men's five-toed socks for display (TENKENSOUI, Co., Ltd. 51-196-10-2) wearing the cylindrical bandage 1 of the embodiment was measured to eliminate the variation in compression.

The compression (in hhmg) was rated based upon the compression on the measurement point f in the bottom of a lateral malleolus near the heel. The compression was measured using the same compression measurement equipment in the same manner as described above.

Thirty testers with lymphedema ranging from mild to severe worn the cylindrical bandage 1 including the tubular knit M and the gutter-shaped knit N on their lower limbs for one or two weeks, six to twelve hours per day. The testers took a survey about lymphedemas improvement effect (lymphedemas relief effect) in the lower limb and about comfortable or tight fit. The lymphedemas improvement effect and comfortable or tight fit wear were rated, in relation to the compression. The improvement effect is rated on a scale of 1 to 3; excellent, good, and fair. The comfortable or tight fit is also rated on a scale of 1 to 3; excellent, good, and poor, in which the excellent means the testers felt comfortable fit, the good means the testers felt a little tight fit but did not feel discomfort, and the poor means the testers felt tight fit and discomfort or the testers had skin irritation, which may be caused by musty. The average rating results are given in Table 3.

TABLE 3

| | Compression on measurement point f (mmHg) | | | | | | | | | |
|---|---|---|---|---|---|---|---|---|---|---|
| | 10 | 15 | 20 | 25 | 30 | 35 | 40 | 45 | 50 | 55 |
| Improvement of edema | ▲ | ○ | ◎ | ◎ | ◎ | ◎ | ◎ | ◎ | ◎ | ○ |
| Comfortable fit | ◎ | ◎ | ◎ | ◎ | ◎ | ◎ | ◎ | ◎ | ○ | ▲ |

As shown in Table 3, with the compression applied on the measurement point f in the bottom of a lateral malleolus nearer to a heel of 15 mmHg or more, the cylindrical bandage 1 reduces edema effectively. With the compression applied on the measurement point f of 20 mmHg or more, the cylindrical bandage 1 reduces edema more effectively. However, with the compression applied on the measurement point f of 50 mmHg or more, the cylindrical bandage 1 is small efficient in reducing edema depending on a tester.

With the compression applied on the measurement point f in the bottom of a lateral malleolus nearer to a heel of 50 mmHg or less, the cylindrical bandage 1 provides comfortable fit, or less tight fit and less discomfort. With the compression applied on the measurement point f in the bottom of a lateral malleolus nearer to the heel of 45 mmHg or less, the cylindrical bandage 1 provides more comfortable fit.

Thus, with the compression applied on the measurement point f in the bottom of a lateral malleolus nearer to the heel in a range of 15 to 50 mmHg, the cylindrical bandage 1 reduces edema effectively and provides comfortable fit, or little tight fit and less discomfort. A preferred compression is in a range of 20 to 45 mmHg. This compression is large efficient in reducing edema and provides more comfortable fit.

In all prepared cylindrical bandages 1, which are different in circumference, the difference in compression between an instep and the bottom of a lateral malleolus nearer to a heel is less than 20% (less than 5 mmHg).

In the cylindrical bandage 1 of the present embodiment, the stitch density of the base yarn A and the stitch density of the elastic yarn B are fixed across the human body position date $L_0, L_1, L_2, L_3, \ldots$. It means there is no change in the used yarns. When a certain yarn used in knitting is changed to another yarn with a different type including a thickness from a previous yarn in knitting mid-way, the stitch density may change. When there is no change of used yarn, the stitch density is fixed. The yarn used in the knitting may be one, two, or more types. The yarn may consist of a single or a combination of different types.

In the 3×3 rib structure formed of the stitches of the base yarn A, the outer protuberances 42 have the knitting loops of the elasticity yarn B that intermeshes with the knitting loops of the base yarn A while the inner protuberances 41 have the miss loops of the elasticity yarn B that floats on the reverse side of the held knitting loops of the base yarn A. The stitch row of the elasticity yarn B alternates with the stitch row of the base yarn A.

The stitch density of the base yarn A, the stitch density of the elastic yarn B, and Young's modulus are fixed across the human body position date $L_0, L_1, L_2, L_3, \ldots$.

This yields the first tubular knit 10 and the second tubular knit 20 providing uniform compression generally. Stress concentration does not be provided to a particular part of a target body part. Consequently, the user does not feel discomfort. The first tubular knit 10 and the second tubular knit 20 provides uniform compression even though the body part has varying cross-sections across the length direction.

In some embodiments, the varying degrees of compression across the length direction may be provided by varying Young's modulus and stitch density in accordance with the human body position date $L_0, L_1, L_2, L_3, \ldots$. The Young's modulus and stitch density can be varied by varying the number of wales, knitting pattern of the base yarn A or the elastic yarn B, or the knitting of the elastic yarn B. The cylindrical bandage 1 for a lower limb may be designed so as to gradually become less constrictive towards the top end nearer to the heart of the human. This cylindrical bandage 1 may allow further increase in venous return.

Figure 12B:
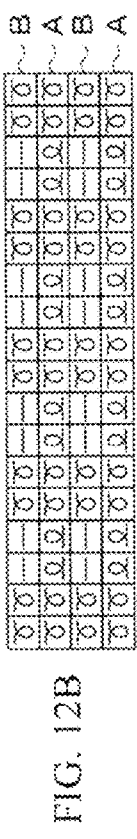
FIG. 12B is a schematic knitting diagrams of a first tubular knit and a second tubular knit of the cylindrical bandage according to still another embodiment of the present invention.
Figure 12A:
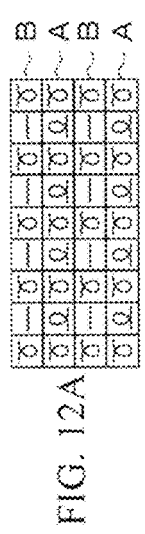
FIG. 12A is a schematic knitting diagrams of a first tubular knit and a second tubular knit of the cylindrical bandage according to another embodiment of the present invention.

In the embodiment described above, the first tubular knit 10 and the second tubular knit 20 have the 3×3 rib structure, in which three plain wales alternates three rib wales. However, the number of the plain wales and the rib wales is not limited to this value. For example, the rib structure may be 1×1 rib, which consists of alternate face and back wales as shown in FIG. 12A. As shown in FIG. 12A, the outer protuberances 42 may have knit stitches of the elasticity yarn B while inner protuberances 41 may have miss or tuck stitches of the elasticity yarn B. Alternatively, the rib structure may be 2×2 rib, which consists of alternate two plain wales and two rib wales as shown in FIG. 12B, or may be 8×8 rib, which consists of alternate eight plain wales and eight rib wales as shown in FIG. 12D. In these cases, the outer protuberances 42 may have knit stitches of the elasticity yarn B while inner protuberances 41 may have miss or tuck stitches of the elasticity yarn B.

Figure 12C:
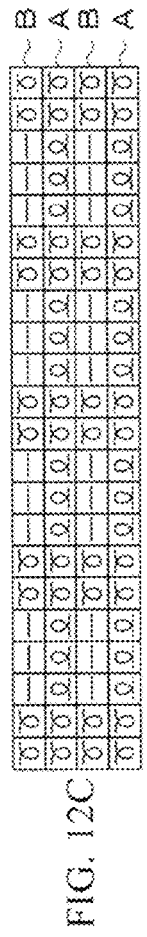
FIG. 12C is a schematic knitting diagrams of a first tubular knit and a second tubular knit of the cylindrical bandage according to still another embodiment of the present invention.
Figure 12D:
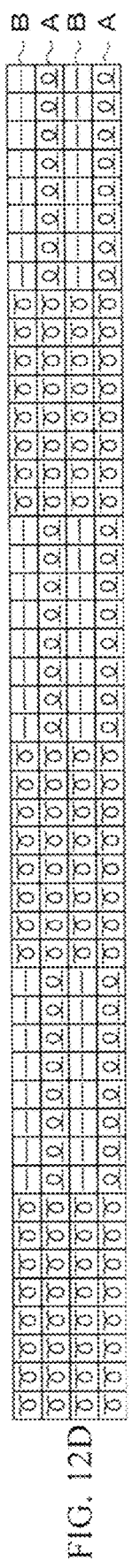
FIG. 12D is a schematic knitting diagrams of a first tubular knit and a second tubular knit of the cylindrical bandage according to still another embodiment of the present invention.
Figure 12E:
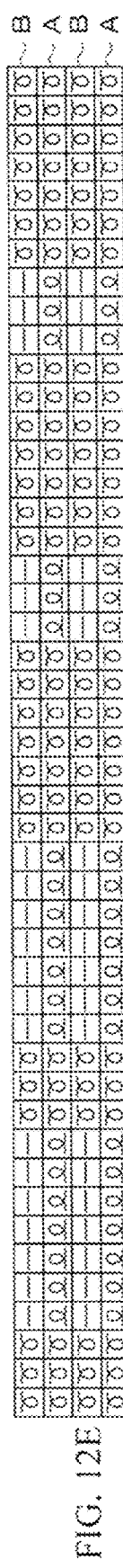
FIG. 12E is a schematic knitting diagrams of a first tubular knit and a second tubular knit of the cylindrical bandage according to still another embodiment of the present invention.
Figure 12F:
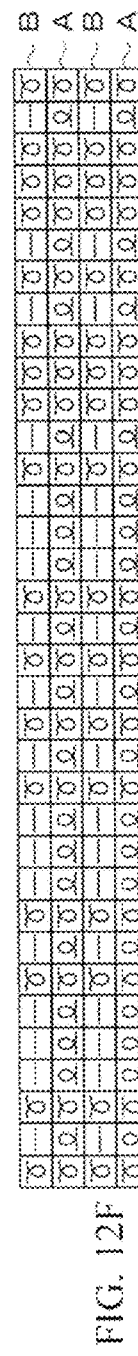
FIG. 12F is a schematic knitting diagrams of a first tubular knit and a second tubular knit of the cylindrical bandage according to still another embodiment of the present invention.

Alternatively, the plain wales and the rib wales may be different in number, as shown in FIG. 12C illustrating a 2×3 rib structure, which consists of alternate two plain wales and three rib wales. Further, the cycle of alternate plain and rib wales may be regular or may be irregular as shown in FIGS. 12E and 12F. In these cases, the outer protuberances 42 may have knit stitches of the elasticity yarn B while inner protuberances 41 may have miss or tuck stitches of the elasticity yarn B.

Thus, in some embodiments, the number of the wales of each outer protuberance 42, which appears as the raise line on the outer surface and as the recess line on the inner surface of the cylindrical bandage 1 and extends longitudinally, may vary. The number of the wales of each inner protuberance 41, which appears as the raise line on the inner surface and as the recess line on the outer surface of the cylindrical bandage 1 and extends longitudinally, may also vary.

In the embodiment described above, stitch rows alternate a stitch row of the base yarn A knitted into the rib structure with a stitch row of the elastic yarn B through the length in knitting. However, the alternation of the yarn A and the elastic yarn B is not limited to each row. The elastic yarn B may alternate with the base yarn A every second or third rows. The alternation may be irregular. In the embodiment described above, to eliminate contact of the elasticity yarn B with the skin of a user, the outer protuberances 42 may have knit stitches of the elasticity yarn B intermeshing with knit stitches of the yarn A knitted into the rib structure. while inner protuberances 41 may have miss stitched of the elasticity yarn B. floating on the held loops of the base yarn A. However, the elastic yarn B is not limited to this knitting. The stitches of the elastic yarn B may be tuck stitches instead of miss stitches, or may be both tuck stitches and miss stitches. The stitches of the elastic yarn B may be any stitches other than knit, miss and tuck stitches.

In the embodiment described above, each outer protuberance 42 and each inner protuberance 41 extend longitudinally. Alternatively, the outer protuberances 42 and the inner protuberances 41 may be discrete and represent grid pattern. In this case, again, the inner surface, which will have contact with a skin, has circumferentially alternative ribs (the inner protuberances 41) and grooves (the outer protuberances 42) and the cross-section has waveform or corrugation. This yields varying degrees of compression in the circumferential direction. The varying degrees of compression allow further increase in venous flow or lymph flow, and venous return. The knitting pattern making ribs and grooves is limited to rib stitches. The knitting pattern may be seed, moss, thermal, or waffle stitches. These stitches also provide ribs and grooves.

In the embodiment described above, the rib base structure with the rib stitches of the base yarn A includes the stitches of the elastic yarn B. Such a rib base structure has high tension or elasticity from the elastic yarn B in addition to extensibility from the rib stitches. This provides higher compression and elasticity. However, the stitches of the elastic yarn B may be omitted. The use of the base yarn A with higher elasticity in the rib base structure also achieves provision of higher compression and elasticity.

In the embodiment described above, the first tubular knit 10 is firstly knitted. However, knitting start is not limited to this knit. The second tubular knit 20 may be firstly knitted.

That is, the cylindrical bandage 1 may be knitted in order of the second tubular knit 20, the heel knit 30, the first tubular knit 10, and the gutter-shaped knit N. In this case, the number of wales of the second tubular knit 20 gradually increases towards the heel knit 30. In the knitting of the heel knit 30, the number of wales increases and decreases. Thus, the heel knit 30 has the varying numbers of wales. In the knitting of the first tubular knit 10 following the heel knit 30, the number of wales increases towards the human body position date $L_1$ from the human body position date $L_7$.

In the knitting of the gutter-shaped knit N following the first tubular knit 10, the number of wales decreases towards the human body position date $L_0$ from the human body position date $L_2$.

In the tubular knit M and the gutter-shaped knit N contiguous with it according to present embodiment, the number of wales is calculated to using the human body circumference date $m_0$, $m_1$, $m_2$, $m_3$, ... and predetermined Young's modulus, which is determined in accordance with the human body position date $L_1$, $L_1$, $L_2$, $L_3$, . . . . The increase and decrease in stitches yields the knitted fabric reflecting the shapes and dimensions of a body part such as a lower limb.

The cylindrical bandage 1 of the present embodiment is weft-knitted by a weft knitting machine. This cylindrical bandage 1 has the varying numbers of wales to correspond to the varying circumferences of a body part such as a lower limb.

Thus, the cylindrical bandage 1 of the present embodiment has varying knitted widths or varying circumferences from the varying numbers of the stitches. Such a cylindrical bandage 1 is shaped in conformance with a body part such as a lower limb. This cylindrical bandage 1 has a certain direction. The increase and decrease in the number of stitches in knitting makes varying widths or varying circumferences corresponding to the varying shapes and dimensions of the body part and makes desired compression. Greater flexibility for design of the dimensions, shapes, or circumferences is allowed. Optimal tube diameter corresponding to the dimensions and shapes of the body and intended compression is easily designed. In particular, it is difficult for conventional stockings knitted by circular machines to have a tube diameter fitting to the dimensions and shapes of the part around ankle. However, this cylindrical bandage 1 has a tube diameter fitting to the dimensions and shapes of the part around ankle.

Thus, the knitted fabric LM of the cylindrical bandage 1 is not loose and does not wrinkle on the instep of a foot and does not give compression concentration with horizontal wrinkles when worn on the part around ankle. Additionally, the knitted fabric LM of the cylindrical bandage 1 does not give discomfort and fails to slide, which both results from looseness and wrinkles on the instep of a foot. The knitted fabric LM of the cylindrical bandage 1 is not tense or loose and does not wrinkle on a heel side. If the knitted fabric LM has looseness and wrinkles, the knitted fabric LM would be stretched in its longitudinal direction to eliminate the looseness and wrinkles when worn. In this case, the knitted fabric LM would be the part ranging from the malleolus to the back of the heel. However, since the cylindrical bandage 1 is not loose and does not wrinkle on the part around an ankle, the knitted fabric LM makes in close contact with the part ranging from the malleolus to the back of the heel and provides high compression on it. The higher compression on the malleolus allows reduction of organic tissue thickening at the back side of the malleolus.

In the cylindrical bandage 1 including the tubular knit M and the gutter-shaped knit N, the number of stitches of the top end row of the second tubular knit 20 is larger than that of the bottom end row of the first tubular knit 10. Thus, the width $l_2$ of the top end of the second tubular knit 20 is wider than the width $l_1$ of the bottom end of the first tubular knit 10. That is, the tube diameter or circumference of the first row of the second tubular knit 20 is wider than that of the last row of the first tubular knit 10. Between the first tubular knit 10 and the second tubular knit 20, the heel knit 30 is knitted at predetermined courses. This heel knit 30 has the varying numbers of wales. Such a heel knit 30 provides wide space and three-dimensional shapes inside the tube to correspond to the shapes of a round heel. Thus, the cylindrical bandage 1 does not wrinkle and is not tense at a heel when worn. In the present embodiment, the round heel knit 30 is knitted between the first tubular knit 10 and the second tubular knit 20.

At the border between the first tubular knit 10 and the second tubular knit 20, the ratio of the length a to the length b is in a range of 6:4 to 9:1 with the cylindrical bandage 1 folded along the front symmetrical line $d_1$ and the back symmetrical line $d_2$ dividing wales in tow. The length a is a length of the virtual perpendicular line $c_1$ connecting between the front symmetrical line $d_1$ and the border P between the first tubular knit 10, the second tubular knit 20, and the heel knit 30. The length b is a length of the virtual perpendicular line $c_2$ connecting between the back symmetrical line $d_2$ and the border P. As a result, the foot part in range from the instep to the malleolus is covered with not the round heel knit 30 but the first tubular knit 10 and the second tubular knit 20 when the cylindrical bandage 1 is worn. The first tubular knit 10 and the second tubular knit 20 is substantially circular in cross-section and is free of curvature in the longitudinal direction unlike the heel knit 30, and thus allows for uniform compression. Such a first tubular knit 10 and a second tubular knit 20 fit tightly to the undulation parts around the malleolus when the cylindrical bandage 1 is worn. The presence of the heel knit 30 with curvatures prevents the knitted fabric from being pulled by the heel and having high tension on the heel and keeps the knitted fabric away from the undulation parts around the malleolus. This allows the first tubular knit 10 and the second tubular knit 20 to get close contact with the undulation parts around the malleolus and fit tightly to them. This yields uniform compression on the undulation parts around the malleolus.

The heel knit 30 is preferably contiguous with 10 to 40%, more preferably, 20 to 40% of the circumference of the last stitch row of the first tubular knit 10 and is preferably contiguous with 10 to 40%, more preferably, 20 to 40% of the circumference of the first stitch row of the second tubular knit 20. This prevents the first tubular knit 10 and the second tubular knit 20 from being pulled by the heel and having high tension when the cylindrical bandage 1 is worn and covers the part around the ankle. This cylindrical bandage 1 is not tight and provides comfortable fit. Additionally, since the first tubular knit 10 and the second tubular knit 20 is prevented from being pulled by the heel and having high tension keeping the knitted fabric away from the undulation parts around the malleolus, the first tubular knit 10 and the second tubular knit 20 fit tightly to the undulation parts around the malleolus.

The cylindrical bandage 1 including the tubular knit M and the gutter-shaped knit N has the inside surface with rib base structure having alternative ribs and grooves, specifically, the inner protuberances 41 appearing as the raised line on the inner surface and the outer protuberances 42 appearing as the fallen line in the inner surface, which will have contact with a body part. Each rib and each groove extend longitudinally in parallel. The ribs alternate with the grooves in the circumferential direction. With alternation of the ribs and the grooves, the cross-section has a waveform or corrugation. Such an alternation of the ribs and the grooves provides the varying degrees of compression in the circumferential direction perpendicular to the longitudinal direction of the body part. Additionally, the ribs and the grooves extending longitudinally run along lymph flows. This allows further increase in lymph flow and venous return and eliminates discomfort caused by compression concentration and felt by a user.

Further, the knitted fabric LM having the inner surface with the ribs and grooves has varying surface. Such a knitted fabric LM gets in closely contact with even undulation or curvy parts with varying cross-sections.

In the embodiment, the rib structure of the rib stitches of the base yarn A includes the knit stitches of the elastic yarn B in the outer protuberances 42 and the miss or tuck stitches of the elastic yarn B in the inner protuberances 41. The stitch row of the elastic yarn B alternates with the stitch row of the base yarn A in the rib structure. As a result, the outer has higher tension than the inner, which will have a contact with the skin. This makes larger height gap between the projections (the inner protuberances 41 appearing as the raised lines in the inner) and recesses (the outer protuberances 42 appearing as the fallen lines in the inner) in the inner of the cylindrical bandage 1. Consequently, the inner protuberances 41, which appear as the raise lines in the inner and extend longitudinally, rises higher and is rounder than the outer protuberances 42, which appear as the recess lines in the outer. Such inner protuberances 41 have increased cushioning. This allows the inner protuberances 41 to be more closely contact with the skin.

Thus, the rib structure of the rib stitches of the base yarn A includes the knit stitches and the miss or tuck stitches of the elastic yarn B. This makes the difference in tension between ribs (the inner protuberances 41 appearing as the raised lines on the inner surface) and grooves (the outer protuberances 42 appearing as the fallen lines on the inner surface) on the inner surface of the cylindrical bandage 1. In particular, the outer protuberances 42 include the knit stitches of the elastic yarn B and the inner protuberances 41 include the miss or tuck stitches of the elastic yarn B. This makes larger height gap between the ribs (the inner protuberances 41 appearing as the raised lines on the inner surface) and grooves (the outer protuberances 42 appearing as the fallen lines on the inner surface) on the inner surface of the cylindrical bandage 1. Consequently, the inner protuberances 41, which appear as the raise lines on the inner surface and extend longitudinally, rise higher and is rounder than the outer protuberances 42. Such inner protuberances 41 have higher cushioning and thus get more closely contact with a skin.

Thus, the cylindrical bandage 1 allows the inner protuberances 41 to more closely approach with a skin and provides higher compression and has highly effective on increase in venous return accordingly.

The cylindrical bandage 1 is less likely to be loose and wrinkle when worn on and covers an ankle. Thus, the cylindrical bandage 1 creates no compression concentration. Additionally, the cylindrical bandage 1 is less likely to be tense on a heel side. Thus, the cylindrical bandage 1 closely approaches with the malleolus and its surroundings, and fits tightly around an ankle. Such a cylindrical bandage 1 provides less difference in compression between an instep and the bottom of a malleolus and provides uniform compression. This allows great increase in venous return, and effective reduction, improvement, and prevention of edemas such as lymphedema. Further, this cylindrical bandage 1 is effective for relief or reduction of tiredness and swelling. Varying the number of stitches of rows yields intended tube diameter and compression in accordance with a target body part easily. This allows the cylindrical bandage 1 to fit to the target body part. Additionally, the cylindrical bandage 1 does not cause pain, skin damage, skin laceration, and skin tears, which result from the rub of a loose or tight knitted fabric LM. Additionally, this cylindrical bandage 1 does not cause tourniquet from compression concentration.

The cylindrical bandage 1 including the tubular knit M and the gutter-shaped knit N according to the present embodiment includes the knit stitches of the elastic yarn B in the outer protuberances 42 of the rib structure with the rib stitches of the base yarn A and the miss or tuck stitches of the elastic yarn B in the inner protuberances 41 of the rib structure with the rib stitches of the base yarn A. Such a knitting of the elastic yarn B through the rib structure makes less exposure of the elastic yarn B on the inner surface of the cylindrical bandage 1. The elastic yarn B is prevented from coming in contact with a skin. Such a cylindrical bandage 1 is comfortable and has good texture. Use of a cotton yarn as the base yarn A also provides comfort and good texture, and higher water absorption to prevent musty. Further, stitches density, or the course height and the wale width can be changed desired. This allows desired breathable.

In particular, the cylindrical bandage 1 according to the present embodiment has the outer protuberances 42 with transfer stitches. This cylindrical bandage 1 allows highly breathable. The compression can be changed desired by changing the number of the stitches, the elasticity of the base yarn A and the elastic yarn B, the stitch types of the elastic yarn B, or stitch density.

The cylindrical bandage 1 with the rib structure has the grooves (the outer protuberances 42 appearing as the recess lines on the inside) and the projections (the inner protuberances 41 appearing as the raised lines on the inside). The grooves alternate with the projections in the circumferential direction. The grooves and projections run longitudinally. The alternate recesses and projection extend longitudinally. In particular, the cylindrical bandage 1 has alternate plain wales and purl wales in the both, face and back. That is, the cylindrical bandage 1 has alternate face and back wales on the inside and outside. Thus, the knitted fabric LM does not wrinkle easily and thus more closely approach with a target body part and provides more stable compression.

Thus, the knitted fabric LM can come into more closely contact with the malleolus, in which excess lymph may be trapped. This allows increase in lymph around the malleolus and reduction in edemas around the malleolus. The first tubular knit 10 and the second tubular knit 20 have the inner surface with circumferentially alternate ribs and grooves. This yields the varying degrees of compression and thus allows further increase in lymph flow and venous return. In particular, the ribs and the grooves extending longitudinally run along lymph or venous flows. This provides higher lymph or venous promoting effect. The cylindrical bandage 1 that covers a leg including the base of toes promotes lymph flow from the base of the toes towards the heart and increases in venous return effectively. The gradual decrease in compression towards femurs from an ankle allows further increase in venous return. For example, the compression on an ankle may be in a range of 10 to 70 mmHg, the compression on a crus may be in a range of 5 to 35 mmHg, and the compression on femurs may be in a range of 3 to 20 mmHg.

The cylindrical bandage 1 including the tubular knit M and the gutter-shaped knit N according to the present embodiment has the first tubular knit 10 and the second tubular knit 20 with the varying numbers of the wales in accordance with the human body circumference date $m_0$, $m_1$, $m_2$, $m_3$, ... corresponding one-to-one to the human body position date $L_1$, $L_1$, $L_2$, $L_3$, .... The number of the wales approximates calculation based on the human body circumference date $m_0$, $m_1$, $m_2$, $m_3$, ... and Young's modulus determined in accordance with the human body position date $L_0$, $L_1$, $L_2$, .... Thus, the number of the wales is determined using the circumference date of the body and Young's modulus. This provides desired compression corresponding to the positions of a body part and allows further increase in venous return. The varying numbers of the wales determined using Young's modulus makes elasticity corresponding to the human body position date $L_0$, $L_1$, $L_2$, ....

In the cylindrical bandage 1 according to the present embodiment, the first tubular knit 10 and the second tubular knit 20, which is contiguous with the first tubular knit 10, has the varying numbers of stitches to correspond to the varying cross-sections of a human body. This allows provision of compression tailored to individual cases. Alternatively, the compression may be standardized. The standard compression is easily calculated using body dimension date of users or average body dimension date of people. In particular, the circumference is varied by varying the number of the stitches. This yields intended compression easily. Consequently, desired compression can be provided to even a predetermined part of patients having serious varicose venous or lymphedema causing swelling. This allows further increase in venous return.

The cylindrical bandage 1, in which varying the numbers of the stitches is allowed, can fit and put pressure on a body part having larger varying dimensions and shapes due to serious varicose vein or lymphedema. Thus, the knitted fabric LM is not too loose or tight. Such a knitted fabric LM does not cause pain, skin damage, skin laceration and skin tears, which may result from rubbing of the knitted fabric LM to a skin. Commercial items of conventional elastic stockings for varicose vein or lymphedema have not been suited to Japanese people. In contrast, the cylindrical bandage 1 of the present embodiment can fit Japanese people size when the number of the stitches is determined using body dimension date of Japanese people. The cylindrical bandage 1 may be tailored to individual dimensions.

Use of Young's modulus determined by referring to yarn properties and stitch density allows provision of fixed compression.

The cylindrical bandage 1 as a lower limb supporter, which covers a leg including a foot excepting toes, an ankle, the lower of a calf, the upper of a calf, shin, the lower of a knee, and the upper of the knee, has the rib structure with alternate plain and purl stitches of the base yarn A. Such a cylindrical bandage 1 has high elasticity. Additionally, the rib structure includes the stitches of the elasticity yarn B. This increases in compression. Thus, this cylindrical bandage 1 with the predetermined number of the stitches provides compression in a range of 3 to 70 mmHg.

The cylindrical bandage 1 is put on the body part of a use by being stretched vertically or horizontally. Thus, anyone can easily put on and take off the cylindrical bandage 1 when stretching vertically or horizontally as necessary. This cylindrical bandage 1 is convenient to handle and carry around.

In the first tubular knit 10 and the second tubular knit 20 of the tubular knit M according to the present embodiment, vertical elasticity or Young's modulus (E) is lower than or equal to horizontal elasticity or Young's modulus ($E_0$). When the vertical Young's modulus (E) is equal to the horizontal Young's modulus ($E_0$), the vertical elasticity is equal to the horizontal elasticity. When the vertical Young's modulus (E) is larger than the horizontal Young's modulus ($E_0$), the tubular knit M stretches more easily in the vertical direction that is the longitudinal direction of the tubular knit M than in the horizontal direction or the radial direction of the tubular knit M, in which a leg is put. When the vertical Young's modulus (E) is lower than the horizontal Young's modulus ($E_0$), the tubular knit M stretches more easily in the horizontal direction or the radial direction than in the vertical direction. In this case, users can easily put on the cylindrical bandage 1. Thus, it is preferable that the horizontal Young's modulus ($E_0$) is larger than the vertical Young's modulus (E). This allows the tubular knit M to have lower stretch in the vertical direction. Thus, the cylindrical bandage 1 is easy to slide vertically when put on or taken out. That is, the cylindrical bandage 1 is hard to stretch vertically while the cylindrical bandage 1 is easy to slide vertically when put on or taken out vertically. The stretch of the cylindrical bandage 1 is determined in accordance with elasticity or Young's modulus and the human body circumference date $m_0$, $m_1$, $m_2$, $m_3$, ... corresponding one-to-one to the human body position date $L_0$, $L_1$, $L_2$, $L_3$, .... Even inexperienced users put on the cylindrical bandage 1 easily. In some embodiments, the vertical elasticity or Young's modulus (E) may be larger than or equal to the horizontal elasticity or Young's modulus ($E_0$).

The cylindrical bandage 1 of the present embodiment has the form of a tube. The first tubular knit 10 and the second tubular knit 20 of this cylindrical bandage 1 has a rib structure. The rib structure includes the stitches of the elastic yarn B and thus has higher elasticity. Such a cylindrical bandage 1 worn on a body part does not slip off and slide easily even when the body part moves.

The cylindrical bandage 1 that is produced by wholegarment knitting machine and has seam-free is friendly on the skin and will keep its shape while washed. The seam-free allows uniform horizontal tension, elasticity and compression. The knitting with seam-free minimizes post-processing of the knitting yarn.

Conventional elastic stockings knitted by circular knitting machines have an ankle part with highest stitch density and highest tension of a knitting yarn. This ankle part provides higher compression. Consequently, a user needs to strongly put the own foot having the heel with larger circumference than the ankle into the ankle part when put on the elastic stockings. For old people and women with weak fingers, such elastic stockings are hard to put on. Further, the conventional elastic stockings wrinkle easily on an instep. This causes the ankle part with highest stitch density to have poor breathable. In particular, nylon knitted fabric LM may cause an allergy on the skin easily.

In contrast, the first tubular knit 10 and the second tubular knit 20 of the cylindrical bandage 1 including the tubular knit M and the gutter-shaped knit N according to the present embodiment has dimensions and shapes corresponding to the body shapes and dimensions. The number of wales of the first tubular knit 10 and the second tubular knit 20 is set to the approximation of calculation base on Young's modulus determined in accordance with the human body position date $L_1$, $L_1$, $L_2$, $L_3$, .... Thus, varying numbers of wales makes the varying circumferences with the stitch density fixed.

Such a cylindrical bandage 1 can provide intended compression and good stretch. Thus, users, even old people and women with weak fingers, easily put on or take out the cylindrical bandage 1 when stretching the cylindrical bandage 1 vertically, and horizontally as necessary. The cylindrical bandage 1 can be put on a body part without needing excessive stretch and thus will last longer.

In the embodiment described above, the course direction in knitting is the width direction of the knitted fabric LM. The rib structure with the rib stitches of the base yarn A has the stitches of the elastic yarn B. This provides horizontal and vertical stretch. In particular, the rib structure with the rib stitches of the base yarn A has the miss stitches of the elastic yarn B. This provides higher horizontal stretch. Thus, the cylindrical bandage 1 is very easy to put on and out. The cylindrical bandage 1 even with low stitch density provides moderate hold, comfortable fit and has large elasticity. Further, the rib structure with the rib stitches of the base yarn A has the outer protuberances 42 with the knit stitches of the elastic yarn B. This provides higher vertical elasticity. The cut of the elastic yarn B has little effect on the elasticity. The tuck stitches of the elastic yarn B also cause increase in elasticity.

The varying circumferences of a body part are reflected in the varying numbers of stitches. The cylindrical bandage 1 does not wrinkle and provide compression concentration on the instep of a foot when worn. The cylindrical bandage 1 can made from cotton. Thus, the cylindrical bandage 1 is good breathable and does not get sweaty easily. Heat of vaporization of sweat may result in increase in venous return. The thick knitted fabric, which uses a cotton yarn and does not wrinkle easily, can provide the compression of 3 to 70 mmHg or higher and to be easy to put on or take off. Further, the cylindrical bandage 1 will keep its shape even after the cylindrical bandage 1 is washed repeatedly.

This cylindrical bandage 1 achieves both increase in venous return and good breathability.

Since the varying circumferences of a body part are reflected in the varying numbers of the stitches, flexibility for the design or knitting pattern is allowed.

In the cylindrical bandage 1 according to the present embodiment, the first tubular knit 10 and the second tubular knit 20 have the inner surface with alternate rib lines (the inner protuberances 41) and groove lines (the outer protuberances 42). The rib and groove lines run longitudinally on the inner surface, which will have contact with a body part. The alternate rib and groove lines make the cross-section with waveform or corrugation. The first tubular knit 10 and the second tubular knit 20 cover the foot part ranging from the instep to the malleolus. Thus, the tuber knit M having the inner surface with the rib lines or the inner protuberances 41 can makes in contact with even the surroundings of the malleolus, in which lymph is apt to accumulate. This allows further increase in venous return.

It is difficult to for conventional elastic stockings to put pressure on the bottom of the lateral malleolus. However, the cylindrical bandage 1 worn on the body part around ankle can provide the compression of 15 mmHg or higher on the bottom of the lateral malleolus nearer to the heel. The cylindrical bandage 1 can provide 5 mmHg or less difference, preferably, 3 mmHg or lower difference, more preferably, 1 mmHg or less difference in the compression between the instep and the bottom of the malleolus. The cylindrical bandage 1 can provide 40% or less difference, preferably, 30% or less difference, more preferably, 10% or less difference in the compression between the instep and the bottom of the malleolus. Such a cylindrical bandage 1 allows the knitted fabric LM to get in close contact with even the foot part around ankle with varying circumferences and provides uniform compression on the foot part around ankle. Consequently, large increase in venous return can be achieved.

High compression can promote venous return, however, may cause pain, skin damage, skin laceration and skin tears to some serious skin. The compression less than 3 mmHg or less may fail to increase venous return while the compression of above 70 mmHg may adversely affect venous return.

The compression on the bottom of the lateral malleolus nearer to the heel is preferably in a range of 3 to 70 mmHg, more preferably, 5 to 60 mmHg. Such a compression allows increase in venous return without causing pain, skin damage, skin laceration and skin tears. A most preferred compression is, 15 to 50 mmHg, particularly, 20 to 45 mmHg. Such a compression allows further increase in venous return and comfortable fit.

The cylindrical bandage 1 with the inner surface having alternate rib and groove lines (the inner protuberances 41 and the outer protuberances 42) has the varying degrees of compression. The varying degrees of compression allows further increase in venous return. Additionally, the rib and groove lines run along the lymph flow. This also allows further increase in venous return. Thus, even with low compression, the cylindrical bandage 1 can achieve large increase in venous return.

Thus, the cylindrical bandage 1 is effective for therapy or prevention of localized edemas from a wide range of disease, for example, venous (e.g., varicose vein, deep vein thrombosis, venous thrombosis after-affect, or pulmonary embolism), lymph (e.g., incomplete development, lymph node dissection, or lymphangitis), inflammatory, allergy (e.g., from drugs, plants, or bug bites), vascular nerve (e.g., Quincke's edema), disused (e.g., bedridden state for a long period, paralysis), or sequela of surgery. This cylindrical bandage 1 can be used as compression stockings, compression sleeves, or compression bandages, which are used for therapy or prevention of lymphedema of limbs. Stockings, sleeves or bandages providing the compression of 30 mmHg is called compression stockings, sleeves, or bandages in Japan.

Such compression stockings, sleeves or bandages for therapy and prevention of varicose vein, deep vein thrombosis, pulmonary embolism, and lymphedema are subject to medical care expenses in accordance with doctor's instructions. The cylindrical bandage 1 may be used as compression garments including bandages, supporters, sleeves, stockings. The compression garments are elastic fabrics fitting tightly around a body part. The cylindrical bandage 1 may be also used as seam-free bandage. The cylindrical bandage 1 may be used for medical purpose, for example, used as supporters for the lymphedema or varicose vein of limbs. The cylindrical bandage 1 may be also used as compression tubular bandage worn on an arm, a leg, a head, a foot, a wrist, or a hand. The cylindrical bandage 1 worn on limb can help prevent or reduce edema, swelling, or varicose vein while giving compression. Some cylindrical bandages 1 may be worn on body parts with edema.

Application of the cylindrical bandage 1 is not limited to medical supporters for the lymphedema or varicose vein of limbs. The cylindrical bandage 1 may be also used as compression garments including bandages, supporters, sleeves, stockings, undershirts, socks, and gloves. The cylindrical bandage 1 can help prevent or reduce swelling or relive fatigue. The cylindrical bandage 1 having the inner surface with irregularities provides the varying degrees of compression. The varying degrees of compression allows further increase in circulation and preventive or reduction effect on swelling or fatigue.

Application of the cylindrical bandage 1 is not limited to compression purpose. The cylindrical bandage 1 may be used as normal garments including bandages, supporters, sleeves, stockings, undershirts, socks, gloves and mittens.

Figure 13A:
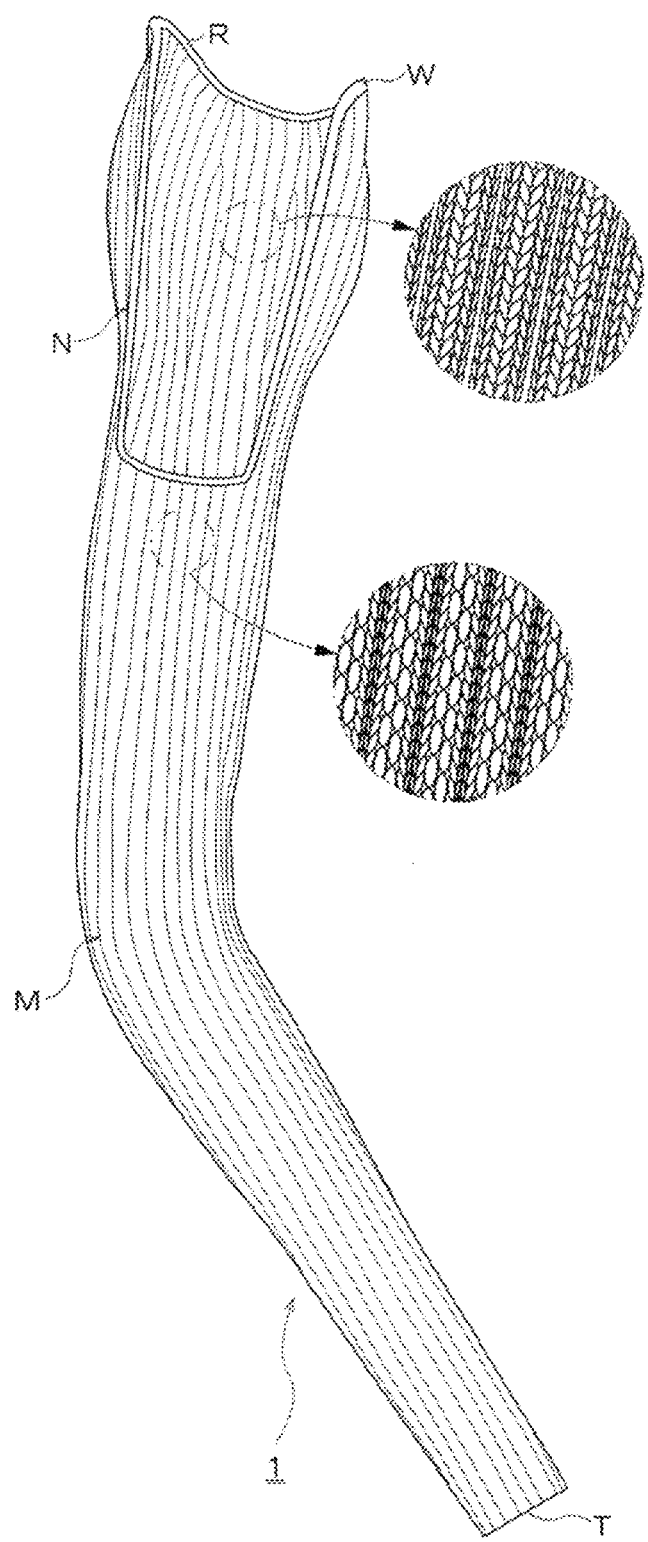
FIG. 13A is a perspective view of the cylindrical bandage according to another embodiment of the present invention.
Figure 13B:
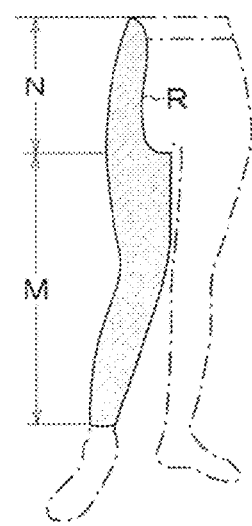
FIG. 13B is a view from the front of the cylindrical bandage worn a body part.

FIGS. 13A and 13B shows a cylindrical bandage 1 in which the present invention is embodied. This cylindrical bandage 1 includes the gutter-shaped knit N having a top end disposed on a pelvis. The gutter-shaped knit N also has the varying numbers of stitches. With the varying numbers of stitches, the gutter-shaped knit N has the varying circumferences. Varying the number of stitches easily makes the varying elasticities of the gutter-shaped knit N. Such a cylindrical bandage 1 also provides desired compression on a target body part even a body part having serious deformity from varicose venous or lymphedema, and increases venous return.

The cylindrical bandage 1 is thinner or narrower at the bottom and thicker or wider at the top. The gutter-shaped knit N has the middle with a bulge. Such a gutter-shaped knit N holds and fits a buttock and a pelvis. The number of stitches of the part above the tubular knit M of the cylindrical bandage 1 for a lower limb is determined using the human body circumference data m0, m1, and m2 corresponding one-to-one to the human body position data L0, L1, L2. Such a cylindrical bandage 1 is held in place without using binding means such as strings tied to the lower limb. This cylindrical bandage 1 fits the shapes and dimensions of a body part and stays on the body part and thus allows further increase in venous return.

FIGS. 14A and 14B shows cylindrical bandages 1 according to another embodiment. Each cylindrical bandage 1 has the gutter-shaped knit N having the top ends W and R with an adhesive fabric 35 or 36 enabling the cylindrical bandage 1 to upstand. In FIG. 14A, the adhesive fabric 35 and the adhesive fabric 36 according to the embodiment is positioned at the back. Alternatively, the adhesive fabric 35 and the adhesive fabric 36 may be positioned at the front. These adhesive fabrics 35 and 36 enable stabilization of the two cylindrical bandages 1. Additionally, these adhesive fabrics 35 and 36 constrain the free top ends W and R to move. The adhesive fabrics 35 and 36 prevent the free top ends W and R from being turned up even when a user wearing cylindrical bandages 1 tosses and turns a lot.

In some embodiments, the cylindrical bandage 1 does not require the adhesive fabrics 35 and 36. If desired the cylindrical bandages 1 may have the adhesive fabrics 35 and 36. These adhesive fabrics 35 and 36 may be positioned at the back, the front, or the both.

FIGS. 15A, 15B and 15C shows a cylindrical bandage 1 according to still another embodiment. The tuber knit M has a bottom end t through which a thumb is inserted and a bottom end T through which fingers from first to forth are inserted. The bottom end T is disposed on five metacarpal bones mc and mcl.

The gutter-shaped knit N above the other end of the tuber knit M covers a shoulder blade, a biceps, and a subscapularis muscle. The gutter-shaped knit N has the varying circumferences made by varying the number of stitches. Varying the number of stitches easily makes the varying elasticities corresponding to a target body part. Thus, desired compression can be provided to even a predetermined part of patients having serious varicose venous or lymphedema causing swelling. This allows further increase in venous return.

The cylindrical bandage 1 of the present embodiment is thinner or narrower at the top and thicker or wider at the bottom and includes the gutter-shaped knit N having the middle with a bulge. Such a cylindrical bandage 1 fits the shoulder blade, the biceps, and the subscapularis muscle. The number of stitches of the part above the tubular knit M of the cylindrical bandage 1 for a upper limb is also determined using the human body circumference data m0, m1, and m2 corresponding one-to-one to the human body position data L0, L1, and L2, although this is not shown. Such a cylindrical bandage 1 is held in place without using binding means such as strings tied to the upper limb. This cylindrical bandage 1 fits the shapes and dimensions of a body part and stays on the body part and thus allows further increase in venous return.

The cylindrical bandage 1 of the present embodiment allows the knitted fabric to get in intimate contact with a body part. The knitted fabric using a cotton yarn is good at breathability, comfortable fit, and cushioning. Thus, the cylindrical bandage 1 may be worn under known compression stockings, that is, it may be used as a cushioning disposed between a body part and the stockings. In this case, the cylindrical bandage 1 allows increase in venous return promotion effect of the stockings. In particular, the knitted fabric using a cotton yarn is less likely to cause skin damage, skin laceration, skin tears, and tourniquet.

The cylindrical bandage 1 as a lower limb supporter according to the present embodiment covers a leg ranging from a foot excluding toes to a thigh. In some embodiments, the cylindrical bandage 1 may cover a leg ranging from a foot including the instep and to the lower of the knee or the hip. The cylindrical bandage 1 may cover the toes of the foot. To cover the toes, the bottom of the second tubular knit 20 with the varying numbers of stitches may be closed by bind off like socks including toe socks as a lower limb supporter (a long supporter). The cylindrical bandage 1 is not limited to for a lower limb. Alternatively, the cylindrical bandage 1 may cover on an arm, a hand, or wrist. For the cylindrical bandage 1 worn on an arm, the heel knit 30 fits the bend of an elbow (an olecranon). This cylindrical bandage 1 allows the knitted fabric to get in intimate contact with the part around an elbow and thus allows further increase in venous return.

The cylindrical bandage 1 according to the present embodiment described above is worn on the leg and the foot. In this cylindrical bandage 1, the first tubular knit 10 is knitted on the basis of the human body circumference date $m_0, m_1, m_2, m_3, \ldots m_6$, and $m_7$ corresponding one-to-one to the human body position date $L_0, L_1, L_2, L_3, \ldots L_6$, and $L_7$ and is of a length corresponding to that of the leg while the second tubular knit 20 is knitted on the basis of the human body circumference date $m_8, m_9$, and $m_{10}$, or $m_9$ and $m_{10}$ corresponding one-to-one to the human body position date $L_8, L_9$, and $L_{10}$, or $L_9$ and $L_{10}$ and is of a length corresponding to that of the foot. Between the first tubular knit 10 and the second tubular knit 20, the heel knit 30 is knitted to correspond to the heel. This heel knit 30 is round to correspond to round shapes of the heel.

In some embodiments, the round heel knit 30 may be omitted depending on target body parts (such as arms, legs, heads, foots, and hands) to be covered with the cylindrical bandage 1 or the purpose of the use of the cylindrical bandage 1. Any distinction between the first tubular knit 10 and the second tubular knit 20 may not be made. That is, the cylindrical bandage 1 may have a continuous straight-line as a whole. In this case, the wale stitch numbers of the cylindrical bandage 1 as a whole are again be determined in accordance with the human body circumference date $m_0$, $m_1, m_2, m_3, \ldots$ corresponding one-to-one to the human body position date $L_0, L_1, L_2, L_3, \ldots$ and Young's modulus determined in accordance with the human body position date $L_0, L_1, L_2, L_3, \ldots$. This allows the cylindrical bandage 1 to provide desired compression as a whole.

As described above, the cylindrical bandage 1 including the tubular knit M and the gutter-shaped knit N according to the present embodiment has the first tubular knit 10 and the second tubular knit 20 contiguous with the first tubular knit 10. These first tubular knit 10 and second tubular knit 20 are knitted in accordance with the human body circumference date $m_0, m_1, m_2, m_3, \ldots$ corresponding one to one to the human body position date $L_0, L_1, L_2, L_3, \ldots L_6$ across the longitudinal direction of the target body part to be covered with the cylindrical bandage 1. The wale stitch numbers of the base structure of the first tubular knit 10 and the second tubular knit 20 approximate the calculations based on the human body circumference date $m_0, m_1, m_2, m_3, \ldots$ corresponding one-to-one to the human body position date $L_0, L_1, L_2, L_3, \ldots$ and Young's modulus determined in accordance with the human body position date $L_0, L_1, L_2, L_3, \ldots$. This cylindrical bandage 1 is knitted by flat knitting.

In the cylindrical bandage 1 including the tubular knit M and the gutter-shaped knit N according to the present embodiment, the first tubular knit 10 and the second tubular knit 20 contiguous with the first tubular knit 10 are knitted in accordance with the human body circumference date $m_0$, $m_1, m_2, m_3, \ldots$, which corresponds one-to-one to the human body position date $L_0, L_1, L_2, L_3, \ldots L_6$ across the longitudinal direction of a target body part to be covered with the cylindrical bandage 1. The wale stitch numbers of the base structure of the first tubular knit 10 and the second tubular knit 20 approximate the calculations based on the human body circumference date $m_0, m_1, m_2, m_3, \ldots$ corresponding one-to-one to the human body position date $L_0, L_1, L_2, L_3, \ldots$ and Young's modulus determined in accordance with the human body position date $L_0, L_1, L_2, L_3, \ldots$. Thus, the cylindrical bandage 1, which extends along the longitudinal direction of the body part, has the varying numbers of the wales in accordance with the human body circumference date $m_0, m_1, m_2, m_3, \ldots$, or in accordance with the varying circumferences of the target body part. This cylindrical bandage 1 has the inner surface with alternate ribs and grooves, or alternate inner protuberances 41 and outer protuberances 42. The ribs and grooves, or the inner protuberances 41 and outer protuberances 42 on the inner surface, which will get in direct contact with the target skin, extend longitudinally. The alternate ribs and grooves, or the alternate inner protuberances 41 and outer protuberances 42 make a waveform on the inner surface viewed in cross-section.

The cylindrical bandage 1 according to the present embodiment described above has the varying numbers of the wales in accordance with the varying circumferences of a target body part, or the human body circumference date $m_0$, $m_1, m_2, m_3, \ldots$ corresponding one-to-one to the human body position date $L_0, L_1, L_2, L_3, \ldots$ across the longitudinal direction of the target body part. Such a cylindrical bandage 1 has the varying circumferences, which result from the varying numbers of the wales. The cylindrical bandage 1 has the inner surface with the alternate ribs and grooves. That is, the inner surface, which will get in direct contact with the target skin, has a waveform, viewed in cross-section.

The human body circumference date $m_0, m_1, m_2$, $m_3, \ldots$ represents measured circumferences of the human body position date $L_0, L_1, L_2, L_3, \ldots$. That is, it represents the varying circumferences of a target body part. The number of wales is determined in accordance with the human body circumference date $m_0, m_1, m_2, m_3, \ldots$.

The number of the wales or the number of consecutive rows of connected loops varies in accordance with the varying circumferences of the target body part. The varying numbers of the wales are determined using the human body circumference date $m_0, m_1, m_2, m_3, \ldots$ and Young's modulus determined in accordance with the human body position date $L_0, L_1, L_2, L_3, \ldots$. Thus, the varying circumferences of the target body are reflected in the varying numbers of the wales. The number of the wales is determined using approximation calculated on the basis of Young's modulus determined in accordance with the human body position date $L_0, L_1, L_2, L_3, \ldots$.

Thus, the number of the wales is determined in accordance with approximation calculated using Young's modulus determined in accordance with the human body position date $L_0, L_1, L_2, L_3, \ldots$. The varying circumferences of the target body or the human body circumference date $m_0, m_1$, $m_2, m_3, \ldots$ is reflected in the varying numbers of the wales or the number of consecutive loops of each row.

The varying numbers of the wales, which are determined in accordance with the human body circumference date $m_0$, $m_1, m_2, m_3, \ldots$ corresponding one-to-one to the human body position date $L_0, L_1, L_2, L_3, \ldots$ and Young's modulus, make the varying circumferences.

The number of the wales is set to approximation calculated using Young's modulus determined in accordance with the human body position date $L_0, L_1, L_2, L_3, \ldots$. The values of the calculation for determining the number of the stitches may be rounded off, down, or up, the choice of which may be determined by the yarn properties, knitting patterns, stitches, or body parts to be worn. The number of the wales approximates the values of the calculation based on the human body circumference date $m_0, m_1, m_2, m_3, \ldots$. The difference between the approximation and the calculation is within 1 in number.

The cylindrical bandage 1 according to the present embodiment described above is knitted by flat knitting using flat knitting machined. In the cylindrical bandage 1, the first tubular knit 10 and the second tubular knit 20 have the varying numbers of the wales to correspond to the varying circumferences of a target body part. Varying the numbers of the wales in accordance with the varying cross-sections of the target body part makes the varying circumferences and desired dimensions and shapes. That is, it can make the optimal diameters or circumferences suited to the dimensions and shapes of the target body part easily. Varying the numbers of the wales easily makes desired compression.

Such a cylindrical bandage 1 fits tightly around the ankle with large varying dimensions. This cylindrical bandage 1 does not make looseness or tension derived from too thick or thin a knitted fabric LM. The cylindrical bandage 1 allows the knitted fabric LM to get in intimate contact with even the bottom of the malleolus or the low part around the malleolus. Consequently, the cylindrical bandage 1 provides uniform compression stably. This cylindrical bandage 1 allows the knitted fabric LM to get in intimate contact with even undulating parts or curvy parts with localized edemas. The cylindrical bandage 1 with the varying numbers of the stitches has varying circumferences. Varying the numbers of the stitches can make desired compression with the stitch density fixed. This allows breathability. Further, the cylindrical bandage 1 is easy to put on and taken off.

The cylindrical bandage 1 is not limited to the knitted fabric with seam-free produced on wholegarment knitting machines. The cylindrical bandage 1 may have seams.

The tubular knit M and the gutter-shaped knit N of the cylindrical bandage 1 according to the present embodiment has the inner surface with the alternate ribs and grooves, specifically, the alternate inner protuberances 41 (which appear as raised lines on the inner surface and recesses lines on the outer surface) and outer protuberances 42 (which appear as raised lines on the outer surface and recesses lines on the inner surface). The ribs and grooves, or the inner protuberances 41 and outer protuberances 42 on the inner surface, which will get in direct contact with the target skin, extend longitudinally. The alternate ribs and grooves, or the alternate inner protuberances 41 and outer protuberances 42 make a waveform on the inner surface viewed from cross-section. These ribs and grooves provide the varying degrees of compression in the circumferential direction perpendicular to the longitudinal direction of users when the cylindrical bandage 1 is worn on users. The varying degrees of compression, or weak and strong pressure allows increase in lymph circulation or lymph flow and venous return. In particular, the ribs and grooves extending longitudinally run along the direction of lymph flow. This allows further increase in lymph circulation or lymph flow and venous return. Additionally, this cylindrical bandage 1 does not provide strangeness resulting from compression concentration. Furthermore, the knitted fabric LM of the cylindrical bandage 1 has the uneven inner surface with ribs and grooves. Such a knitted fabric LM easily gets in intimate contact with even undulating parts or curvy parts of a body part and fit tightly to them.

Thus, the cylindrical bandage 1 tightly fits to even undulating parts or curvy parts of a body part. In particular, the knitted fabric LM, which will get in direct contact with the target skin, has the alternate ribs and grooves extending longitudinally. The cross-section of the knitted fabric LM has a wave form. This enhances venous return effectiveness and achieve further increase in venous return.

The cylindrical bandage 1 including the tubular knit M and the gutter-shaped knit N according to the present embodiment has the base structure of the rib stitches of the base yarn A. This base structure includes the knit stitches of the elastic yarn B in the outer protuberances 42 and the miss or tuck stitches of the elastic yarn B in inner protuberances 41. The stitch row of the base yarn A alternates with the stitch row of the elastic yarn B. This results in higher annual tension of the outer than the inner, which will get in direct contact with the target skin. Thus, the cylindrical bandage 1 has the outer with higher annual tension than the inner, which will get in direct contact with the target skin.

Such a cylindrical bandage 1 has large height gap between the ribs or the inner protuberances 41 (which appear as raised lines on the inner surface and recesses lines on the outer surface) and the grooves or the outer protuberances 42 (which appear as raised lines on the outer surface and recesses lines on the inner surface). The inner protuberances 41 on the inner surface, which will get in direct contact with the target skin, is rounder and higher than outer protuberances 42 on the outer surface. This enables the inner protuberances 41 on the inner surface to more closely approach the skin and increase in compression.

In the cylindrical bandage 1 according to the present embodiment, the base structure of the rib stitches of the base yarn A includes the knit stitches of the elastic yarn B and the miss or tuck stitches of the elastic yarn B. This makes varying tensions in the circumferential direction. The inner surface, which will get in direct contact with the target skin, has difference in tension between the ribs or the inner protuberances 41 (which appear as raised lines on the inner surface and recesses lines on the outer surface) and the grooves or the outer protuberances 42 (which appear as raised lines on the outer surface and recesses lines on the inner surface). Thus, the cylindrical bandage 1 has difference in tension between the ribs and grooves on the inner surface, which will get in direct contact with the target skin.

Such a cylindrical bandage 1 has large height gap between the ribs or the inner protuberances 41 (which appear as raised lines on the inner surface and recesses lines on the outer surface) and the grooves or the outer protuberances 42 (which appear as raised lines on the outer surface and recesses lines on the inner surface). The inner protuberances 41 on the inner surface, which will get in direct contact with the target skin, is rounder and higher than outer protuberances 42 on the outer surface. This enables the inner protuberances 41 on the inner surface to more closely approach the skin and increase in compression.

The cylindrical bandage 1 including the tubular knit M and the gutter-shaped knit N according to the present embodiment has the first tubular knit 10 and the second tubular knit 20 with the rib base structure. Thus, the knitted fabric LM has the front and back surfaces with the alternate ribs and grooves or the alternate outer protuberances 42 and inner protuberances 41, which extend longitudinally. The cross-section has the alternate ribs and grooves in the circumferential direction and a wave shape. The raised lines on the inner surface, which will get in direct contact with the target skin, appear as the recess lines on the outer surface while the recess lines on the inner surface appear as the raised lines on the outer surface. The inner protuberances 41 appear as the raised lines on the inner surface and as the recess lines on the outer surface while the outer protuberances 42 appear as the recess lines on the inner surface and as the raised lines on the outer surface. The cylindrical bandage 1 has the inner protuberances 41 that is rounder than the outer protuberances 42.

In the cylindrical bandage 1 including the tubular knit M and the gutter-shaped knit N according to the present embodiment, the first tubular knit 10 and the second tubular knit 20 contiguous with it are knitted in accordance with the human body circumference date $m_0$, $m_1$, $m_2$, $m_3$, . . . corresponding one-to-one to the human body position date $L_0$, $L_1$, $L_2$, $L_3$, . . . across the longitudinal direction of a target body part. The wale stitch numbers of the first tubular knit 10 and the second tubular knit 20 is determined in accordance with approximation calculated using Young's modulus determined in accordance with the human body position date $L_0$, $L_1$, $L_2$, $L_3$, . . . . The varying numbers of the wales corresponds to the varying circumferences of the target body or the human body circumference date $m_0$, $m_1$, $m_2$, $m_3$, . . . . In this cylindrical bandage 1, which extends longitudinally along the longitudinal direction of a body part, the knitted fabric LM has the front and back surfaces with the alternate ribs and grooves which extend longitudinally. Viewed from cross-section, the ribs alternate with grooves in the circumferential direction, thus forming a wave shape. The raised lines on the inner surface, which will get in direct contact with the target skin, appear as the recess lines on the outer surface while the recess lines on the inner surface appear as the raised lines on the outer surface. The inner protuberances 41 appear as the raised lines on the inner surface and as the recess lines on the outer surface while the outer protuberances 42 appear as the recess lines on the inner surface and as the raised lines on the outer surface. The cylindrical bandage 1 has the inner protuberances 41 that is rounder than the outer protuberances 42.

In the cylindrical bandage 1 including the tubular knit M and the gutter-shaped knit N according to the present embodiment, the first tubular knit 10 and the second tubular knit 20 have the varying numbers of the wales to reflect the varying circumferences or the varying dimensions and shapes of a target body part. Varying the numbers of the wales for in accordance with the varying cross-sections of the target body part makes the varying circumferences and provides desired dimensions and shapes. That is, it makes the optimal diameters or circumferences suited to the dimensions and shapes of the target body easily. Additionally, desired compression is easily made by referring to the number of stitches and Young's modulus. The cylindrical bandage 1 worn on, for example, the legs fits tightly around the ankle with large varying circumferences. The cylindrical bandage 1 is not too thick or thin and thus is not loose or tense. The cylindrical bandage 1 allows the knitted fabric LM to get intimate contact with even the bottom of the malleolus or the low part around the malleolus. Consequently, the cylindrical bandage 1 provides uniform compression stably. The cylindrical bandage 1 also allows the knitted fabric LM to get intimate contact with even undulating parts or curvy parts with localized edemas. Varying the numbers of the stitches or the varying circumferences makes desired compression with the stitch density fixed. Thus, breathability is allowed. The cylindrical bandage 1 is easily put on or taken off The knitted fabric LM has the inside and outer surfaces with the alternate ribs and grooves, specifically, the alternate outer protuberances 42 and inner protuberances 41, which extend longitudinally. The cross-section of the knitted fabric LM has the alternate ribs and grooves or the alternate inner protuberances 41 and outer protuberances 42 in the circumferential direction and has a waveform. These ribs and grooves make the varying degrees of compression in the circumferential direction perpendicular to the longitudinal direction of users when the cylindrical bandage 1 is worn on users. The varying degrees of compression, or weak and strong pressure allows increase in lymph circulation or lymph flow and venous return. In particular, the ribs and grooves extending longitudinally run along the direction of lymph flow. This allows further increase in lymph circulation or lymph flow and venous return. Additionally, this cylindrical bandage 1 does not provide discomfort with compression concentration.

The base structure of the rib stitches of the base yarn A includes the knit stitches of the elastic yarn B in the outer protuberances 42 and the miss or tuck stitches of the elastic yarn B in inner protuberances 41. The stitch row of the base yarn A alternates with the stitch row of the elastic yarn B. As a result, the inner protuberances 41 on the inner surface are rounder than the outer protuberances 42 on the outer surface and has a curve shape or arch in cross-section. This provides high cushioning of the inner protuberances 41 and closer contact of the inner protuberances 41 to a target body part. This allows increase in compression.

Furthermore, the knitted fabric LM has the uneven inner surface with ribs and grooves. Such a knitted fabric LM easily gets in intimate contact with even undulating parts or curvy parts of a body part and fit tightly to them.

Thus, the cylindrical bandage 1 achieves tight fitting for the varying cross-sections of a body part. In particular, the knitted fabric LM, which will get in direct contact with the target skin, has the alternate ribs and grooves extending longitudinally. The cross-section of the knitted fabric LM has the alternate ribs and grooves in the circumferential direction and has a waveform. This enhances venous return effectiveness and achieve further increase in venous return.

The cylindrical bandage 1 including the tubular knit M and the gutter-shaped knit N according to the present embodiment described above includes the heel knit 30 with the predetermined number of the courses. between the first tubular knit 10 and the second tubular knit 20. The circumference or the diameter of the lengthwise end of the second tubular knit 20 contiguous with the first tubular knit 10 and the heel knit 30 is larger than that of the lengthwise end of the first tubular knit 10 contiguous with the second tubular knit 20 and the heel knit 30. With the cylindrical bandage 1 folded along the front symmetrical line $d_1$ and the back symmetrical line $d_2$ dividing wales in tow, the ratio of the length a to the length b is in a range of 6:4 to 9:1. The length a is a length of the virtual perpendicular line $c_1$ connecting between the front symmetrical line $d_1$ and the border P between the first tubular knit 10, the second tubular knit 20 and the heel knit 30, and the length b is a length of the virtual perpendicular line $c_2$ connecting between the back symmetrical line $d_2$ and the border P.

In the cylindrical bandage 1 including the tubular knit M and the gutter-shaped knit N according to the present embodiment described above, the circumference or the diameter of the lengthwise top end of the second tubular knit 20 contiguous with the first tubular knit 10 is larger than that of the lengthwise bottom end of the first tubular knit 10 contiguous with the second tubular knit 20 and the heel knit 30.

In the present embodiment described above, the first tubular knit 10 and the second tubular knit 20 has the varying circumferences with the varying numbers of stitches. Since the difference in the number of the stitches between the first row of the second tubular knit 20 and the last row of the first tubular knit 10, the circumference or the diameter of the first row of the second tubular knit 20 contiguous with the first tubular knit 10 is larger than that of the last row of the first tubular knit 10 contiguous with the second tubular knit 20. Varying stitch density, knitting pattern or tension may make the varying circumferences.

In the cylindrical bandage 1 according to the present embodiment described above, the first tubular knit 10 and the second tubular knit 20 of the tubular knit M are partially connected by the heel knit 30 with the predetermined number of the rows. The heel knit 30 lies between the first tubular knit 10 and the second tubular knit 20, in which the width widens from the first tubular knit 10 to the second tubular knit 20.

Thus, the first tubular knit 10 and the second tubular knit 20 are partially connected by the heel knit 30. In particular, with the cylindrical bandage 1 folded along the front symmetrical line $d_1$ and the back symmetrical line $d_2$ dividing wales in tow, the ratio of the length a to the length b is in a range of 6:4 to 9:1. The length a is a length of the virtual perpendicular line $c_1$ connecting between the front symmetrical line $d_1$ and the border P between the first tubular knit 10, the second tubular knit 20 and the heel knit 30, and the length b is a length of the virtual perpendicular line $c_2$ connecting between the back symmetrical line $d_2$ and the border P.

In the cylindrical bandage 1 according to the present embodiment described above, the circumference or the diameter of the end of the second tubular knit 20 contiguous with the first tubular knit 10 is larger than that of the end of the first tubular knit 10 contiguous with the second tubular knit 20. The first tubular knit 10 and the second tubular knit 20 are connected by the rounder heel knit 30 with the predetermined number of the courses. The presence of the rounder heel knit 30 prevents the knitted fabric LM from having wrinkles on the back of an ankle and high tension on a heel when the cylindrical bandage 1 is worn. The heel knit 30 achieves tight fitting for the shapes of a heel. The end of the second tubular knit 20 contiguous with the first tubular knit 10 has larger circumference or the diameter than the end of the first tubular knit 10. The circumference or the diameter of the second tubular knit 20 varies from that of the first tubular knit 10. This allows the heel knit 30 to have larger curvature to fit the round shapes of the heel and to fail to strongly tighten the heel. Additionally, desired circumference or the diameter to fit the ankle is allowed. Looseness and wrinkles, which result from larger dimensions of the knitted fabric LM on the instep of the foot, are prevented. Thus, decrease in venous return with horizontal wrinkles biting is prevented. High tension, which results from smaller dimensions of the knitted fabric LM on the heel, is also prevented.

With the cylindrical bandage 1 folded along the front symmetrical line $d_1$ and the back symmetrical line $d_2$ dividing wales in tow, the ratio of the length a to the length b is in a range of 6:4 to 9:1. The length a is a length of the virtual perpendicular line $c_1$ connecting between the front symmetrical line $d_1$ and the border P between the first tubular knit 10, the second tubular knit 20 and the heel knit 30, and the length b is a length of the virtual perpendicular line $c_2$ connecting between the back symmetrical line $d_2$ and the border P. Consequently, the part around the malleolus including the medial malleolus and the lateral malleolus is covered with not the round heel knit 30 with the predetermined number of stitches or courses but the first tubular knit 10 and the second tubular knit 20 with predetermined elasticity or Young's modulus allowing for uniform compression.

Thus, looseness and wrinkles on the heel and high tension on the heel, are prevented. The undulation parts around the malleolus is covered with the first tubular knit 10 and the second tubular knit 20 with no curvature. This prevents the knitted fabric LM from fitting loosely to the undulation parts around the malleolus and allows the knitted fabric LM to fit tightly to the undulation parts around the malleolus. In particular, the knitted fabric LM fits tightly to even the back lower part around the malleolus. Thus, the knitted fabric LM provides stable or uniform compression to even undulation parts around the malleolus. The knitted fabric LM also fits tightly to the undulation parts with localized edema.

Thus, the cylindrical bandage 1 fits tightly to even the ankle part including the hell, the malleolus and bending part between the instep of the foot and the bottom of the leg. The cylindrical bandage 1 provides stable compression with uniform distribution to even such an ankle part with larger varying dimensions in cross-section.

The heel knit 30 is preferably contiguous with 10 to 40%, more preferably, 20 to 40% of the circumference of the last stitch row of the first tubular knit 10 and is preferably contiguous with 10 to 40%, more preferably, 20 to 40% of the circumference of the first stitch row of the second tubular knit 20. This prevents the first tubular knit 10 and the second tubular knit 20 from being pulled by the heel and having high tension and looseness when the cylindrical bandage 1 is worn and covers the part around the ankle. Thus, the first tubular knit 10 and the second tubular knit 20 fit tightly to the undulation parts around the malleolus.

In the cylindrical bandage 1 according to the present embodiment described above, the first tubular knit 10 and the second tubular knit 20 has the inner surface with the alternate ribs and grooves, specifically, the alternate inner protuberances 41 and outer protuberances 42. The inner protuberances 41 appears as raised lines on the inner surface and recesses lines on the outer surface. The outer protuberances 42 appears as raised lines on the outer surface and recesses lines on the inner surface. The circumferentially continuous ribs and grooves, or the continuous inner protuberances 41 and outer protuberances 42 on the inner surface, which will get in direct contact with the target skin, extend longitudinally. The alternate ribs and grooves, or the alternate inner protuberances 41 and outer protuberances 42 make a waveform in cross-section. Such a first tubular knit 10 and a second tubular knit 20 covers the foot part in range from the instep to the malleolus and fit tightly even to the undulation parts around the malleolus when the cylindrical bandage 1 is worn on the part around ankle. This increases venous return promoting effect. Thus, the undulation parts around the malleolus is covered with the first tubular knit 10 and a second tubular knit 20 when the cylindrical bandage 1 is worn. The first tubular knit 10 and a second tubular knit 20 fit tightly to the undulation parts around the malleolus. This yields higher compression and increases venous return promoting effect. Additionally, the first tubular knit 10 and a second tubular knit 20, which fit tightly to the undulation parts around the malleolus, has the inner surface with the alternate ribs and grooves, specifically, the alternate inner protuberances 41 and outer protuberances 42, which extends longitudinally. This increases lymph flow at the malleolus part with rich lymph and further increases in venous return promoting effect.

The cylindrical bandage 1 has the varying circumferences resulting from the varying numbers of wales to correspond to the varying cross-sections of the target body part. In the cylindrical bandage 1, the inner surface, which will get in direct contact with the target skin, has the alternate continuous ribs and grooves that make a waveform in cross-section perpendicular to the longitudinal direction.

The wales are vertical columns of loops while the courses are horizontal rows of loops in the knitted fabric LM.

Examples of the yarn used for knitting the knitted fabric LM includes spun yarns, filament yarns, monofilament yarns, bulky yarns, hollow yarns, covering yarns, core yarns, composite yarns, flat yarns, modified cross-section yarns, split yarns, and lacquer yarns. The yarn may be made from, for example, chemical materials, metals, plant materials, or twist yarns in which above materials may be used in combination.

The varying circumferences resulting from the varying numbers of wales means that varying the number of the consecutive loops of each row yields the varying circumferences corresponding to the varying cross-sections perpendicular to the longitudinal direction of the target body part.

The circumferentially continuous ribs and grooves that make a waveform in cross-section means that the ribs appearing as raised parts on the inner surface of the cylindrical bandage 1 alternate with the grooves appearing as fallen parts on the inner surface in the circumference direction and the cross-section the cylindrical bandage 1 has a repetitive waveform of the inner surface. The ribs and grooves may be formed by rib or tuck knitting.

In the cylindrical bandage 1, Varying the numbers of wales across the length of the cylindrical bandage 1 makes the varying circumferences corresponding to the varying cross-sections of the body part. This provides desired circumference, dimensions and shapes. That is, varying numbers of wales with fixed stitch density makes the optimal diameters or circumferences suited to the dimensions and shapes of the target body easily. Such a cylindrical bandage 1 fits tightly to even the part around ankle with the large varying circumferences. The cylindrical bandage 1 is not too thin or thick and thus less likely to be loose and wrinkle or to be tense. The cylindrical bandage 1 allows the knitted fabric LM to get intimate contact with even the bottom of the malleolus or the low part around the malleolus. Consequently, the cylindrical bandage 1 provides uniform compression stably. Varying the numbers of the stitches or varying circumference makes desired stretch with the stitch density fixed. Thus, breathability is allowed. The cylindrical bandage 1 is easily put on and taken off.

The inner surface, which will get in direct contact with the target skin, has the alternate ribs and grooves that are circumferentially continuous and make a waveform in cross-section. These ribs and grooves yield the varying degrees of compression across the circumference direction perpendicular to the longitudinal direction of the user's body part. The varying degrees of compression allows increase in lymph flow and venous return, provide balanced compression, and eliminate strangeness caused by compression concentration.

Thus, the cylindrical bandage 1 achieves tight fitting for the varying cross-sections of the body part. In particular, the knitted fabric LM, which will get in direct contact with the target skin, has the circumferentially continuous ribs and grooves giving a waveform in cross-section. This increase in venous return effectiveness and is highly effective for venous return.

In the cylindrical bandage 1 according to the present embodiment described above, the ribs and grooves extend longitudinally. Thus, the ribs and grooves making the varying degrees of compression extends along lymph flow. This increases lymph circulation further and venous return effectiveness.

The cylindrical bandage 1 according to the present embodiment described above has the outer with higher tension of the circumferential direction than the inner, which will get in direct contact with the target skin.

In this cylindrical bandage 1, the tension of the circumferential direction of the outer is higher than that of the inner, which will get in direct contact with the target skin. As a result, the ribs on the inner surface, which will get in direct contact with the target skin, is rounder and higher than the ribs on the outer surface. This enables the ribs on the inner surface to get in more closely contact with the skin and increases in compression.

The cylindrical bandage 1 according to the present embodiment described above has the difference in the tension of the circumferential direction between the ribs and grooves on the inner, which will get in direct contact with the target skin.

Thus, the ribs and grooves on the inner of the cylindrical bandage 1 differ in the tension of the circumferential direction. The difference in the tension yields the rounder and higher ribs on the inner surface which will get in direct contact with the target skin. This enables the ribs on the inner surface to get in more closely contact with the skin and increases in compression.

The cylindrical bandage 1 including the tubular knit M and the gutter-shaped knit N according to the present embodiment has the varying numbers of the wales and thus have the varying circumferences to correspond to the varying cross-sections of a target body part. This cylindrical bandage 1 has the knitted fabric LM with alternate ribs and grooves on the both surfaces. The ribs alternate with the grooves in the circumferential direction perpendicular to the length direction. With the alternate ribs and grooves, the cross-section of the cylindrical bandage 1 has wave forms. The inner protuberances that appear as the raised lines on the inner surface and recess lines on the outer surface is rounder than the outer protuberances 42 that appear as the raised lines on the outer surface and recess lines on the inner surface, which will get in direct contact with a target skin.

The wales are vertical columns of loops while the courses are horizontal rows of loops in the knitted fabric LM.

Examples of the yarn used for knitting the knitted fabric LM includes spun yarns, filament yarns, monofilament yarns, bulky yarns, hollow yarns, covering yarns, core yarns, composite yarns, flat yarns, modified cross-section yarns, split yarns, and lacquer yarns. The yarn may be made from, for example, chemical materials, metals, plant materials, or twist yarns in which above materials may be used in combination.

The varying circumferences resulting from the varying numbers of wales means that varying the number of the consecutive loops of each row yields the varying circumferences corresponding to the varying cross-sections perpendicular to the longitudinal direction of the target body part.

The circumferentially continuous ribs and grooves that make a waveform in cross-section means that the ribs alternate with the grooves in the circumference of the both surfaces and the cross-section of the cylindrical bandage has a repetitive waveform. The ribs and grooves may be formed by rib or tuck knitting.

The inner protuberances appearing as the raised stitches on the inner surface, which will get in direct contact with a target skin, are rounder than the outer protuberances appearing as the raised stitches on the outer surface. This means that the inner protuberances on the inner surface have higher curvature than the outer protuberances have, viewed from cross-section of the cylindrical bandage.

In the cylindrical bandage 1, varying numbers of wales across the length of the cylindrical bandage 1 makes the varying circumferences corresponding to the varying cross-sections of the body part. This provides desired circumference, dimensions and shapes. That is, varying numbers of wales with fixed stitch density makes the optimal diameters or circumferences suited to the dimensions and shapes of the target body easily. Such a cylindrical bandage 1 fits tightly to even the part around ankle with the large varying circumferences. The cylindrical bandage 1 is not too thin or thick and thus is likely to make looseness, wrinkles, or tenseness. The cylindrical bandage 1 allows the knitted fabric LM to get intimate contact with even the bottom of the malleolus or the low part around the malleolus. Consequently, the cylindrical bandage 1 provides uniform compression stably. Varying the numbers of the stitches or the varying the circumferences makes desired stretch with the stitch density fixed. Thus, breathability is allowed. The cylindrical bandage 1 is easily put on and taken off.

The knitted fabric LM has the inner and outer surfaces with the alternate ribs and grooves that are circumferentially continuous and make a waveform in cross-section. These ribs and grooves yield the varying degrees of compression across the circumference direction perpendicular to the longitudinal direction of the user's body part. The varying degrees of compression allows increase in lymph flow and venous return, provide balanced compression, and eliminate discomfort.

The inner protuberances 41 that appear as the raised lines on the inner surface and recess lines on the outer surface is rounder than the outer protuberances 42 that appear as the raised lines on the outer surface and recess lines on the inner surface, which will get in direct contact with a target skin. This allows the inner protuberances 41 to get in closer contact with a target body part and provide higher compression.

Thus, the cylindrical bandage achieves tight fitting for the varying cross-sections of a body part. Further, the knitted fabric LM, which will get in direct contact with the target skin, has the alternate ribs and grooves extending longitudinally. The cross-section of the knitted fabric LM has the alternate ribs and grooves in the circumferential direction and has a waveform. This allows further increase in venous return.

The cylindrical bandage of the present embodiment has the inner protuberances 41 extending longitudinally and the outer protuberances 42 extending longitudinally.

Thus, the inner protuberances 41 and the outer protuberances 42 of the cylindrical bandage extend longitudinally. Such inner protuberances 41 and the outer protuberances 42 run along lymph flow. This allows further increase in lymph and venous return.

The cylindrical bandage of the present embodiment has the knitted fabric LM with a thickness in range of 2 to 15 mm, preferably, 5 to 15 mm when non-stretched.

The cylindrical bandage has the knitted fabric LM with a cross-sectional thickness in range of 2 to 15 mm. Such a knitted fabric LM does not wrinkle easily even on movement or bend parts (for example, the instep side of a foot) when worn. Thus, compression concentration and tourniquet with wrinkles biting is prevented.

The cylindrical bandage 1 according to the present embodiment described above achieves 20 to 45 mmHg, preferably 15 to 50 mmHg, more preferably 20 to 45 mmHg compression on the bottom of a lateral malleolus near the heel when worn on the part around ankle. These compression values are measurement of the compression on the human left foot mold wearing the cylindrical bandage 1 according to the embodiment. As the human left foot, men's five-toed socks for display (TENKENSOUI, Co., Ltd. 51-196-10-2) is used. The compression is measured by using air pack type close contact surface pressure measuring system (made by AMI TECHNO, Inc. AMI3037-SB-SET).

The measured position of the bottom of the lateral malleolus near the heel corresponds to the almost flat part at the back bottom of the raised lateral malleolus.

The values described above allow for margin of error in measurement.

The cylindrical bandage 1 according to the present embodiment described above achieves provision of 3 to 70 mmHg compression on the bottom of a lateral malleolus near the heel when worn on the part around ankle.

With the compression less than these values, the cylindrical bandage 1 may fail to increase venous return. With the compression more than these values, the cylindrical bandage 1 may adversely affect venous return. The cylindrical bandage 1 according to the present embodiment eliminates wrinkles and tenseness in the knitted fabric LM and fit tightly to the part around ankle. It is difficult for conventional case to achieve high compression on the bottom around a malleolus. However, this cylindrical bandage 1 fits tightly to the bottom around a malleolus and achieves higher compression, specifically 15 mmHg or more compression on even the bottom around a malleolus, especially the bottom around a lateral malleolus near the heel than in the conventional case. This yields further increase in venous return. With the compression on a lateral malleolus near the heel 15 mmHg or more, the cylindrical bandage 1 fits tightly and increases venous return further. It is note that higher compression may cause pain, skin damage, skin laceration and skin tears to some serious skin. With the compression in a range of 3 to 70 mmHg, the cylindrical bandage 1 increases venous return without causing pain, skin damage, skin laceration and skin tears and increases venous return in the lower limb. With the preferred compression in a range of 5 to 60 mmHg, more preferably, 15 to 50 mmHg, the cylindrical bandage 1 provides comfortable fit and is highly effectiveness for promoting venous return and for reducing swelling or edema on the part around ankle, especially, the malleolus and the back of the ankle, in which excess lymph is trapped.

The cylindrical bandage 1 according to the present embodiment described above achieves the 40% or less, preferably, 30% or less, more preferably, 10% or less difference in the compression on the bottom of a lateral malleolus near the heel and the instep of the foot when worn on the part around ankle.

These compression values are measurement of the compression on the human left foot mold wearing the cylindrical bandage 1 according to the embodiment. As the human left foot, men's five-toed socks for display (TENKENSOUI, Co., Ltd. 51-196-10-2) is used. The compression is measured by using air pack type close contact surface pressure measuring system (made by AMI TECHNO, Inc. AM13037-SB-SET).

The measured position of the bottom of the lateral malleolus near the heel corresponds to the almost flat part at the back bottom of the raised lateral malleolus.

The measured position of the instep of the foot corresponds to the front middle part of the instep above the top of a plantar arch.

The values described above allow for margin of error in measurement.

The cylindrical bandage 1 according to the present embodiment described above achieves the 40% or less difference in the compression on the bottom of a lateral malleolus near the heel and the instep of the foot when worn on the part around ankle.

The cylindrical bandage 1 according to the present embodiment eliminates wrinkles and tenseness in the knitted fabric LM and fit tightly to the part around ankle. It is difficult for conventional case to provide high compression on the bottom around a malleolus. However, this cylindrical bandage 1 fits tightly to the bottom around a malleolus and achieves higher compression, specifically 15 mmHg or more compression on even the bottom around a malleolus, especially the bottom around a lateral malleolus near the heel than in the conventional case. The cylindrical bandage 1 achieves the 40% or less difference in the compression on the bottom of a lateral malleolus near the heel and the instep of the foot. The cylindrical bandage 1 achieves higher compression on the part around the malleolus, in which excess lymph is trapped, and achieves the 40% or less difference in the compression on the bottom of a lateral malleolus near the heel and the instep of the foot. Thus, the cylindrical bandage 1 eliminates compression concentration and achieves stable and uniform compression on the part around ankle. This yields further increase in venous return in the lower limb and further decrease in swelling or edema on the part around ankle, especially, the malleolus and the back of the ankle, in which excess lymph is trapped. With the preferred difference in the compression on the bottom of a lateral malleolus near the heel and the instep of the foot 30% or less, more preferably, 10% or less, the cylindrical bandage 1 provides stable compression and achieve further increase in venous return.

In the embodiment described above, the cylindrical bandage 1 is used as a supporter worn on the lower limb of a human body. A body part wearing the cylindrical bandage 1 is not limited to a leg and a foot. The cylindrical bandage 1 may be worn on limbs or trunk, such as arms, wrists, hands, or a head. In some embodiments, the cylindrical bandage 1 may be used as a bandage, a supporter, a sleeve including a compression sleeve, or a glove including a compression glove. The cylindrical bandage 1 worn on wrists or hands may be undercut to form a hole between the first tubular knit 10 and the second tubular knit 20, or at the border with difference in circumferences. In this case, the thumb of a hand is put through the hole. Thus, the first tubular knit 10 covers a hand mainly while the second tubular knit 20 covers wrists side. This cylindrical bandage can fit for the hand with varying cross-sections.

As described above, the cylindrical bandage 1 according to the embodiment of the present invention includes the tubular knit M with a length corresponding to the length of the arm or the leg and the gutter-shaped knit N extending from the first end of the tubular knit M. The gutter-shaped knit N has a smaller length in the circumferential direction than the first end of the tubular knit M and has a gutter-shape. This gutter-shaped knit M has a cut-out section giving it a horseshoe or V shape. The tubular knit M has a base structure formed of the stitches of the base yarn A, viewed from cross-section perpendicular to the length direction of the arm or the leg. The base structure includes the stitches of the elastic yarn B. The elastic yarn B, which has higher elasticity than the base yarn A, hides behind the base yarn A in the inner protuberances 41 to avoid contact with the skin of users.

Thus, the gutter-shaped knit N extends from the first end of the tubular knit M. This gutter-shaped knit N has a smaller length in the circumferential direction than the first end of the tubular knit M and has a horseshoe or C shape in cross-section. The gutter-shaped knit M has a horseshoe or V shaped edge. Such a gutter-shaped knit M stably holds a shoulder including collarbones while allowing shoulder movements on the inside. This prevents the cylindrical bandage 1 from falling down or allows the cylindrical bandage 1 to stay on the body part, even when the user wearing the cylindrical bandage 1 rolls over while sleeping.

The gutter-shaped knit N has the horseshoe or V shaped edge, which is made by varying the number of the stitches. The horseshoe or V shaped edge yields tight grasp. This allows the gutter-shaped knit N to stably hold the shoulder including the collarbones.

The number of the stitches of the gutter-shaped knit N varies from that of the tubular knit M. This makes the gutter-shaped knit N with the horseshoe or V shaped edge. The knitting width or the length of the circumferential direction gradually decreases from the tubular knit M to the gutter-shaped knit N with the cut-out section shaped in horseshoe or V. Such a gutter-shaped knit N stands on the tubular knit M and is flexible. Consequently, the cylindrical bandage 1 fits tightly without using binding means such as strings. This cylindrical bandage 1 achieves tight fitting for the varying cross-sections of the body part. The cylindrical bandage 1 is used as a bandage for compression, such as a supporter for lower or upper limb, a sleeve, a stocking, tights, a supporter for elbow, or a supporter for a hand or a wrist. This cylindrical bandage 1 allows increase in venous return and is effectiveness for prevention and treatment of diseases such as venous disorders and lymphedema. In particular, the cylindrical bandage 1 stably stays on the body part.

The gutter-shaped knit N has a middle with the varying numbers of the stitches.

The gutter-shaped knit N extends from the first end of the tubular knit M. This gutter-shaped knit N has a smaller length in the circumferential direction than the first end of the tubular knit M and has a horseshoe or C shape in cross-section. The gutter-shaped knit M has a horseshoe or V shaped edge. Such a gutter-shaped knit M stably holds a shoulder including collarbones while allowing shoulder movements on the inside. This prevents the cylindrical bandage 1 from falling down or allows the cylindrical bandage 1 to stay on the body part, even when the user wearing the cylindrical bandage 1 rolls over while sleeping.

The gutter-shaped knit N has the horseshoe or V shaped edge, which is made by varying the number of the stitches. The horseshoe or V shaped edge yields tight grasp. This allows the gutter-shaped knit N to stably hold the shoulder including the collarbones.

The number of the stitches of the gutter-shaped knit N varies from that of the tubular knit M. This makes the gutter-shaped knit N with the horseshoe or V shaped edge. The knitting width or the length of the circumferential direction gradually decreases from the tubular knit M to the gutter-shaped knit N with the cut-out section shaped in horseshoe or V. Such a gutter-shaped knit N stands on the tubular knit M and is flexible. Consequently, the cylindrical bandage 1 fits tightly without using binding means such as strings. This cylindrical bandage 1 achieves tight fitting for the varying cross-sections of the body part. The cylindrical bandage 1 is used as a bandage for compression, such as a supporter for lower or upper limb, a sleeve, a stocking, tights, a supporter for elbow, or a supporter for a hand or a wrist. This cylindrical bandage 1 allows increase in venous return and is effectiveness for prevention and treatment of diseases such as venous disorders and lymphedema. In particular, the cylindrical bandage 1 stably stays on the body part.

The gutter-shaped knit N contiguous with the tubular knit M is at an angle in range of 30 to 270 to the center line of the tubular knit M In the cylindrical bandage 1 including the tubular knit M and the gutter-shaped knit N according to the present embodiment, the gutter-shaped knit N is contiguous with the tubular knit M. This makes the gutter-shaped knit N standing and eliminates discomfort caused by difference between the gutter-shaped knit N and the tubular knit M.

Thus, the gutter-shaped knit N contiguous with the tubular knit M is at an angle in range of 30 to 2700 to the center line of the tubular knit M. This allows the gutter-shaped knit N to stand and provides desired stiffness. The choose of the angle depends on the dimensions of the target body part. Thus, the angle may not be exactly 30 to 270°.

The gutter-shaped knit N and the tubular knit M have a thickness in range of 2 to 15 mm.

The cylindrical bandage 1 has the gutter-shaped knit N with a thickness in range of 2 to 15 mm and the tubular knit M with a thickness in range of 2 to 15 mm. The cylindrical bandage 1 having the thicker knitted fabric LM of the gutter-shaped knit and the tubular knit keeps its shape. Such a cylindrical bandage 1 is less likely to shift. Additionally, this knitted fabric LM is less likely to create wrinkles even on movement or bend parts (for example, the instep side of a foot) when the cylindrical bandage 1 is worn. Thus, compression concentration and tourniquet with the wrinkles biting is prevented.

The second end of the tubular knit M is placed on the foot part corresponding to metatarsal bones mt or the hand part corresponding to metacarpal bones mc. This prevents the gutter-shaped knit M and the tubular knit N from shifting even when user's weight is put on the knit. The gutter-shaped knit N and the tubular knit M keep fitting.

The gutter-shaped knit N and the tubular knit M, which are continuous in the longitudinally direction, are symmetrical about a center perpendicular line.

Thus, the cylindrical bandage 1 according to the present embodiment includes the gutter-shaped knit N and tubular knit M that are continuous in the longitudinally direction and are symmetrical about a center perpendicular line. Such a symmetrical cylindrical bandage 1 does not shift easily even when a user's weight is put on the knitted fabric and the user's body moves. The gutter-shaped knit N and the tubular knit M keep fitting.

The number of the stitches of the gutter-shaped knit N varies from that of the tubular knit M. This makes the gutter-shaped knit N with the horseshoe or V shaped edge. In particular, the numbers of the stitches may vary with the shapes of a buttock. This allows the gutter-shaped knit N to fit tightly to a user.

REFERENCE SIGNS LIST 1 a cylindrical bandage
M a tubular knit
N a gutter-shaped knit
a first tubular knit
a second tubular knit
a heel knit
41 an inner protuberance
42 an outer protuberance
$L_0, L_1, L_2, L_3, \ldots$ human body position date
$m_0, m_1, m_2, m_3, \ldots$ human body circumference date
A a base yarn
B an elastic yarn
LM a knitted fabric

The invention claimed is:

1. A cylindrical bandage, comprising:
a tubular knit; and
a gutter-shaped knit extending from a lengthwise first end of the tubular knit, the gutter-shaped knit having a smaller length in a circumferential direction than the first end of the tubular knit, the gutter-shaped knit having a variation in a number of wales and a horseshoe-shaped cut-out section at a lateral side of the gutter-shaped knit, wherein the horseshoe-shaped cut-out section has a bottom edge being a lengthwise extension of the tubular knit, and
wherein a top end of the gutter-shaped knit is formed congruently with the bottom edge of the horseshoe-shaped cut-out section.

2. The cylindrical bandage according to claim 1, wherein the gutter-shaped knit has a thickness in a range of 2 to 15 mm and the tubular knit has a thickness in a range of 2 to 15 mm.

3. The cylindrical bandage according to claim 1, wherein the tubular knit has a second end placed on a foot part configured to correspond to metatarsal bones.

4. The cylindrical bandage according to claim 1, wherein the tubular knit has a second end placed on a hand part configured to correspond to metacarpal bones.

5. The cylindrical bandage according to claim 1, wherein the gutter-shaped knit is symmetrical about a center perpendicular line in an extended configuration of the gutter-shaped knit and the tubular knit.

6. The cylindrical bandage according to claim 1, wherein the gutter-shaped knit and the tubular knit have a base structure formed of stitches of a base yarn; and
the base structure includes stitches of an elastic yarn.

7. A cylindrical bandage, comprising:
a tubular knit; and
a gutter-shaped knit extending from a lengthwise first end of the tubular knit, the gutter-shaped knit having a smaller length in a circumferential direction than the first end of the tubular knit, the gutter-shaped knit having a gutter shape and a horseshoe-shaped cut-out section at a lateral side of the gutter-shaped knit, wherein the horseshoe-shaped cut-out section has a bottom edge being a lengthwise extension of the tubular knit, and
wherein a top end of the gutter-shaped knit is formed congruently with the bottom edge of the horseshoe-shaped cut-out section,
wherein the tubular knit and the gutter shaped knit have inner protuberances and outer protuberances extending along a longitudinal direction of the bandage; and
the inner protuberances and outer protuberances have one end on a symmetrical line of the bandage.

8. A cylindrical bandage, comprising:
a tubular knit configured to correspond to a humerus bone, an elbow, a radius and an ulna; and
a gutter-shaped knit extending from a lengthwise first end of the tubular knit, the gutter-shaped knit having a smaller length in a circumferential direction than the first end of the tubular knit, the gutter-shaped knit having a variation in a number of wales and a horseshoe-shaped cut-out section at a lateral side of the gutter-shaped knit, wherein the horseshoe-shaped cut-out section has a bottom edge being a lengthwise extension of the tubular knit, and
wherein a top end of the gutter-shaped knit is formed congruently with the bottom edge of the horseshoe-shaped cut-out section,
wherein the tubular knit and the gutter-shaped knits are comprised of inner protuberances, outer protuberances, and a base yarn.

9. A cylindrical bandage, comprising:
a tubular knit configured to correspond to a femur, tibia, a fibula bones, a heel and a foot; and
a gutter-shaped knit extending from a lengthwise first end of the tubular knit, the gutter-shaped knit having a smaller length in a circumferential direction than the first end of the tubular knit, the gutter-shaped knit having a variation in a number of wales and a horseshoe-shaped cut-out section at a lateral side of the gutter-shaped knit, wherein the horseshoe-shaped cut-out section has a bottom edge being a lengthwise extension of the tubular knit, and
wherein a top end of the gutter-shaped knit is formed congruently with the bottom edge of the horseshoe-shaped cut-out section.

* * * * *